US011253628B2

(12) United States Patent
Margulies et al.

(10) Patent No.: US 11,253,628 B2
(45) **Date of Patent: *Feb. 22, 2022**

(54) NEUROGENIC REGULATION OF BONE GROWTH AND BONE DEGRADATION

(71) Applicant: THE RESEARCH FOUNDATION FOR THE STATE UNIVERSITY OF NEW YORK, Albany, NY (US)

(72) Inventors: Bryan S. Margulies, Syracuse, NY (US); Sean D. Deboyace, Prattsville, NY (US)

(73) Assignee: The Research Foundation for the State University of New York, Albany, NY (US)

( * ) Notice: Subject to any disclaimer, the term of this patent is extended or adjusted under 35 U.S.C. 154(b) by 69 days.

This patent is subject to a terminal disclaimer.

(21) Appl. No.: 16/389,888

(22) Filed: Apr. 19, 2019

(65) Prior Publication Data

US 2019/0307918 A1 Oct. 10, 2019

Related U.S. Application Data

(63) Continuation of application No. 15/125,814, filed as application No. PCT/US2015/020412 on Mar. 13, 2015, now Pat. No. 10,265,437.

(60) Provisional application No. 61/953,475, filed on Mar. 14, 2014.

(51) Int. Cl.

| | |
|---|---|
| ***A61K 38/18*** | (2006.01) |
| ***A61L 27/22*** | (2006.01) |
| ***A61K 38/39*** | (2006.01) |
| ***A61L 27/24*** | (2006.01) |
| ***A61L 27/26*** | (2006.01) |
| ***A61L 27/52*** | (2006.01) |
| ***A61L 27/54*** | (2006.01) |
| ***A61L 27/56*** | (2006.01) |
| ***A61L 27/58*** | (2006.01) |

(52) U.S. Cl.

CPC ............ *A61L 27/227* (2013.01); *A61K 38/18* (2013.01); *A61K 38/1875* (2013.01); *A61K 38/39* (2013.01); *A61L 27/222* (2013.01); *A61L 27/24* (2013.01); *A61L 27/26* (2013.01); *A61L 27/52* (2013.01); *A61L 27/54* (2013.01); *A61L 27/56* (2013.01); *A61L 27/58* (2013.01); *A61L 2300/252* (2013.01); *A61L 2300/412* (2013.01); *A61L 2300/45* (2013.01); *A61L 2400/06* (2013.01); *A61L 2400/12* (2013.01); *A61L 2430/02* (2013.01)

(58) Field of Classification Search

None

See application file for complete search history.

(56) References Cited

U.S. PATENT DOCUMENTS

| | | | | |
|---|---|---|---|---|
| 8,334,260 | B2 * | 12/2012 | Rubin | A61P 43/00 514/16.7 |
| 8,906,864 | B2 | 12/2014 | Muller et al. | |
| 9,381,245 | B2 | 7/2016 | Cronstein et al. | |
| 10,265,437 | B2 * | 4/2019 | Margulies | A61L 27/222 |
| 2007/0248641 | A1 * | 10/2007 | Yang | A61K 38/30 424/423 |
| 2009/0028831 | A1 * | 1/2009 | Van Zant | A61K 35/16 424/93.7 |
| 2010/0322948 | A1 | 12/2010 | Mueller et al. | |
| 2011/0002972 | A1 | 1/2011 | Bosserhoff et al. | |
| 2013/0195863 | A1 | 8/2013 | Clezardin et al. | |
| 2013/0325144 | A1 | 12/2013 | Benkirane-Jessel et al. | |
| 2015/0175673 | A1 * | 6/2015 | Koh | A61P 19/08 514/16.9 |

FOREIGN PATENT DOCUMENTS

| | | | |
|---|---|---|---|
| WO | WO 2009/030500 | A1 | 3/2009 |
| WO | WO 2012/042289 | A1 * | 4/2012 |
| WO | WO 2012/113812 | A1 | 8/2012 |
| WO | WO 2012/139223 | A1 | 10/2012 |
| WO | WO 2013/187730 | A1 | 12/2013 |

OTHER PUBLICATIONS

International Search Report dated Jun. 15, 2015, received in International Application No. PCT/US2015/020412.

Supplemental European Search Report dated Sep. 18, 2017, issued in corresponding European Patent Application No. EP 15762288.7.

Mediero et al., "Netrin-1 is a Critical Autocrine/Paracrine Factor for Osteoclast Differentiation," Journal of Bone and Mineral Research, May 2015, 30(5):837-854.

Mediero et al., "Netrin-1 is a Critical Autocrine Factor for Osteoclast Differentiation," Journal of Bone and Mineral Research, 2013, 111 River St., Hoboken, NJ, Wiley-Blackwell, 6 pages.

Wu et al., "Repulsive Guidance Molecule (RGM) Family Proteins Exhibit Differential Binding Kinetics for Bone Morphogenetic Proteins (BMPS)," PLOS One, Sep. 2012, 7(9): 1-8.

* cited by examiner

*Primary Examiner* — Elizabeth C. Kemmerer

(74) *Attorney, Agent, or Firm* — Foley & Lardner LLP

(57) ABSTRACT

This disclosure relates to methods for promoting bone formation or reducing bone destruction. This disclosure also relates to methods for promoting the recruitment of mesenchymal stem cells (MSCs) to a local site of injury or surgical intervention in bone to promote healing. In addition, this disclosure relates to methods for reducing or preventing mineral formation or bone growth, or reducing bone mass. The methods disclosed herein are useful for treating conditions such as osteopetrosis or osteoradionecrosis.

5 Claims, 18 Drawing Sheets
(13 of 18 Drawing Sheet(s) Filed in Color)
Specification includes a Sequence Listing.

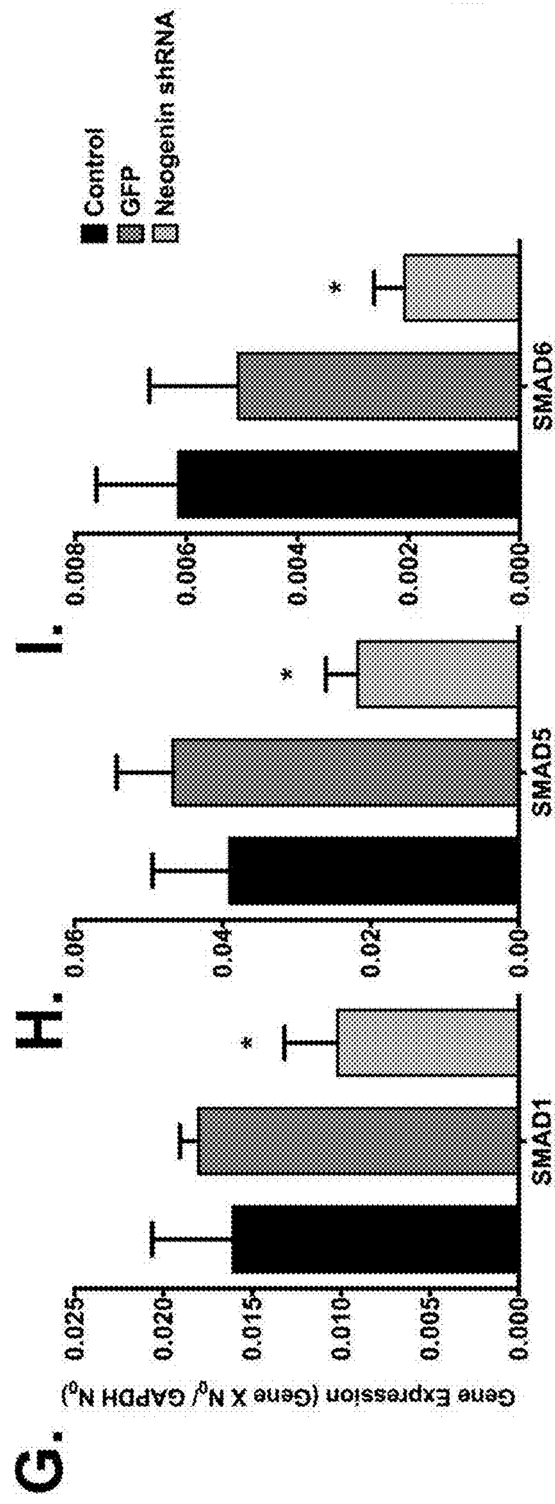
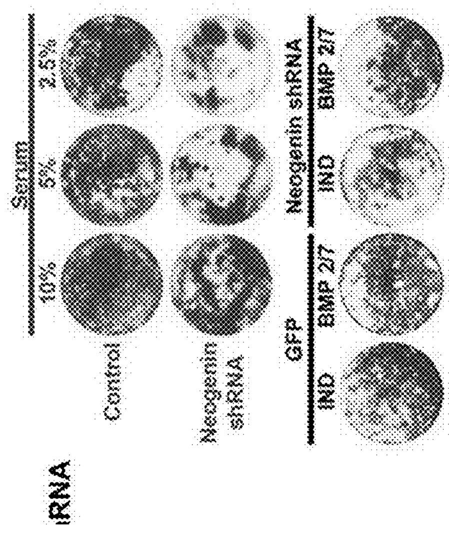
FIGURES 2G-2J

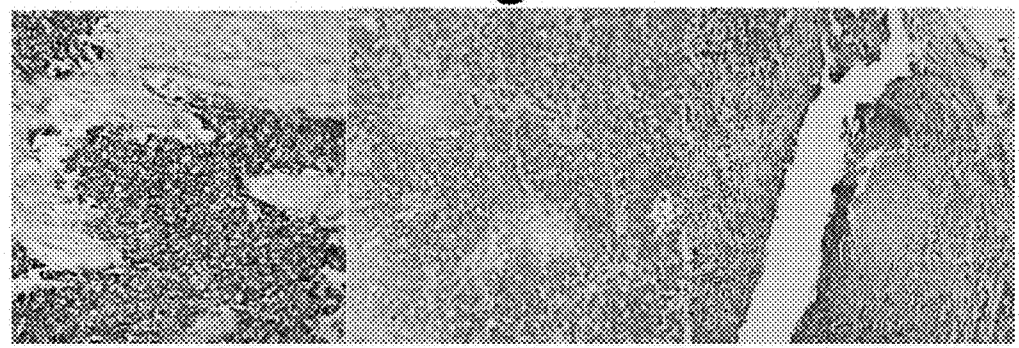
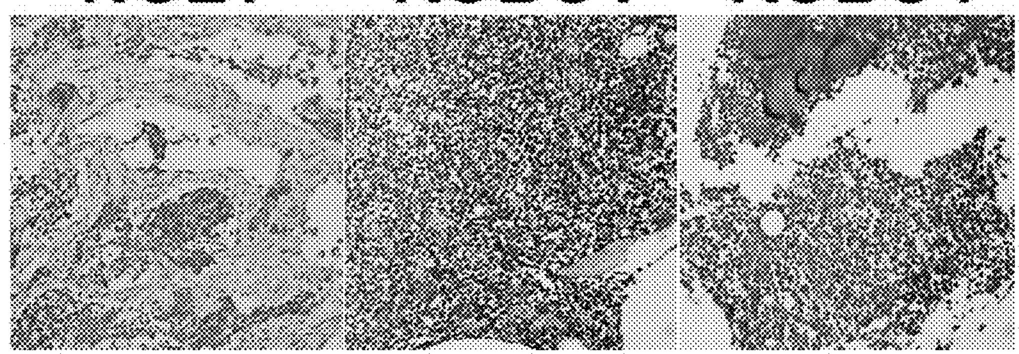
FIGURE 15
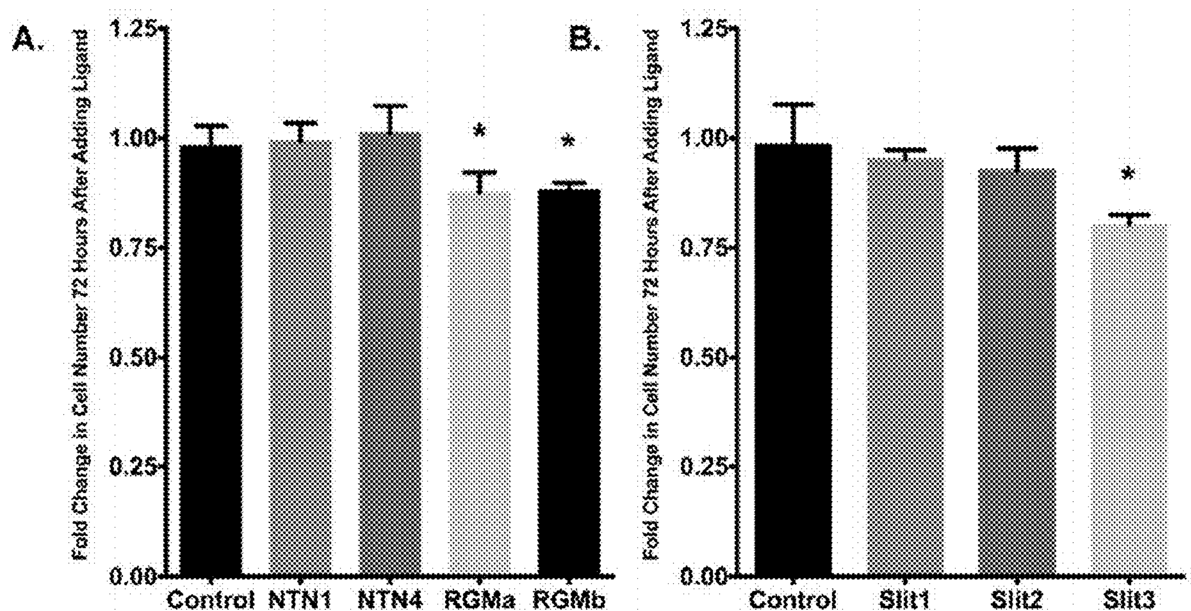
FIGURES 16A-16B

NEUROGENIC REGULATION OF BONE GROWTH AND BONE DEGRADATION

CROSS REFERENCE TO RELATED APPLICATION

This application is a Continuation of U.S. application Ser. No. 15/125,814, now U.S. Pat. No. 10,265,437, filed Sep. 13, 2016, which is a U.S. National Stage Application of International Application No. PCT/US15/20412, filed Mar. 13, 2015, which claims the benefit of priority from U.S. Provisional Application No. 61/953,475, filed Mar. 14, 2014, the entire contents of which are incorporated herein by reference.

BACKGROUND ART

Bone formation and degradation are tightly regulated by growth factor signaling between osteoblasts that are responsible for bone formation and osteoclasts that are responsible for bone re-absorption. Coupling bone formation by osteoblasts with degradation by osteoclasts has recently become a topic of intense study; with the list of growth factors identified as coupling factors expanding. Coupling bone formation with bone re-absorption requires the recruitment of osteoblasts and osteoclasts in parallel with the recruitment of their respective progenitor cells. Osteoblasts derive from mesenchymal stem cell (MSC) while osteoclasts derive from monocytes that are a part of the myeloid-lineage; however, it remains unknown how MSC or monocytes migrate from their niche in the bone marrow to sites of new bone formation. The current understanding of the spatial and temporal regulation of osteogenesis proposes that MSC migrate from their bone marrow niche to the endosteal surface; where the MSC differentiate into osteoblasts that produce new bone. In parallel, monocytes also migrate from their bone marrow niche to the endosteal surface; where they subsequently differentiate into osteoclasts that re-absorb bone. Growth factors known to regulate bone formation include TGFβ-, BMP- and the canonical Wnt-ligands. While osteoclast formation from monocyte precursors and bone re-absorption are regulated through the expression of MSCF, OPG and RANK-ligand. In parallel, osteoclast activity is also regulated by the expression of the TGFβ-, BMP- and the non-canonical Wnt-ligands. However, many developmental growth factors involved in tissue patterning, including TGFβ-, BMP- and the Wnt-ligands, promote bone formation and re-absorption. The maintenance of healthy bone requires constant remodeling, in which bone is made and destroyed continuously. The netrin-, RGM- and slit-ligands were indentified as growth factors that could potentially couple bone formation and re-absorption through the regulation of progenitor cell differentiation within the 3-dimensional structure of bone.

The introduction of an implant into bone results in a biochemical cascade that results in a pro-inflammatory response that is partially mediated by macrophages, which are derived from the myeloid lineage and can contribute to the degradation of bone or an implant material. Currently implants and implant materials are chosen to minimize the macrophage response while being optimally osteo-conductive and promoting maximum bone-implant integration. Alternatively, the introduction of autograph with an implant or the use of devitalized bone tissue graft has been employed in concert with the material properties of an implant as a means of increasing osteo-integration; however, these approaches have often been problematic. Ideally, materials could be designed to be both self-organizing and self-assembling.

Generating bone as an adjuvant therapeutic approach employed during orthopedic trauma procedures or during routine spine fusion procedures represents a continuing challenge in orthopedic surgery. Specifically, these adjuvant bone-generating therapies seek to increase the growth of healthy bone at the site of surgical intervention in parallel with decreasing the healing time for bone. In the last several decades a number of attempts have been made to use various growth factors with osteogenic potential, including BMP. Unfortunately, BMP based therapies intended to generate bone also carry a risk for tumorigenesis in patients who may be undergoing X-radiation therapy or possess nascent undetected tumor. Further, BMP based therapies cannot be used in patients with active tumor, which is particularly unfortunate since these patients would benefit significantly from therapies that increase bone formation during surgical intervention.

Impaired fracture healing continues to present a significant challenge in orthopedic surgery and bone healing. Fracture non-union rates as high as 5-20% have been reported. The morbidity and cost associated with the treatment of patients developing non-unions can be substantial. Approximately 10% of the 6.2-million fractures encountered each year have difficulty healing. Various options exist to help accelerate bone healing, with unproven efficacy. Iliac crest bone graft is still considered to be the gold standard but has significant issues related to harvest site co-morbidity. Growth factor based therapies that include platelet-derived growth factor (PDGF), fibroblast growth factor (FGF) and parathyroid hormone (PTH) has shown initial success in cell culture studies; however, their efficacy remains unproven in clinical application. An additional option, such as bone morphogenic protein-2 (BMP2) and BMP7, has been shown to have success in accelerating fracture healing with diaphyseal fractures. However, there are risks associated with the use of BMP that include increased infection, increased risk of tumor growth, and an increased risk of local osteolysis. Many of the risks associated with treatments that include BMP also preclude the use of BMP for patients with other pathologies.

The therapeutic ability to increase bone formation, as an adjuvant during orthopedic surgery, while not increasing the potential for tumor growth is currently a limitation of commercially available biologics, in treating complex orthopedic problems such as spine fusion, fracture healing and the management of fracture non-unions.

In the field of orthopedic trauma, particularly with open fractures with large defects and non-unions; autogenous/allogenic bone grafts are the primary treatment options. However, autogenous harvested bone graft, used as the gold standard to achieve bone formation, has risks of infection and donor site pain. Other allogenic bone graft substitutes have not shown similar efficacy when used singularly. The same limitations exist for spine surgery when these are used during fusions.

Cortical and cancellous bone derived from cadaveric sources serves to fill space and are primarily osteo-conductive without significant osteo-inductive potential. Hence, biologics such as PDGF, VEGF and BMP are used to increase rates of healing or fusion, and their application adds to the cost of treatment. However, these biologic therapies stimulate proliferation during development in a range of cell phenotypes, which presents an inherent and unacceptable oncologic risk.

De-mineralized bone matrix and calcium phosphate substitutes have not shown high efficacy at accelerated bone healing and also have significant cost associated with them due to production costs.

Recombinant BMP2 (rhBMP2) is a implant commercially developed by Medtronic known as Infuse that is distributed in small (4.2-mg of BMP2 with 2× collagen sponges for a 15-mg/cm$^3$ implant), medium (8.4-mg of BMP2 with 4× collagen sponges for a 15-mg/cm$^3$ implant), large (12-mg of BMP2 with 6× collagen sponges for a 15-mg/cm$^3$ implant) and large-II (12-mg of BMP2 with 1× collagen sponge for a 15-mg/cm$^3$ implant). All sizes of the Infuse implant are approved for spine and maxillofacial applications while only the large-II implant is approved for fracture. Infuse is administered by reconstituting the powdered BMP2 with sterile saline and then adding the BMP2-saline solution to the collagen sponge; after which the implant is delivered locally during surgical intervention.

Recombinant BMP7 (rhBMP7 or OP1) is an implant commercially developed by Sryker and now owned by Olympus known as OP1. OP1 is distributed as OP1-putty (20-mL vial containing powdered bovine cartilage and 3.3-mg of BMP7) or OP1-implant (1-g of powdered bovine cartilage and 3.3-mg of BMP7). The OP1-putty is approved for spine fusion surgeries while the OP1-implant is approved for treating fractures and fracture non-union surgery. OP1-putty or the OP1-implant is administered by reconstituting the powdered BMP7 with sterile saline and then adding the BMP7-saline solution to the collagen implant; after which the implant is delivered locally during surgical intervention.

Recent observations during neuro-development have identified a family of loosely related proteins and receptors that possess attractive and repulsive properties. The netrin-ligands are a class of four secreted (netrin-1, netrin-3, netrin-4 and netrin-5) that binds the DCC-, neogenin- and UNC5A-D receptors. The repulsive guidance molecules (RGMa and RGMb) are ligands that bind the neogenin-receptor and have been identified to antagonize netrin-ligand signaling. Netrin-ligands were initially identified in mammals as essential for commissural axon migration and may posses the ability to regulate attractive migration in bone. The slit-ligands (slit1, slit2 and slit3) and their roundabout receptor (ROBO1, ROBO2, ROBO3 and ROBO4) possess the ability to regulate repulsive cell migration in bone, since the slit-ROBO signaling axis has been shown to regulate neurite repulsive migration in the brain.

The netrin-ligands possess laminin-binding sites that act to sequester the netrin-ligand proteins in a collagen matrix and are considered an important regulatory element of netrin-ligand function. The slit-ligands have been shown to bind heparan sulfate and the interaction between heparan sulfate and the slit-ligand is required for slit-ligand function; whereas, collagen bound heparan is important in sequestering the slit-ligands.

SUMMARY OF THE DISCLOSURE

In one aspect, this disclosure provides a method for promoting bone formation or reducing bone destruction. The method is based on administration of an amount of the netrin, RGM or slit polypeptide ligands effective to promote bone formation or reduce bone destruction.

In another aspect, this disclosure provides a method for promoting the recruitment of mesenchymal stem cells (MSCs) to a local site of injury or surgical intervention in bone to promote healing. The method is based on administration of an amount of a netrin- or a slit-ligand polypeptide effective to promote bone formation while inhibiting bone degradation.

The injury can be, e.g., bone fracture or a surgical intervention such as would occur during the repair of a fracture through during spine fusion. In some embodiments, the polypeptide is administered locally to the site of injury.

In yet another aspect, this disclosure provides a method for reducing or preventing mineral formation or bone growth, or reducing bone mass. The method is based on administration of an amount of a RGMb or slit3 polypeptide ligand effective to reduce or prevent mineral formation or bone growth or reducing bone mass.

The methods disclosed herein are useful for treating conditions such as osteopetrosis or osteoradionecrosis.

DESCRIPTION OF THE DRAWINGS

The patent or application file contains at least one drawing executed in color. Copies of this patent or patent application publication with color drawing(s) will be provided by the Office upon request and payment of necessary fee.

(FIG. 1A) NTN4 gene expression decreased in osteoblasts, adipocytes and osteoclasts relative to MSC (*=p<0.026) while NTN4 expression in adipocytes and osteoclasts was further decreased relative to osteoblasts (#=p<0.002). (FIG. 1B) Neogenin gene expression was increased osteoblasts relative to MSC (*=p<0.045). However, neogenin gene expression was decreased in adipocytes and osteoclasts relative to osteoblasts (#=p<0.001). (FIG. 1C) UNC5b gene expression was increased in osteoblasts relative to MSC (*=p<0.024) while in adipocytes and osteoclasts UNC5b gene expression was decreased relative to osteoblasts (#=p<0.003). (FIG. 1D) UNC5c gene expression increased in osteoblasts (*=p<0.044) and adipocytes relative to MSC (*=p<0.007). (FIG. 1E) NTNG1 gene expression was increased in osteoblasts versus MSC (*=p<0.0492). (FIG. 1F) NGL1 gene expression was increased in osteoblasts relative to MSC (*=p<0.008) while both NGL1 gene expression was decreased in adipocytes and osteoclasts relative to osteoblasts (#=p<0.043). (FIG. 1G) NGL2 gene expression was decreased in osteoblasts relative to MSC (*=p<0.03). (FIG. 1H) Following the addition of osteogenic media to MSC cultures, both ALP gene expression (*=p<0.007) and OCN gene expression (*=p<0.008) increased. (FIG. 1I) The addition of adipogenic media to MSC cultures resulted in an increase in PPARg (*=p<0.05), FABP4 (*=p<0.026) and perilipin (*=p<0.001) gene expression. (FIG. 1J) In cultures of osteoclasts we identified CD14, cathepsin K (CTSK) and TRAP gene expression.

FIGS. 2A-2J: (FIG. 2A) NTN1 and NTN4 were added with osteo-induction media to cultured MSC. NTN1 and NTN4 increased mineral formation (red staining) in MSC beyond those effects observed when 25-ng of BMP2/7 or osteo-induction media were added. (FIG. 2B) MSC cultured to become osteoblasts (OB) was observed to have decreased NTN4 protein expression. (FIG. 2C) The full-length and γ-secretase fragments of neogenin were increased in lysates derived from MSC induced to become osteoblasts (OB) (2× patients, H1 and H2). (FIG. 2D) SaOS2 osteosarcoma tumor cells were transfected with neogenin shRNA or GFP. Neogenin shRNA SaOS2 cells expressed less neogenin. Protein lysates derived from mouse brain (mB) served as controls in parallel with the loading control actin. (FIGS. 2E and 2F) ID1 was decreased 63.4% (*=p<0.001) while ID2 gene expression was decreased 42.3% (*=p<0.039) in the neogenin deficient SaOS2 cells relative to control cells. (FIG.

2G) SMAD1 gene expression also decreased 36.6% in the neogenin deficient SaOS2 cells (*=p<0.04) versus controls. (FIG. 2H) SMAD5 gene expression decreased 44.3% in neogenin deficient SaOS2 cells (*=p<0.037) versus GFP-controls and non-transfected controls. (FIG. 2I) We also measured inhibitor SMAD6 decreased 66.3% in neogenin deficient SaOS2 cells (*=p<0.0007) relative to controls. (FIG. 2J) SaOS2 cells induced to make bone mineral were grown in decreasing concentrations of serum (10%, 5% and 2.5%). No significant effect was observed in mineral accumulation (red staining) in GFP-control and non-transfected control SaOS2 cells; however, a dose dependent decrease in mineral formation was observed in neogenin deficient SaOS2 cells versus controls. Treatment with BMP2/7 (25-ng) was able to partially restore mineral formation.

(FIG. 3A) Addition of NTN1 resulted in significant decreases in the numbers of adipocytes (*=p<0.008) while (FIG. 3B) NTN4 also resulted in a decrease in the numbers of adipocytes (*=p<0.001). 3 (FIGS. 3C, 3D and 3E) The addition of NTN1 resulted in a significant decrease in the numbers of osteoclasts (*=p<0.0003) and NTN4 resulted in a profound decrease in the numbers of osteoclasts (*=p<0.0001).

(FIG. 5G) When compared to PBS treated defects, treatment with NTN1 (*=p<0.0003) or NTN4 (*=p<0.0001) increased the quantity of bone within unicortical defects (Bv/Tv). (FIG. 5H) Changes in bone mass (Bv/Tv) corresponded with increased trabecular number (Tb.N) after treatment with NTN1 (*=p<0.006) or NTN4 (*=p<0.04). (FIG. 5I) Trabecular thickness (Tb.Th) increased in parallel with trabecular number following treatment with NTN1 (*=p<0.023) or NTN4 (*=p<0.011). (FIG. 5J) Consistent with the qualitative decrease observed in the defect, the measured diameter of the defect was also observed to decrease following treatment with NTN1 (*=p<0.009) or NTN4 (*=p<0.001).

(FIG. 6A) Neogenin gene expression increased approximately 2-fold in osteoblast cultures (*, p<0.028) compared to MSC while neogenin expression decreased in adipocyte and osteoclast (#, p<0.016) cultures compared to osteoblasts. (FIG. 6B) RGMa gene expression increased in both osteoblasts (*, p<0.005) and adipocytes (*, p<0.0001) when compared to MSC cultures. RGMa gene expression was also increased in adipocytes compared to osteoblasts and osteoclasts (#, p<0.0001). RGMa expression was further suppressed in osteoclasts compared to osteoblasts (X, p<0.014). (FIG. 6C) RGMb gene expression was decreased in cultures of osteoblasts (*, p<0.0035), adipocytes (*, p<0.0005) and osteoclasts (*, p<0.0035) relative to MSC cultures. (FIG. 6D) Alkaline phosphatase (ALP) and osteocalcin (OCN) gene expression is associated with osteogenesis. ALP gene expression increased in osteoblasts (*, p<0.0012) while OCN gene expression was also significantly increased (*, p<0.049). (FIG. 6E) The transcriptional regulator PPARg in parallel with the functional markers fatty acid binding protein-4 (FABP4) and perilipin were assayed in adipocyte cultures. PPARg (*, p<0.0018), FABP4 (*, p<0.005) and perilipin (*, p<0.0018) gene expression were all significantly increased in adipocyte cultures derived from MSC. (FIG. 6F) The myeloid lineage markers CD14, cathepsin-K (CTSK) and tartrate resistant acid phosphatase (TRAP) gene expression was measured in osteoclast cultures.

(FIG. 7A) Expression of the full length RGMa protein derived from protein lysates increased in osteoblasts (OB) versus MSC. The cleaved, soluble fraction of RGMa was unchanged following osteogenesis. Mouse brain lysates (mB) served as positive expression controls actin served a loading control. (FIG. 7B) RGMb expression was decreased in protein lysates derived from osteoblasts (OB) when compared to MSC. Mouse brain lysates (mB) served as positive expression controls and vinculin served as a loading control. (FIG. 7C) Serial doses of RGMa-ligand (1-, 10- or 100-ng) resulted in a weak, dose-dependent increase in mineral formation (red staining) while the RGMb-ligand did not alter mineral formation. The BMP2/7-ligand (25-ng) was added to MSC cultures induced to become osteoblasts as a positive control.

(FIG. 8A) The RGMa-ligand significantly increased the numbers of adipocytes following the addition of the 1-ng (*, p<0.0002), 10-ng (*, p<0.0004) and 100-ng (*, p<0.0002) doses. (FIG. 8B) The RGMb-ligand also resulted in significant increases in adipocyte numbers after adding the 1-ng (*, p<0.0037), 10-ng (*, p<0.0002) and 100-ng (*, p<0.0037) doses. (FIGS. 8C, 8D and 8E) The addition of 100-ng of either RGMa- (*, p<0.002) or RGMb-ligand (*, p<0.007) increased the numbers of osteoclasts in culture.

(FIGS. 9A, 9B and 9C) Unicortical defects were scanned using μCT (12-μm voxel resolution) and then analyzed. (FIG. 9D) Bone volume corrected by the total volume (Bv/Tv) was significantly decreased in defects treated with 100-ng of the RMGa-ligand (*, p<0.033) or 100-ng of the RGMb-ligand (*, p<0.012). (FIG. 9E) Trabecular number (TbN) was decreased, but only significantly for the RGMb-ligand treated defects (*, p<0.01). (FIG. 9F) Trabecular thickness (TbTh) also decreased in defects treated with RGMa- (*, p<0.014) or RGMb-ligands (*, p<0.012). (FIG. 9G) No change in the diameter of the defects was observed due to treatment with RGM-ligands.

(FIGS. 10J-10L) In parallel, oxytetracycline (OTC) staining associated with new mineral formation was robust in control defects (green staining) while OTC staining was significantly reduced in the RGMa- and RGMb-treated defects. OTC stained images were counter-stained with the nuclear stain PI and imaged at 20× (scale bar=100-μm).

(FIG. 11A) The slit2-ligand gene expression was significantly increased in osteoblast cultures relative to MSC cultures (*=p<0.021). (FIG. 11B) In contrast, slit3 gene expression was significantly decreased in osteoblasts and osteoclasts relative to MSC (*=p<0.002). (FIG. 11C) The ROBO1 receptor gene expression was increased in osteoblasts relative MSC (*=p<0.018). (FIG. 11D) The ROBO4 receptor was significantly increased in osteoclasts relative to osteoblasts and MSC (*=p<0.005). (FIG. 11E) Following the addition of osteo-induction media, the osteoblast phenotypic markers alkaline phosphatase (ALPL) and osteocalcin (OCN) increased significantly (*=p<0.01 and *=p<0.015, respectively). (FIG. 11F) The myeloid lineage phenotypic markers, CD14, cathepsin-K (CTSK) and tartrate resistant phosphatase (TRAPS) were expressed in osteoclasts cultures.

(FIG. 12A) The addition of slit1 or slit2 increased mineral formation while slit3 decreased mineral formation. The slit2-ligand in particular increased mineral more than BMP2/7. (FIG. 12B) The addition of 1-ng or 10-ng of the slit1-ligand increased adipocyte (fat cell) numbers (*=p<0.015) while 100-ng slit1 had not effect on adipocyte number. FIG. 12(C) The addition of 100-ng slit2 decreased adipocyte number (*=p<0.012). (FIG. 12D) In contrast, the addition of 1-ng of the slit3-ligand (*=p<0.001) while the 10-ng and 100-ng increased the number of adipocytes (*=p<0.015). (FIG. 12E-12G) Slit1 decreased osteoclast number (*=p<0.0002) while slit2 and slit3 increased osteoclast number (*=p<0.0001).

(FIG. 13A) Bone volume corrected by the total volume (Bv/Tv) was increased within unicortical defects treated with 100-ng of the slit1-ligand (*=p<0.0001) in parallel with increased Bv/Tv observed when defects were treated with the slit2-ligand (*=p<0.0003). The addition of slit3 had no effect on Bv/Tv. (FIG. 13B) Surprisingly, none of the slit-ligand has an effect on trabecular number (TbN). (FIG. 13C) Consistent with increased Bv/Tv, the addition of slit1 increased trabecular thickness (TbTh; *=p<0.0001) while slit2 increased TbTh significantly (*=p<0.0015). ThTb was unchanged in defects treated with slit3.

(FIG. 14A) Netrin-4 (NTN4) gene expression was decreased in osteoblasts (OB; *=p<0.001), RDES Ewing sarcoma of bone tumor cells (*=p<0.006), the Hs863 Ewing sarcoma of bone tumor cells (*=p<0.027), and SaOS2 osteosarcoma tumor cells (*=p<0.0085) relative to the MSC cultures. In contrast, NTN4 gene expression was significantly increased in the Hs822 Ewing sarcoma of bone tumor cells (*=p<0.05) relative to the MSC. (FIG. 14B) RGMb gene expression was decreased in osteoblasts (OB; *=p<0.034), RDES Ewing sarcoma of bone tumor cells (*=p<0.0214), and SaOS2 osteosarcoma tumor cells (*=p<0.0214) relative to the MSC cultures. In contrast, RGMb gene expression was significantly increased in the Hs822 Ewing sarcoma of bone tumor cells (*=p<0.0002) relative to the MSC. (FIG. 14C) Slit3 gene expression was decreased in osteoblasts (OB; *=p<0.0001), RDES Ewing sarcoma of bone tumor cells (*=p<0.0001), the Hs863 Ewing sarcoma of bone tumor cells (*=p<0.0001), and SaOS2 osteosarcoma tumor cells (*=p<0.0001) relative to the MSC cultures. In contrast, slit3 gene expression was significantly increased in the Hs822 Ewing sarcoma of bone tumor cells (*=p<0.006) relative to the MSC. (FIG. 14D) Neogenin gene expression was increased in osteoblasts (OB; *=p<0.02), RDES Ewing sarcoma of bone tumor cells (*=p<0.04), and SaOS2 osteosarcoma tumor cells (*=p<0.05) relative to the MSC cultures. (FIG. 14E) UNC5b gene expression was increased in osteoblasts (OB; *=p<0.04), Hs822 Ewing sarcoma of bone tumor cells (*=p<0.009), and Hs883 Ewing sarcoma of bone tumor cells (*=p<0.0004) relative to the MSC cultures. (FIG. 14F) ROBO1 gene expression was increased in RDES Ewing sarcoma of bone tumor cells (*=p<0.0023) relative to the MSC cultures.

FIG. 15: Immunhistochemical staining of Ewing sarcoma of bone sections of bone marrow biopsy demonstrating the tumor relationship to marrow. Ewing sarcoma of bone stained positive with CD99 (brown/red staining). Netrin receptors, neogenin and UNC5b, stained positive in the same Ewing tumor cells while the netrin-G coupled protein ligand receptor, NGL1, also stained in Ewing tumor samples. The slit-ligands receptors, ROBO1 and ROBO4, staining was robust within the Ewing sarcoma tumor samples. Methyl green was used as a nuclear stain (green/blue staining).

FIGS. 16A-16B: The addition of 100-ng of the netrin-1 (NTN1) or netrin-4 (NTN4) ligands had no effect on Ewing sarcoma of bone tumor cell proliferation, 72-hours after the addition of the ligands. In contrast, the addition of 100-ng of the RGMa or RGMb-ligands resulted in a significant decrease in RDES tumor cells number (*=p<0.0021). The addition of 100-ng of the slit1 or slit2-ligands had no effect on RDES tumor cell proliferation. In contrast, the addition of 100-ng of the slit3-ligand resulted in a significant decrease in RDES tumor cell number (*=p<0.0007) relative to the control cultures. The netrin-, RGM-, or slit-ligands had no effect on SaOS2 osteosarcoma tumor cells, or the Hs863 Ewing sarcoma tumor cells, or the Hs822 Ewing sarcoma tumor cells.

DETAILED DESCRIPTION

Figures 1A, 1B, 1C, 1D:
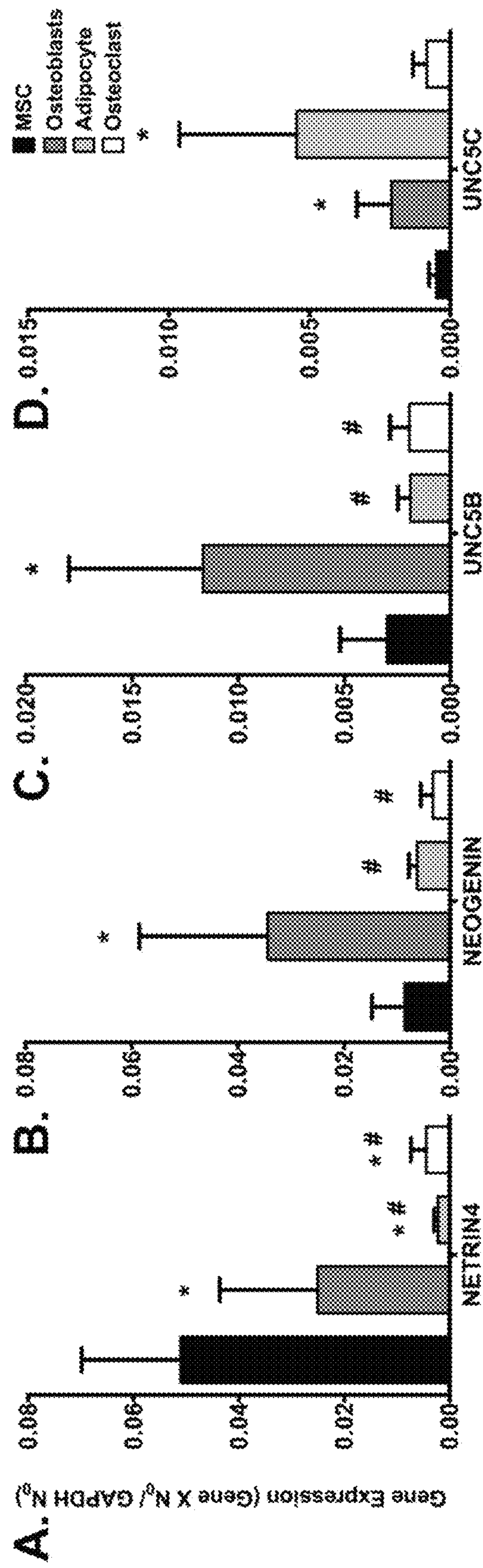
FIGS. 1A-1J.

In one aspect, it has been disclosed herein that netrin-1, netrin-4 and slit1 increase bone formation while decreasing osteoclast number and adipocyte number (fat cells). Increased bone formation is supported by mineral formation observed in culture and bone formation measured using microCT following a surgically induced unicortical defect. The decreased numbers of osteoclasts observed in culture supports increased bone formation. Decreased fat cell number corresponds with increasing bone and relates to bi-potential fate of MSC. The netrin-ligands increase in bone mass is driven by increased trabecular number, which is associated with recruiting more MSC to the unicortical defect. Slit1 increased bone mass is driven by increased trabecular thickness, which is associated with increased bone cell activity and not MSC recruitment.

In another aspect, it has been disclosed herein that slit2 increases bone formation, increases osteoclast numbers and decreases adipocytes number. Increased bone formation is demonstrated by mineral formation in culture and bone formation measured using microCT following a surgical induced unicortical defect. Decreased fat cell number corresponds with increasing bone and relates to the bi-potential fate of MSC. Slit2 increased bone mass is driven by increased trabecular thickness, which is associated with increased bone cell activity and not MSC recruitment.

In still another aspect, it has been disclosed herein that slit3 increased osteoclast number but not bone mass while RGMb decreased bone mass and increased osteoclast number. Adipocyte number was increased in slit3 and RGMb treated cultures. The RGMb results suggest that the RGM-ligands are antagonistic to netrin-ligands.

Administration of any of these ligands can be achieved through various routes. The surgical model resulted in an injury containing abundant collagen, laminin, fibronectin and heparin; all of which are required for netrin and slit function and these ligands contain binding sites for these matrix proteins. Thus, in some embodiments, these ligands can be administered locally at the site of a fracture or at the site of an orthopedic surgical procedure, all of which results in bleeding. In other embodiments, these ligands can be administered in other routes, e.g., intravenous, intramuscular, parenternal, among others.

The administration of these ligands alone or in combination with an implant as a means to control the migration of MSC to an implant and the formation of bone (netrin-1 or netrin-4) or to prevent the migration of MSC and inhibit bone formation (slit3). In parallel, netrin-1, netrin-4 or slit1-ligands inhibit bone degradation (through decreased osteoclast number) of bone or implant material. Additionally, the controlled degradation of bone or an implant material can be mediated by the addition of slit3 or RGMb (through increased osteoclast number).

Administration of any of the ligands disclosed herein can be performed to promote bone growth, or reduce bone destruction, both of which results in increased bone mass; or to reduce bone mass, in subjects in need thereof. For example, the administration of netrin-1, netrin-4 and slit1 may be useful in treating osteonecrosis or osteoradionecrosis, in which osteoblast activity is diminished and adipocytes number (i.e. the accumulation of fat) is increased when MSC fail to migrate and differentiate in the injured tissue space. The administration of slit3 and RGMb may be useful in treating osteopetrosis (pathologically high bone mass) for which there are few therapeutic options.

In one aspect, the invention provides a method for promoting bone formation and/or reducing bone degradation. The method includes administering an amount of the netrin- or slit-ligand polypeptide effective to promote bone formation or reducing bone destruction (i.e. re-absorption). In one embodiment, the netrin-ligand polypeptide is netrin-1, netrin-4, slit1, or slit2, or a combination thereof. Suitable combinations include, for example, netrin-1 and netrin-4; slit1 and slit2; netrin-1, netrin-4, and slit1; and netrin-1, netrin-4, slit1, and slit2. In specific embodiments, the netrin- or slit-ligand polypeptide is a polypeptide of a mammalian origin, such as human, rodent (mouse or rat). In some embodiments, the polypeptide(s) employed is (are) of human origin.

In another aspect, the invention provides a method for promoting the migration and/or differentiation of mesenchymal stem cells (MSC) to a site of injury or surgical intervention in bone to promote healing by directly promoting the differentiation of MSC into an osteoblast while inhibiting differentiation into an adipocyte (fat cell). The method includes administering an amount of a netrin- or a slit-ligand polypeptide effective to promote the migration or differentiation of mesenchymal stem cells (MSC) to a site of injury or surgical intervention in bone. In one embodiment, the netrin-ligand polypeptide is netrin-1, or netrin-4, or a combination thereof. In specific embodiments, the netrin-ligand polypeptide is a polypeptide of a mammalian origin, such as human, rodent (mouse or rat). In some embodiments, the polypeptide(s) employed is (are) of human origin.

In one aspect, the invention provides a method for preventing or reducing the migration of mesenchymal stem cells (MSC) to a site of injury or surgical intervention in bone to inhibit bone formation. The method includes administering an amount of a slit-ligand polypeptide effective to prevent or reduce the migration of mesenchymal stem cells (MSC) and/or MSC differentiation into an osteoblast to a site of injury or surgical intervention in bone. In one embodiment, the slit-ligand polypeptide is slit3. In specific embodiments, the polypeptide is a polypeptide of a mammalian origin, such as human, rodent (mouse or rat). In some embodiments, the polypeptide(s) employed is (are) of human origin.

In another aspect, the invention provides a method for reducing or preventing mineral formation or bone growth, or for reducing bone mass. The method comprises administering an amount of the RGMb-ligand polypeptide effective to reducing or preventing mineral formation or bone growth or reducing bone mass. In one embodiment, the RGMb-ligand polypeptide is a human RGMb polypeptide. In another embodiment, the RGMb polypeptide is a rodent (e.g., mouse or rat) RGMb polypeptide. In yet another embodiment, the RGMb polypeptide is a human or rodent RGMb polypeptide.

In still another aspect, this disclosure provides a method for promoting controlled bone growth. The method includes utilizing nano-particles or a collagen based carrier (e.g., a collagen sponge, a powdered collagen, or a collagen based gelatin hydrogel) with alternating layers of ligands that are released over a period of time; for example, with a layer of netrin-1 and/or netrin-4 which promote osteoblast formation, on top of an inner layer of slit3 or RGMb, which inhibit bone formation and promote the degradation of the implant. This process of controlled bone formation coupled with osteoblast inhibition and implant degradation will produce a bone-like template.

In one aspect, this disclosure provides a method of treating osteonecrosis or osteoradionecrosis based on administration of netrin-1, netrin-4, or slit1, or a combination thereof.

In another aspect, this disclosure provides a method of treating osteopetrosis based on administration of slit3, RGMa or RGMb, or a combination thereof.

In another aspect, this disclosure provides a method of treatment using netrin-1, netrin-4, slit1, slit2, slit3, RGMa or RGMb for orthopedic injuries or surgical interventions that do not possess the capacity to promote tumor growth.

In some embodiments, this disclosure provides a suitable dose range, through which a netrin-1 ligand (1-ng to 50 microgram) and/or a netrin-4 ligand (1-ng to 50 microgram) is administered and effective to increase bone formation and/or decrease bone degradation through decreased osteoclast formation and decreased adipocyte formation in a dose dependent fashion. Specific dose amounts can be, for example, 10 ng, 25 ng, 50 ng, 75 ng, 100 ng, 200 ng, 500 ng, 1 μg, 5 μg, 10 μg, 20 μg, 50 μg, or an amount between any of the listed doses. The precise total dose amount that is effective will depend on the extent of the injury or surgical application and the carrier to be used. For example, 50 ng in 1 microliter of saline or any equivalent dose (e.g., 100-ng in 2 microliter or 1414.14-ng/$cm^3$), of a netrin-1 ligand or a netrin-4 ligand can be administered to an injury or local surgical site that results in substantial, accelerated bone formation and inhibition of osteoclast numbers within the surgical area.

In other embodiments, this disclosure provides a suitable dose range, through which a RGMa-ligand (1-ng to 50 microgram) and/or a RGMb-ligand (1-ng to 50 microgram) is administered and effective to to inhibit bone formation while increasing osteoclast formation. Specific dose amounts can be, for example, 10 ng, 25 ng, 50 ng, 75 ng, 100 ng, 200 ng, 500 ng, 1 μg, 5 μg, 10 μg, 20 μg, 50 μg, or an amount between any of the listed doses. The precise total dose amount that is effective will depend on the extent of the injury or surgical application and the carrier to be used. For example, 50 ng in 1 microliter of saline or any equivalent dose (e.g., 100-ng in 2 microliter or 1414.14-ng/$cm^3$), of a RGMa-ligand or a RGMb-ligand can be administered to an injury or local surgical site that results in inhibited bone healing through an increase in osteoclast numbers within the surgical area.

In some embodiments, this disclosure provides a suitable dose range, through which a slit1-ligand (1-ng to 50 microgram) and/or a slit2-ligand (1-ng to 50 microgram) is administered and effective to increase bone formation for slit1-ligand and slit2-ligand in a dose dependent fashion while decreasing bone degradation after treatment with the slit1-ligand. Specific dose amounts can be, for example, 10 ng, 25 ng, 50 ng, 75 ng, 100 ng, 200 ng, 500 ng, 1 μg, 5 μg, 10 μg, 20 μg, 50 μg, or an amount between any of the listed doses. The precise total dose amount that is effective will depend on the extent of the injury or surgical application and the carrier to be used. For example, 50 ng in 1 microliter of saline or any equivalent dose (e.g., 100-ng in 2 microliter or 1414.14-ng/cm$^3$), of a slit1-ligand or a slit2-ligand can be administered to an injury or local surgical site that results in substantial bone formation for the slit1-ligand and the slit2-ligand while the slit1-ligand can also inhibit osteoclast numbers within the surgical area.

In other embodiments, this disclosure provides a suitable dose range, through which a slit3-ligand (1-ng to 50 microgram) is administered and effective to decrease bone formation in culture and not increase bone formation in a surgically administered bone defect. Specific dose amounts can be, for example, 10 ng, 25 ng, 50 ng, 75 ng, 100 ng, 200 ng, 500 ng, 1 μg, 5 μg, 10 μg, 20 μg, 50 μg, or an amount between any of the listed doses. The precise total dose amount that is effective will depend on the extent of the injury or surgical application and the carrier to be used. For example, 50 ng in 1 microliter of saline or any equivalent dose (e.g., 100-ng in 2 microliter or 1414.14-ng/cm$^3$), of a slit3-ligand can be administered to an injury or local surgical site that results in impaired bone formation for the slit3-ligand through increased osteoclast numbers within the surgical area.

In another aspect this disclosure provides for the combination of a netrin-1 ligand, netrin-4 ligand, slit1-ligand or slit2-ligand to a bovine collagen implant, in a manner similar to either Infuse (BMP2) or OP1-putty or OP1-implant, that is supplied with a bovine collagen sponge or powdered bovine collagen. A netrin-1 ligand, netrin-4 ligand, slit1-ligand or slit2-ligand will be administered by reconstituting the powdered netrin-1 ligand, netrin-4 ligand, slit1-ligand or slit2-ligand with sterile saline and then adding the ligand-saline solution to the collagen implant; after which the implant will be delivered locally to the site of surgical intervention.

In another aspect this disclosure provides for the combination of a RGMa-ligand, RGMb- ligand or slit3-ligand to a bovine collagen implant, in a manner similar to either Infuse (BMP2) or OP1-putty or OP1-implant, that is supplied with a bovine collagen sponge or powdered bovine collagen. A RGMa-ligand, RGMb-ligand or slit3-ligand will be administered by reconstituting the powdered RGMa-ligand, RGMb-ligand, or slit3-ligand with sterile saline and then adding the ligand-saline solution to the collagen implant; after which the implant will be delivered locally to the site of surgical intervention.

Specific examples of netrin, slit and RGMb polypeptides suitable for use herein include SEQ ID NOS: 2, 4, 6, 8, 10, 11, 13, 14, 16, 17, 22 and 23, polypeptides having amino acid sequence identity of at least 85%, 90%, 95%, 97%, 98%, 99%, or greater than 99% to any of SEQ ID Numbers: 2, 4, 6, 8, 10, 11, 13, 14, 16, 17, 22 or 23, and functional or bioactive fragments thereof.

Sequence Identifiers, Description, and GenBank Accession Numbers

SEQ ID NO: 1 Mouse Netrin-1, nucleic acid, NM_008744
SEQ ID NO: 2 Mouse Netrin-1, amino acid, NP_032770,
SEQ ID NO: 3 Human Netrin-1, nucleic acid, NM_004822
SEQ ID NO: 4 Human Netrin-1, amino acid, NP_004813
SEQ ID NO: 5 Mouse Netrin-4, nucleic acid, NM_021320
SEQ ID NO: 6 Mouse Netrin-4, amino acid, NP_067295
SEQ ID NO: 7 Human Netrin-4, nucleic acid, NM_021229
SEQ ID NO: 8 Human Netrin-4, amino acid, NP_067052
SEQ ID NO: 9 Human SLIT1, nucleic acid, NM_003061.2
SEQ ID NO: 10 Human SLIT1, amino acid, NP_003052.2
SEQ ID NO: 11 Mouse SLIT1, amino acid, Q80TR4
SEQ ID NO: 12 Human SLIT2, nucleic acid, NM_004787.1
SEQ ID NO: 13 Human SLIT2, amino acid, NP_004778.1
SEQ ID NO: 14 Mouse SLIT2, amino acid, Q9R1B9
SEQ ID NO: 15 Human SLIT3, nucleic acid, NM_003062.3
SEQ ID NO: 16 Human SLIT3, amino acid, NP_003053.1
SEQ ID NO: 17 Mouse SLIT3, amino acid, Q9VWB4
SEQ ID NO: 18 Human RGMa, nucleic acid, NM_001166289.1
SEQ ID NO: 19 Human RGMa, amino acid, NP_001159761.1
SEQ ID NO: 20 Mouse RGM-A; amino acid, Q6PCX7
SEQ ID NO: 21 Human RGMb, nucleic acid, NM_001012761.2
SEQ ID NO: 22 Human RGMb, amino acid, NP_001012779.2
SEQ ID NO: 23 Mouse RGM-B; amino acid, Q7TQ33

The present description is further illustrated by the following examples, which should not be construed as limiting in any way. The contents of all cited references (including literature references, issued patents, and published patent applications as cited throughout this application) are hereby expressly incorporated by reference.

EXAMPLE 1

Netrin-Ligands Regulate Bone Formation and Bone Re-Absorption

Methods: Human bone marrow was collected from consenting adult patients undergoing either an elective primary proximal femoral total hip arthroplasty or elective primary distal femoral total knee arthroplasty (n=6, mean age 65) as a part of an IRB approved study. Human MSC were derived from the adherent fraction of cells derived from each whole bone marrow aspirate collected while the monocyte population was collected from the non-adherent fraction of the bone marrow. The monocyte fraction was enriched through sub-culture with 100-ng/mL recombinant human macrophage colony-stimulating factor (MCSF; Wyeth). In parallel experiments described below, the femurs from 3-week (n=10) and 16-week (n=20) old male mice were collected and then the bone marrow was flushed from the femur according to the following: A 21-gauge needle was inserted into the femoral intramedular canal after the removal of the proximal and distal ends of the femur. Media was then carefully passed through the proximal end of the femur, which forced the bone marrow to pass out of the bone. Finally, the bone marrow pellet was mechanically disassociated using an 18-gauge needle and then passed through a 70-μm mesh filter. These whole bone marrow aspirates were used to generate osteoclasts. Cells were maintained in Dulbecco's Modification of Eagle's Media (DMEM) containing 10% fetal calf serum (v/v) and 1% penicillin-streptomycin-glutamine (PSG; Cellgro, Mediatech). Recombinant human netrin-ligands (NTN1 and NTN4) were diluted in PBS (R&D Systems). The responsible IACUC committee approved all of the animal studies described in this work.

Gene Expression Analysis: MSC, osteoblasts and adipocytes derived from human bone marrow were assayed for changes in gene expression. In parallel, osteoclasts derived from human monocytes were also assayed for changes in myeloid gene expression. Gene data were derived from two independently generated samples collected from at least three patients. mRNA was purified using RNeasy Plus Mini columns (Qiagen) and cDNA was synthesized using the iScript cDNA Synthesis Kit (Bio-Rad). Gene expression was analyzed using quantitative PCR (qPCR) using 100-ng of cDNA mixed with Fast Plus EvaGreen Master Mix (Biotium). In each experiment GAPDH served as a control, negative controls contained no-template and a standard curve was generated using serial dilutions of a chemically synthesized sequence for GAPDH (0, 1, 10 and 100 femtograms; Integrated DNA Technologies). Gene expression was evaluated using Pfaffl's method, in which the efficiency of each primer (E) and the starting gene product concentration (No) are calculated from the linear region of the fluorescence-crossing threshold curve using the software LinRegPCR (v2013.0). Experiments were considered valid when the control gene GAPDH fell within the standard curve and the primer efficiencies (E) were calculated to be E>=1.8. The presence of a single gene product was confirmed using a melt-curve analysis and product size was confirmed using gene product gel-electrophoresis.

Protein Expression through Western Blot Analysis: Human MSC, osteoblasts and osteoclasts were lysed with cold RIPA buffer (Pierce Thermo Scientific) containing 2-mM iodoacetamide, 2-mM benzamidine hydrochloride, 0.1-mM ethylmaleimide, 1% PMSF and the Halt Protease Inhibitor Cocktail (Pierce Thermo Scientific). Protein was also assayed from supernatant samples derived from MSC cultures. Protein lysates were analyzed from at least two replicates generated from three patient samples. Total protein was assayed using the BCA Protein Assay Kit (Thermo) following the manufacturers instructions. Samples were loaded (20-μg/well) onto a 10-20% Mini-Protean Tris-Tricine Precast Gel (Bio-Rad) with the Page Ruler Pre-stained NIR Protein Ladder (Bio-Rad) and transferred to a nitrocellulose membrane (Bio-Rad). NTN4, NTNG1, the UNC5 receptors (UNC5b and UNC5c) and NGL1 were identified on membranes blocked using 5% non-fat milk and the following primary antibodies (Santa Cruz Biotechnologies): NTN4 (1:500), NTNG1 (1:500), UNC5b (1:500), UNC5c (1:500) and NGL1 (1:500). Vinculin (1:500) or actin (1:500) served as loading controls. The γ-secretase fragment (aa1171-aa1345) or the c-terminal of the neogenin-receptor was detected using the H-175 (1:1000) or C-20 (1:500) antibody clones directed against neogenin-receptor, respectively. Antibodies were detected using an H RP-conjugated micro-polymer conjugated secondary antibody (ImmPress kit, Vector Labs) in conjunction with the Clarity Western ECL substrate (Bio-Rad). Mouse brain protein lysates (mB) were used as positive-expression controls.

Immunofluorescence and Morphology: Tibias from 3-week (n=10) and 16-week (n=20) old mice were fixed in 2% paraformaldehyde, simultaneously decalcified and cryo-protected using a solution of 15% EDTA and 30% sucrose, and then snap-frozen using liquid nitrogen and sectioned at 8-μm using a cryo-microtome (Leica 3050). Patterns in ligand and receptor expression were identified using the following primary antibodies: NTN4 (1:250), NTNG1 (1:250), neogenin (1:250), UNC5b (1:250), UNC5c (1:250), NGL1 (1:250) and FABP4 (1:250). Antibodies were detected using Alexa Fluor-488 or -568 secondary antibodies (1:500; Invitrogen). MSC were also grown on glass discs and fixed with 2% paraformaldehyde. MSC were incubated with primary antibodies against NTN1 (1:250), NTN4 (1:250), NTNG1 (1:250), neogenin (1:250), UNC5b (1:250), UNC5c (1:250), NGL1 (1:250) and nucleostemin (1:250) Antibodies were detected using Alexa Fluor-488 or -568 antibodies (1:500; Invitrogen). Nuclei were counter-stained with 10-μg/ml 4',6-diamidino-2-phenylindole (DAPI, Sigma).

Osteogenesis: Osteogenic potential in MSC was assayed by chemically inducing mineral formation. MSC from at least three human patients were seeded at $5\times10^3$ cells per well and allowed to become confluent and woven prior to the addition of osteo-induction media. Induction media consisted of DMEM containing 20% FCS (v/v) and 1% PSG supplemented with 25-μg/mL of acscorbic-2-phosphate (Sigma), 100-nM dexamethasone (Sigma) and the following dosing regimen of β-glycerophosphate (BGP; Sigma): 1× media change with 5-mM BGP, 1× media change with 10-mM BGP and 1× media change with 20-mM of BGP. Netrin-ligands (1-, 10- and 100-ng) were added at each post-induction media change. Positive control wells were treated with 25-ng of the recombinant human BMP2/BMP7-ligand (R&D Systems) with the first addition of induction media. After the appearance of mineral nodules, cells were fixed with 70% ice-cold EtOH (Sigma) and then stained using 40-mM alizarin red-S (pH 4.2, Sigma). Osteogenesis experiments were repeated at least twice for each patient.

Adipogenesis: Adipogenic potential in MSC was assayed by chemically inducing adipocyte differentiation and lipid accumulation. MSC from at least three human patient samples were seeded at $5\times10^3$ cells per well and allowed to become confluent prior to the addition of adipo-induction media. Induction media consisted of DMEM containing 10% FCS (v/v) and 1% PSG supplemented with 5-μM rosiglitizone (Caymen Chemical), 500-μM 3-isobutyl-1-methylxanthine (IBMX; Sigma), 1-μM dexamethasone (Sigma) and 1-μg/mL recombinant human insulin (rinsulin, Sheffield Bio-Science). Induction media including the netrin-ligands (1-, 10- and 100-ng) was added to cultures at each media change; 2× media changes over a 7-day post-induction period. Cultures were fixed with 2% paraformaldehyde and imaged with the lipophilic fluorescent stain nile red (excitation at 488-nm; Sigma). Nuclei were counter-stained with DAPI. Estimates of adipocytes numbers were obtained through Cavalieri sampling in conjunction with a modification of the fractionator technique used in un-biased stereology, in which a particular well was divided into parallel sections that served as counting regions. Adipogenesis experiments were repeated at least twice.

TRAP Staining and the Assay of Osteoclast Number: Osteoclasts were derived from either an enriched population of human monocytes or from mouse non-enriched whole bone marrow aspirates. Three human patient bone marrow samples were assayed in parallel with samples collected from 3-week (n=10) and 16-week (n=20) mouse bone marrow. The monocyte fraction was stimulated to become osteoclasts by culturing $1\times10^6$ cells with 25-ng/mL of MCSF and 25-ng/mL of recombinant human or mouse RANK-ligand (R&D Systems) in the presence of the NTN1- or NTN4-ligands (100-ng). Osteoclasts were stained with tartrate resistant acid phosphatase (TRAP; Sigma Leukocyte Acid Phosphatase Kit 387-A) and counted when cells stained TRAP-positive and had at least three nuclei. Estimates of osteoclast number were obtained by Cavalieri sampling and a modification of the fractionator technique.

shRNA Knock-down of the Neogenin-receptor: SaOS2 osteosarcoma tumor cells were employed to model osteogenesis. We inhibited neogenin-receptor activity using a commercially available neogenin shRNA-lentivirus or transfected SaOS2 cells with a GFP lentivirus used as a control (Santa Cruz Biotechnologies). SaOS2 cells were then induced to become osteoblasts using 10%, 5% or 2.5% serum and then assayed for BMP-target genes (ID1, ID2, SMAD1, SMAD2, SMAD3, SMAD4, SMAD5, SMAD6, SMAD7 and SMAD8/9).

Unicortical Defect Model: Male 3-week old C57BLJ6 mice (n=5 per treatment group) were injected with NTN1 or NTN4 following the creation of a unicortical defect. Briefly, a small incision (approximately 3-mm) was made just below the knee joint, located on the medial side of the tibia just below the tibial tuberosity on the tibial crest. In young animals the physeal plate is clearly visible and the drill bit was placed approximately 1-mm below this point. The drill-bit produces a unicortical defect with dimensions 300-μm diameter×1-mm depth. A Hamilton Neuros RN 10-4 syringe with a 33-gauge blunt tip needle was used to inject the netrin-ligands (NTN1 or NTN4 at 100-ng in 2-4) directly into the unicortical defect at a rate no faster than approximately 0.1-4 per second. The left-limb tibias served as contra-lateral surgical controls, in which animals received a unicortical defect and 2-4 of saline was injected. These same mice were injected with oxytetracycline (50-μg/kg; OTC) administered intraperitoneally to measure bone apposition 48-hours prior to euthanasia. Mice were euthanized 5-days after surgery, hind limbs were collected and tibias were fixed for immunofluorescense, TRAP staining and OTC associated bone growth.

MicroCT Analysis of Unicortical Defects: High-resolution images of the tibia were acquired with a μCT imaging system (μCT40; Scanco Medical). Tibias were scanned at 45-keV with an isotropic voxel size of 12-μm. An analysis region was selected from axial sections to include the entire unicortical defect bounded by the endosteal cortical wall. The volume corrected bone volume (bone volume/total volume; Bv/Tv), trabecular number (TbN) and trabecular thickness (TbTh) were calculated using the Scanco software. The maximum diameter of the defect was determined using unbiased stereology, in which the maximum linear distance was measured between opposing sides of the defect through serial sections. The maximum diameter was determined using the BoneJ plug-in for ImageJ (NIH Research Services Branch; http://rsbweb.nih.gov/ij/).

Statistical Analyses: Prism statistical software (Graphpad) was used to analyze data. Means and standard deviations were calculated. Data were analyzed by 1-way or 2-way ANOVA using the Holm-Sidak post-hoc correction for multiple comparisons with significance set at $p<0.05$.

Figures 1E, 1F, 1G, 1H, 1I, 1J:
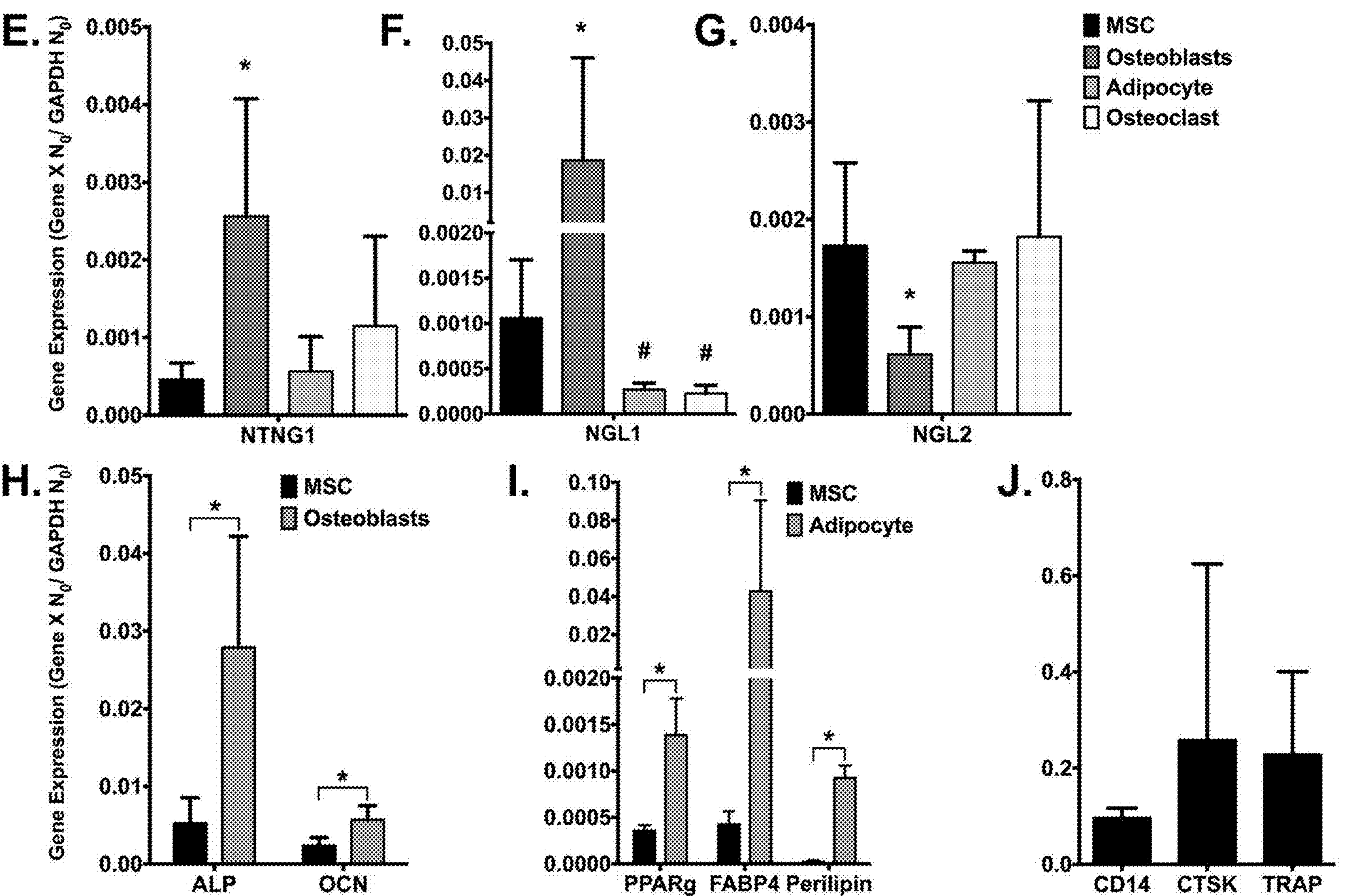

Results:

Netrin-ligands and netrin-receptors are expressed in the MSC and monocyte lineages: NTN4 gene expression was significantly decreased in osteoblasts, adipocytes and osteoclasts when compared to MSC ($p<0.026$). (FIG. 1A) Conversely, the netrin-receptors that were detected (neogenin, UNC5b and UNC5c) were all significantly increased in osteoblasts when compared to MSC ($p<0.045$). (FIGS. 1B, 1C, 1D) Interestingly, UNC5c gene expression was greatest in adipocytes when compared to MSC ($p<0.007$). (FIG. 1D) However, both neogenin and UNC5b gene expression were significantly less in adipocytes and osteoclasts when compared to osteoblasts ($p<0.003$). NTNG1 gene expression was significantly increased in osteoblasts compared to MSC ($p<0.0492$) (FIG. 1E) Likewise, the NTNG1 receptor NGL1 gene expression was also significantly increased in osteoblasts versus MSC ($p<0.008$) while gene expression for the NGL2 receptor was significantly decreased in osteoblasts ($p<0.03$). (FIGS. 1F and 1G) No change in gene expression between the various MSC or monocyte lineages was observed for NTN1, NTN3, NTN5 and NTNG2 ligands. (not shown) Further, UNC5a, UNC5d, DCC, DSCAM and NGL3 gene expression was undetectable. Alkaline phosphatase (ALP) and osteocalcin (OCN) gene expression were significantly increased in osteoblasts when compared to MSC ($p<0.009$). (FIG. 1H) In parallel, adipocyte specific genes (PPARγ, FABP4 and perilipin) were all increased in adipocytes when compared to MSC ($p<0.01$). (FIG. 1I) Osteoclastic specific genes (CD14, CSTK and TRAP) were also observed in monocytes cultured to become osteoclasts. (FIG. 1J)

NTN4, UNC5b and neogenin staining was observed to be widespread in bone marrow and along the endosteal surface of bone: Fluorescent staining revealed that NTN4 was only expressed within a small group of chondrocytes within the reserve zone of the growth plate. Neogenin-was weakly expressed by the chondrocytes of the proliferative zone and strongly expressed by chondrocytes of hypertrophic zone of the growth plate. Both NTN4 and neogenin were abundantly observed in the region of the metaphysis adjacent to the growth plate (the chondro-osseous junction). Tomato lectin and neogenin staining demonstrated that the monocyte lineage is abundant near the chondro-osseous junction, which could reflect osteoclast activity that is responsible for degrading the mineralized cartilage of the growth plate. UNC5b and UNC5c staining was observed in the chondrocytes within the hypertrophic zone of the growth plate while UNC5c staining was also seen in chondrocytes of the reserve-proliferative zone. UNC5b and UNC5c staining was also identified near the chondro-osseous junction of the growth plate. Additionally, strong staining for NTN4, neogenin and UNC5b was observed in the layer of osteoblasts lining the endosteal surface of bone. Importantly, only neogenin staining was observed in osteocytes within the cortical bone. Further, within the bone marrow NTN4 stained widely. Finally, both neogenin and UNC5b staining was greatest in the osteoblasts lining the endosteal surface of trabecular bone.

NTNG1 and NGL1 were expressed by chondrocytes within the growth plate and osteoblasts lining the endosteal surface: NTNG1-ligand and NGL1-receptor staining were observed in chondrocytes located within the reserve-proliferative zone of the growth plate while neither NTNG1 nor NGL1 staining were seen within the hypertrophic zone. NTNG1 and NGL1 staining was also identified in the metaphyseal region adjacent to the growth plate (chondro-osseus junction). NTNG1 and NGL1 staining was also observed in osteoblasts lining the endosteal surface and throughout the bone marrow adjacent to the endosteal surface. Trabecular bone osteoblasts within the metaphysis stained with both NTNG1 and NGL1.

NTN4, NTNG1 and neogenin staining was abundant in MSC cultures: Neogenin receptor staining was observed throughout MSC cultures. In contrast, NTN1 ligand staining was limited, consistent with our gene expression data, while NTN4 staining was more widespread in MSC cultures. NTNG1 staining was high in MSC cultures while staining of the NTNG1-receptor NGL1 was observed to be sparse.

UNC5b and UNC5c stained at intermediate levels in the MSC cultures. Interestingly, neogenin and UNC5c stained fine, long projections within a sub-population of MSC. UNC5b and UNC5c staining was weak in cells that also stained with the MSC phenotypic marker nucleostemin while neogenin staining was not observed in nucleostemin stained cells. When nucleostemin localized to the nucleolus the MSC stained with UNC5b. In contrast, when nucleostemin staining was localized to the cytoplasm the MSC stained with UNC5c. Further work will be required to untangle the significance of nucleolar versus cytoplasmic staining of nucleostemin and UNC5b or UNC5c. NTN4, neogenin, UNC5b, UNC5c, NTNG1 and NGL1 protein expression was confirmed in MSC cultures. In parallel, NTN4 and neogenin proteins were highly expressed in osteoclasts, consistent with our gene data. The soluble form of the NTN4-ligand was observed in MSC culture supernatants. Surprisingly, a soluble fragment of NTNG1, a GPI-linked ligand thought to be non-soluble, was also observed in supernatants derived from MSC cultures.

Figures 2A, 2B, 2C, 2D, 2E, 2F:
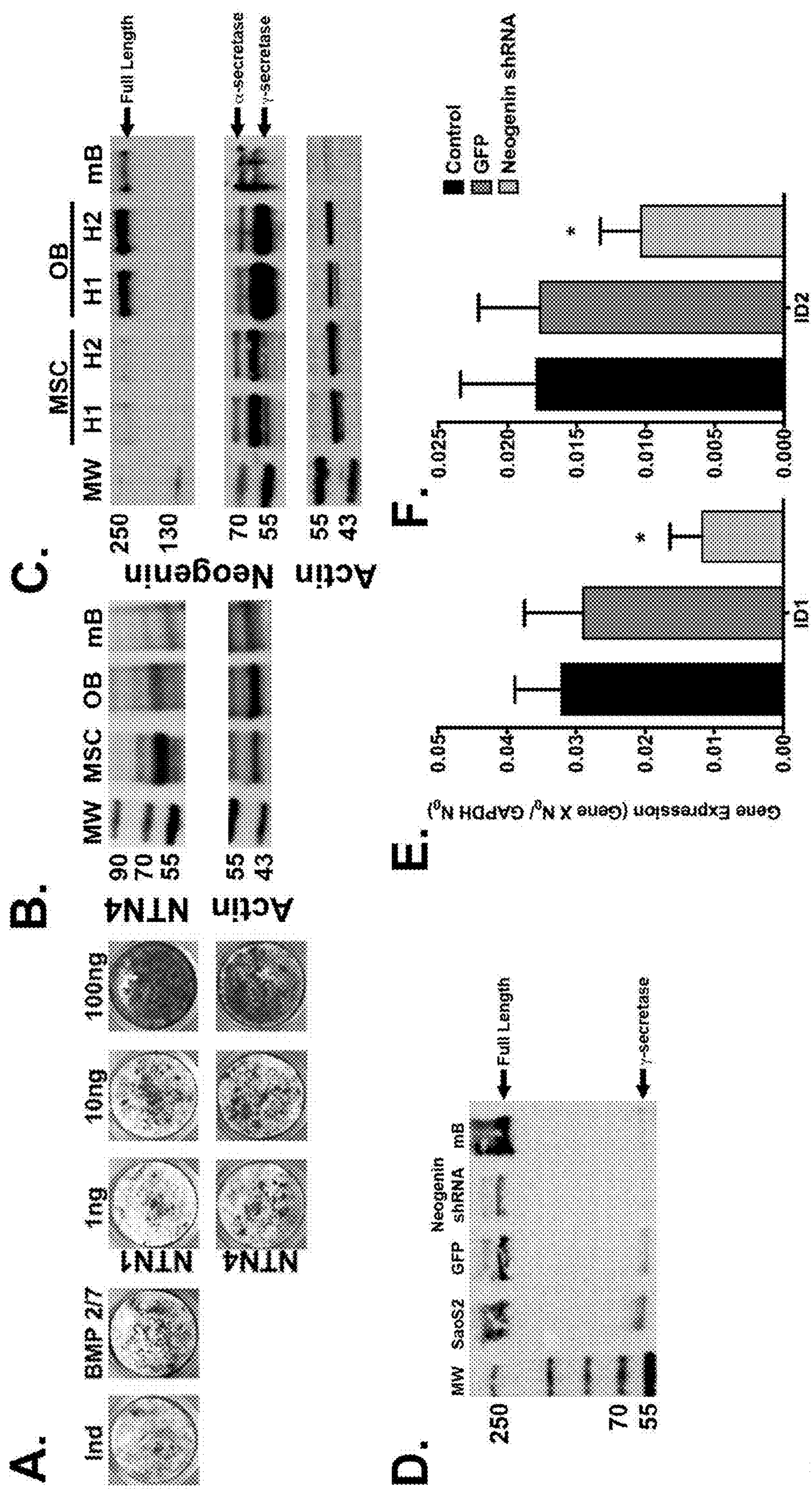
Figures 3A, 3B, 3C, 3D, 3E:
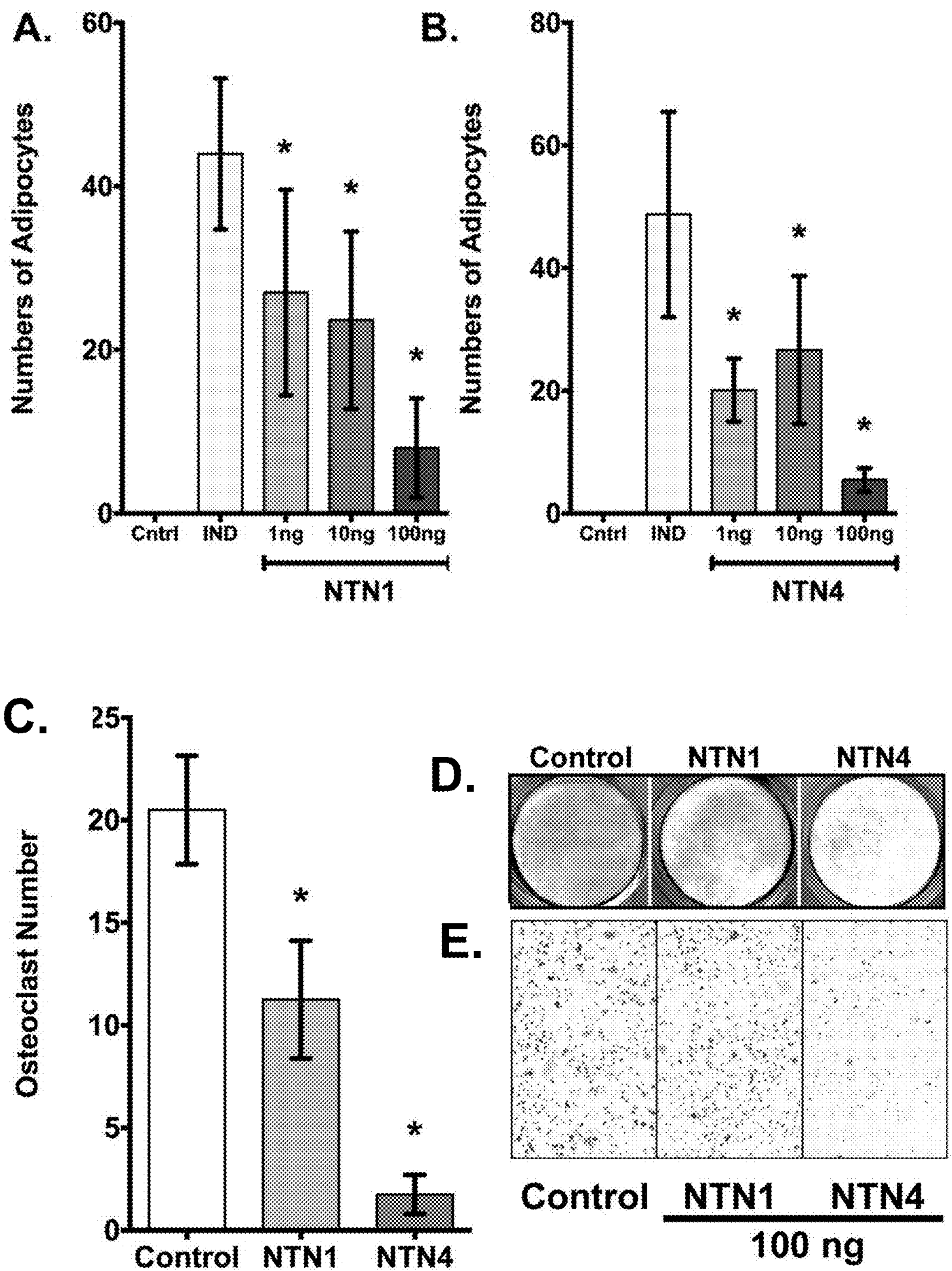
FIGS. 3A-3E.

Nertrin-ligands increase osteogenesis while decreasing adipogenesis and osteoclast formation: The addition of recombinant NTN1 and NTN4 to MSC cultures undergoing osteogenic differentiation resulted in a dose-dependent increase in mineral accumulation, with the largest dose of NTN1 or NTN4 (100-ng) yielding more alizarin red staining compared to BMP2/7 treated cultures. In parallel, osteogenic differentiation resulted in decreased NTN4 protein expression that is consistent with the decrease observed in NTN4 gene expression. The full-length neogenin protein was increased in osteoblast cultures. Goldschneider et al. (Goldschneider et al., 2008) recently described two intracellular fragments of neogenin cleaved by the a- and y-secretase enzymes. Both the α- and γ-secretase fragments were identified in MSC and osteoblasts; however, a significant increase in the neogenin fragment created by γ-secretase (NeoICD) was only observed in osteoblasts. Neogenin-receptor expression was inhibited in SaOS2 cells using a neogenin shRNA lentivirus and confirmed by analyzing protein lysates. Goldschneider et al. proposed that SMAD5 gene expression was a target of the NeoICD. We found that SMAD5 gene expression decreased 44.3% in neogenin deficient SaOS2 cells ($p<0.037$) versus GFP-controls and non-transfected controls. BMP-receptor signaling requires the SMAD1/5/8 complex locate to the nucleus, so we also examined SMAD gene expression. SMAD1 gene expression also decreased 36.6% in the neogenin deficient SaOS2 cells ($p<0.04$) versus controls. (FIG. 2G) We also measured inhibitor SMAD6 decreased 66.3% in neogenin deficient SaOS2 cells ($p<0.0007$) relative controls. The ID transcription factors, ID1 and ID2, are targets of BMP-signaling (Peng et al., 2004). ID1 gene expression was decreased 63.4% ($p<0.001$) while ID2 gene expression was decreased 42.3% ($p<0.039$) in the neogenin deficient SaOS2 cells relative to control cells. We did not identify significant changes in SMAD2, SMAD3, SMAD4, SMAD7 or SMAD8 gene expression. In addition, there was no change in gene expression for the TGFβ-ligands and the TGFβ-receptors. SaOS2 cells induced to make bone mineral were grown in decreasing concentrations of serum. No significant effect was observed in mineral accumulation in GFP-control and non-transfected control SaOS2 cells; however, a dose dependent decrease in mineral formation was observed in neogenin deficient SaOS2 cells versus controls. (FIG. 2J) The addition of BMP2/7 to these cultures restored some mineral accumulation in neogenin deficient SaOS2 cells. In contrast the NTN1- or NTN4-ligands decreased the numbers of adipocytes in a dose-dependent fashion ($p<0.008$). (FIGS. 3A and 3B) FABP4 was strongly expressed in bone marrow cells that also strongly expressed the UNC5c-receptor. UNC5c gene expression was increased in MSC induced to become osteoblasts relative to MSC; as such, we propose that the clusters of bone marrow cells are FABP4+/UNC5c+ cells of the adipocyte lineage. Despite the low levels of netrin-receptor expression, the addition of NTN1 or NTN4 also resulted in a significant decrease in the numbers of osteoclasts in culture ($p<0.0003$). (FIGS. 3C, 3D and 3E) The netrin-ligand mediated decrease in osteoclast number is consistent with the observations made by Enoki et al. (Enoki et al., 2014).

Figures 4A, 4B, 4C, 4D, 4E, 4F, 4G, 4H, 4I:
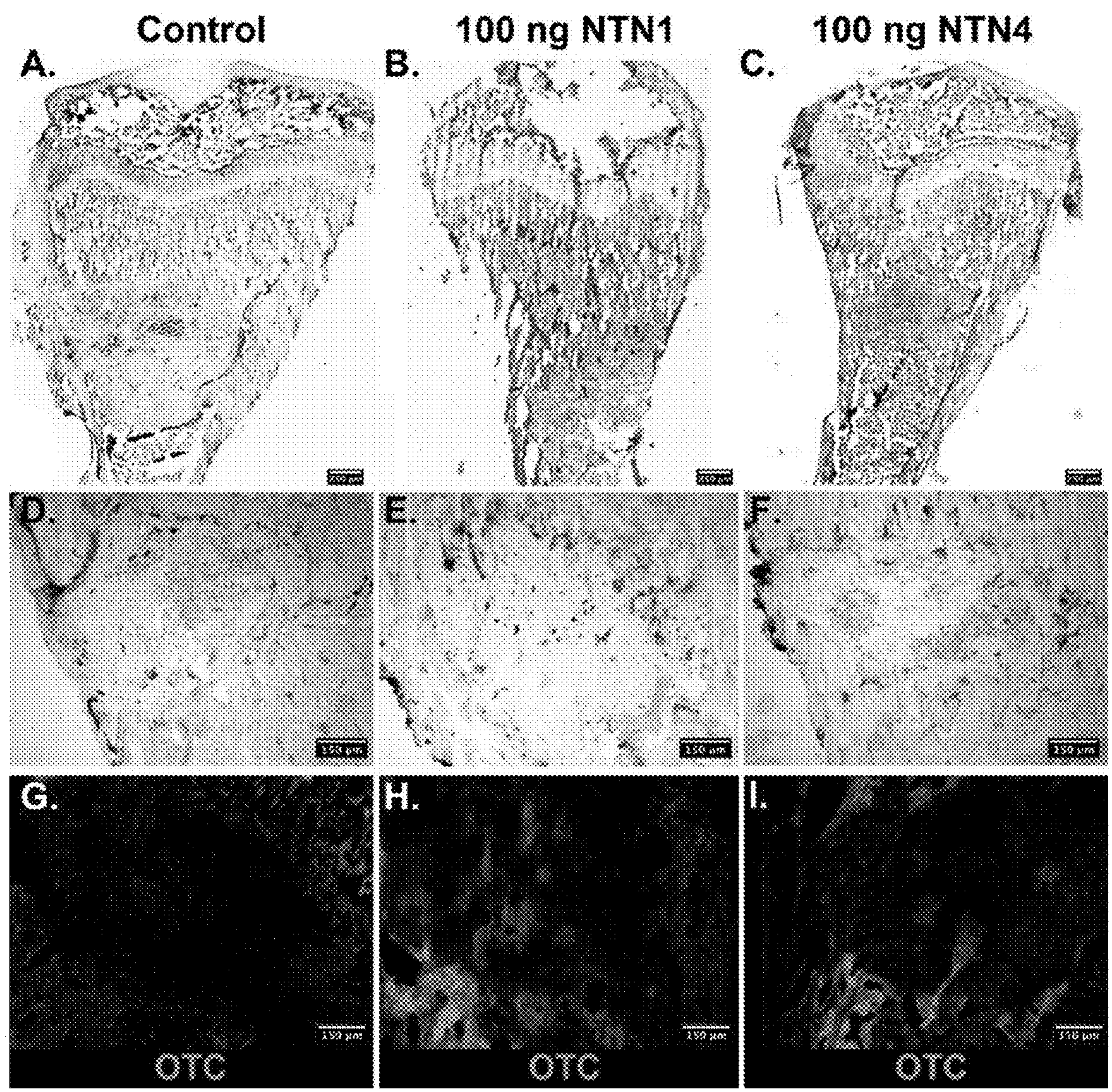
FIGS. 4A-4I: TRAP staining (red) was decreased within the defects of control mice (FIGS. 4A and 4D) corresponding to decreased numbers of osteoclasts in NTN1 (FIGS. 4B and 4E) and NTN4 (FIGS. 4C and 4F) treated tibias. (2×) OTC staining (green) for bone formation within the defect was only observed around the periphery of the defect in control mice (FIG. 4G) while in NTN1 (FIG. 4H) and NTN4 (FIG. 4I) treated mice OTC staining was robust throughout the defect. (20×)
Figures 5A, 5B, 5C, 5D, 5E, 5F, 5G, 5H, 5I, 5J:
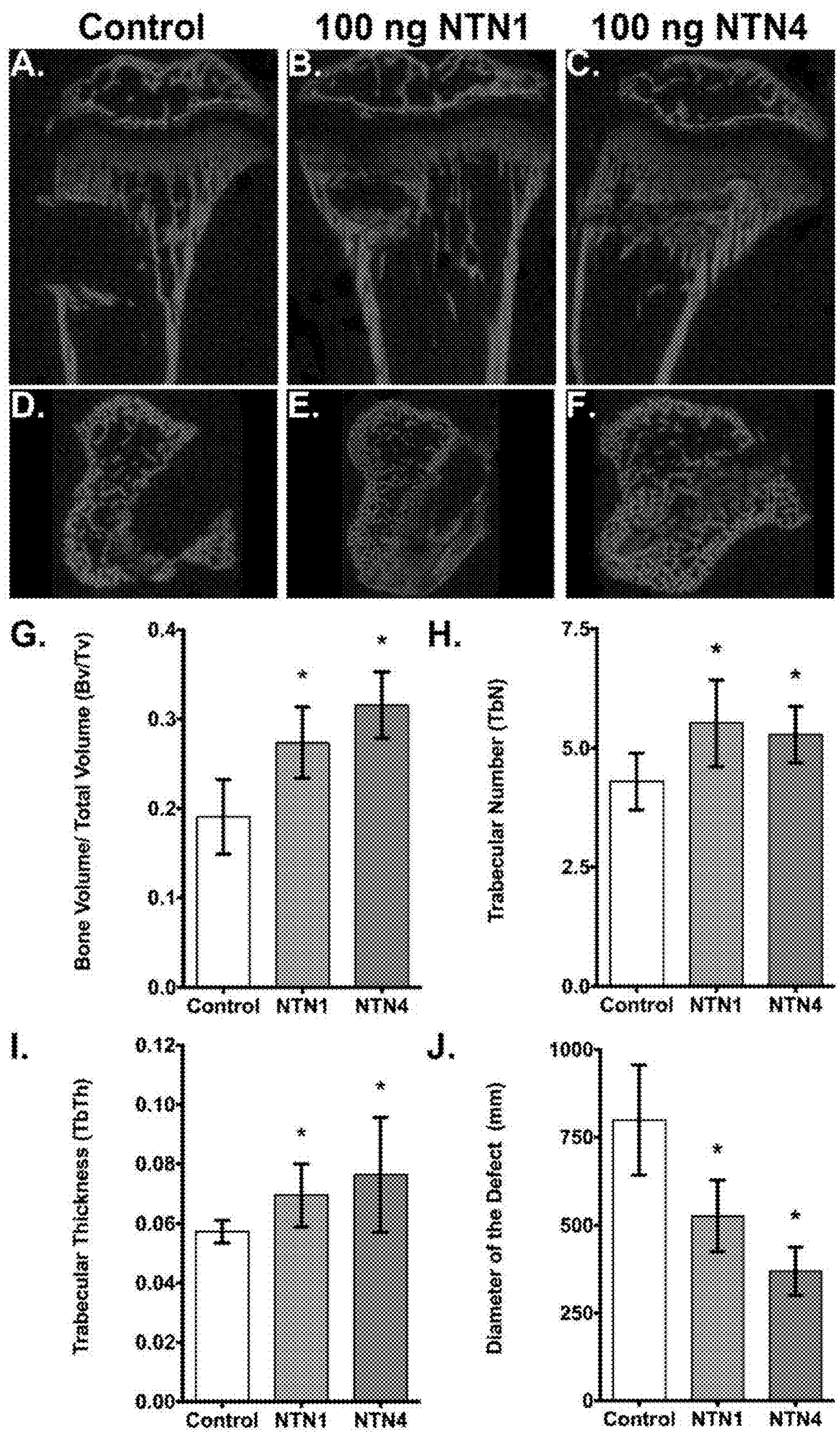
FIGS. 5A-5J: Sagittal and axial μCT images (12-μm voxel depth) from the unicortical defect from control (FIGS. 5A and 5D) and NTN1 (FIGS. 5B and 5E) and NTN4 (FIGS. 5C and 5F) treated mice. The defects were qualitatively smaller in the NTN1 and NTN4 treated mice versus the PBS treated control mice.

The addition of the netrin-ligands increased bone healing in a unicortical defect: Unicortical defects administered surgically were treated with the netrin-ligands. (FIGS. 4A-5J) TRAP stained osteoclasts were observed throughout the control defects. (FIGS. 4A and 4D) However, diminished TRAP staining was observed within the defects treated with NTN1 (FIGS. 4B and 4E) while TRAP staining was not seen in NTN4 treated defects. (FIGS. 4C and 4F) In NTN1 or NTN4 treated defects, abundant TRAP staining was observed on the periphery of the defects. In parallel, OTC staining associated with new bone formation was decreased in control, saline treated defects and was increased within the defects treated with NTN1 or NTN4. (FIGS. 4G, 4H and 4I) Tibias treated with the NTN1- or NTN4-ligands and imaged using μCT were observed to have smaller defects than tibias not treated with ligand. (FIGS. 5A-5F) An analysis of the μCT images demonstrated that treatment with NTN1 or NTN4 resulted in significant increase in bone mass, Bv/Tv ($p<0.0003$). (FIG. 5G) Trabecular number (TbN) and thickness (TbTh) were also significantly increased following the addition of NTN1 or NTN4 ($p<0.04$). (FIGS. 5H and 5I) Further, an analysis of the defect diameter showed that NTN1 or NTN4 resulted in a significant decrease in the diameter when compared to saline treated controls ($p<0.0085$). (FIG. 5J)

EXAMPLE 2

The RGMa and RGMb-Ligands Inhibit Bone Formation while Promoting Bone Re-Absorption Methods: Human bone marrow was collected from consenting adult patients undergoing either an elective primary proximal femoral total hip arthroplasty or elective primary distal femoral total knee arthroplasty (n=6, mean age 65) as a part of an IRB approved study. Human MSC were derived from the adherent fraction of whole bone marrow aspirates. Monocytes were derived from the non-adherent fraction of bone marrow and enriched through a separate sub-culture using 100-ng/mL recombinant human macrophage colony-stimulating factor (MCSF; Wyeth). In parallel experiments described below, the femurs from 3-week (n=10) and 16-week (n=20) old male mice were collected and then the bone marrow was flushed from the femur according to the following: A 21-gauge needle was inserted into the femoral intramedular canal after the removal of the proximal and distal ends of the femur. Media was then carefully passed through the proximal end of the femur, which forced the bone marrow to pass out of the bone. Finally, the bone marrow pellet was mechanically disassociated using an 18-gauge needle and then passed through a 70-μm mesh filter. These whole bone marrow aspirates were used to generate osteoclasts. Cells were maintained in Dulbecco's Modification of Eagle's Media (DMEM) containing 10% fetal calf serum (v/v) and 1% penicillin-streptomycin-glutamine (PSG; Cellgro, Mediatech). Recombinant human RGM-ligands (RGMa and RGMb) were diluted in PBS (R&D Systems). The responsible IACUC committee approved all animal studies described in this work.

Gene Expression Analysis: MSC, osteoblasts and adipocytes derived from human bone marrow were assayed for changes in gene expression. In parallel, osteoclasts derived from human monocytes were also assayed for changes in myeloid gene expression. Gene data were derived from two independently generated samples collected from at least three patients. mRNA was purified using RNeasy Plus Mini columns (Qiagen) and cDNA was synthesized using the iScript cDNA Synthesis Kit (Bio-Rad). Gene expression was analyzed using quantitative PCR (qPCR) using 100-ng of cDNA mixed with Fast Plus EvaGreen Master Mix (Biotium). In each experiment GAPDH served as a control, negative controls contained no-template and a standard curve was generated using serial dilutions of a chemically synthesized sequence for GAPDH (0, 1, 10 and 100 femtograms; Integrated DNA Technologies). Gene expression was evaluated using Pfaffl's method, in which the efficiency of each primer (E) and the starting gene product concentration (No) are calculated from the linear region of the fluorescence-crossing threshold curve using the software LinRegPCR (v2013.0). Experiments were considered valid when the control gene GAPDH fell within the standard curve and the primer efficiencies (E) were calculated to be E>=1.8. The presence of a single gene product was confirmed using a melt-curve analysis and product size was confirmed using gene product gel-electrophoresis.

Protein Expression through Western Blot Analysis: Human MSC, osteoblasts and osteoclasts were lysed with cold RIPA buffer (Pierce Thermo Scientific) containing 2-mM iodoacetamide, 2-mM benzamidine hydrochloride, 0.1-mM ethylmaleimide, 1% PMSF and the Halt Protease Inhibitor Cocktail (Pierce Thermo Scientific). Protein was also assayed from supernatant samples derived from MSC cultures. Protein lysates were analyzed from at least two replicates generated from three patient samples. Total protein was assayed using the BCA Protein Assay Kit (Thermo) following the manufacturers instructions. Samples were loaded (20-μg/well) onto a 10-20% Mini-Protean Tris-Tricine Precast Gel (Bio-Rad) with the Page Ruler Pre-stained NIR Protein Ladder (Bio-Rad) and transferred to a nitrocellulose membrane (Bio-Rad). Primary antibodies (Santa Cruz Biotechnologies) directed against RGMa (1:500) and RGMb (1:500) were identified on membranes blocked using 5% non-fat milk. Vinculin (1:500) or actin (1:500) served as loading controls. Antibodies were detected using an HRP-conjugated micro-polymer conjugated secondary antibody (ImmPress kit, Vector Labs) in conjunction with the Clarity Western ECL substrate (Bio-Rad). Mouse brain protein lysates (mB) were used as positive-expression controls.

Immunofluorescence and Morphology: Tibias from 3-week (n=10) and 16-week (n=20) old mice were fixed in 2% paraformaldehyde, simultaneously decalcified and cryo-protected using a solution of 15% EDTA and 30% sucrose, and then snap-frozen using liquid nitrogen and sectioned at 8-μm using a cryo-microtome (Leica 3050). Patterns in ligand and receptor expression were identified using the following primary antibodies: RGMa (1:250), RGMb (1:250), neogenin (1:250) and FABP4 (1:250). Antibodies were detected using Alexa Fluor-488 or -568 secondary antibodies (1:500; Invitrogen). MSC were also grown on glass discs and fixed with 2% paraformaldehyde. MSC were incubated with primary antibodies against RGMa (1:250), RGMb (1:250) and nucleostemin (1:250) Antibodies were detected using Alexa Fluor-488 or -568 antibodies (1:500; Invitrogen). Nuclei were counter-stained with 10-μg/ml 4',6-diamidino-2-phenylindole (DAPI, Sigma).

Osteogenesis: Osteogenic potential in MSC was assayed by chemically inducing mineral formation. MSC from at least three human patients were seeded at $5\times10^3$ cells per well and allowed to become confluent and woven prior to the addition of osteo-induction media. Induction media consisted of DMEM containing 20% FCS (v/v) and 1% PSG supplemented with 25-μg/mL of acscorbic-2-phosphate (Sigma), 100-nM dexamethasone (Sigma) and the following dosing regimen of β-glycerophosphate (BGP; Sigma): 1× media change with 5-mM BGP, 1× media change with 10-mM BGP and 1× media change with 20-mM of BGP. RGM-ligands (1-, 10- and 100-ng) were added at each post-induction media change. Positive control wells were treated with 25-ng of the recombinant human BMP2/BMP7-ligand (R&D Systems) with the first addition of induction media. After the appearance of mineral nodules, cells were fixed with 70% ice-cold EtOH (Sigma) and then stained using 40-mM alizarin red-S (pH 4.2, Sigma). Osteogenesis experiments were repeated at least twice for each patient.

Adipogenesis: Adipogenic potential in MSC was assayed by chemically inducing adipocyte differentiation and lipid accumulation. MSC from at least three human patient samples were seeded at $5\times10^3$ cells per well and allowed to become confluent prior to the addition of adipo-induction media. Induction media consisted of DMEM containing 10% FCS (v/v) and 1% PSG supplemented with 5-μM rosiglitizone (Caymen Chemical), 500-μM 3-isobutyl-1-methylxanthine (IBMX; Sigma), 1-μM dexamethasone (Sigma) and 1-μg/mL recombinant human insulin (rinsulin, Sheffield Bio-Science). Induction media including the RGM-ligands (1-, 10- and 100-ng) was added to cultures at each media change; 2× media changes over a 7-day post-induction period. Cultures were fixed with 2% paraformaldehyde and imaged with the lipophilic fluorescent stain nile red (excitation at 488-nm; Sigma). Nuclei were counter-stained with DAPI. Estimates of adipocytes numbers were obtained through Cavalieri sampling in conjunction with a modification of the fractionator technique used in un-biased stereology, in which a particular well was divided into parallel sections that served as counting regions. Adipogenesis experiments were repeated at least twice.

TRAP Staining and the Assay of Osteoclast Number: Osteoclasts were derived from either an enriched population of human monocytes or from mouse non-enriched whole bone marrow aspirates. Three human patient bone marrow samples were assayed in parallel with samples collected from 3-week (n=10) and 16-week (n=20) mouse bone marrow. The monocyte fraction was stimulated to become osteoclasts by culturing $1\times10^6$ cells with 25-ng/mL of MCSF and 25-ng/mL of recombinant human or mouse RANK-ligand (R&D Systems) in the presence of the RGMa- or RGMb-ligands (100-ng). Osteoclasts were stained with tartrate resistant acid phosphatase (TRAP; Sigma Leukocyte Acid Phosphatase Kit 387-A) and counted when cells stained TRAP-positive and had at least three nuclei. Estimates of osteoclast number were obtained by Cavalieri sampling and a modification of the fractionator technique.

Unicortical Defect Model: Male 3-week old C57BL/6 mice (n=5 per treatment group) were injected with one of the RGM-ligands (RGMa or RGMb) following the creation of a unicortical defect. Briefly, a small incision (approximately 3-mm) was made just below the knee joint, located on the medial side of the tibia just below the tibial tuberosity on the tibial crest. In young animals the physeal plate is clearly visible and the drill bit was placed approximately 1-mm below this point. The drill-bit produces a unicortical defect with dimensions 300-μm diameter x 1-mm depth. A Hamilton Neuros RN 10-4 syringe with a 33-gauge blunt tip needle was used to inject the RGM-ligands (RGMa or RGMb at 100-ng in 2-μL) directly into the unicortical defect at a rate no faster than approximately 0.1-4 per second. The left-limb tibias served as contra-lateral surgical controls, in which animals received a unicortical defect and 2-4 of saline was injected. These same mice were injected with oxytetracycline (50-μg/kg; OTC) administered intraperitoneally to measure bone apposition 48-hours prior to euthanasia. Mice were euthanized 5-days after surgery, hind limbs were collected and tibias were fixed for immunofluorescense, TRAP staining and OTC associated bone growth.

MicroCT Analysis of Unicortical Defects: High-resolution images of the tibia were acquired with a μCT imaging system (μCT40; Scanco Medical). Tibias were scanned at 45-keV with an isotropic voxel size of 12-μm. An analysis region was selected from axial sections to include the entire unicortical defect bounded by the endosteal cortical wall. The volume corrected bone volume (bone volume/total volume; Bv/Tv), trabecular number (TbN) and trabecular thickness (TbTh) were calculated using the Scanco software. The maximum diameter of the defect was determined using unbiased stereology, in which the maximum linear distance was measured between opposing sides of the defect through serial sections. The maximum diameter was determined using the BoneJ plug-in for ImageJ (NIH Research Services Branch; http://rsbweb.nih.gov/ij/).

Statistical Analyses: Prism statistical software (Graphpad) was used to analyze data. Means and standard deviations were calculated. Data were analyzed by 1-way or 2-way ANOVA using the Holm-Sidak post-hoc correction for multiple comparisons with significance set at $p<0.05$.

Figures 6A, 6B, 6C, 6D, 6E, 6F:
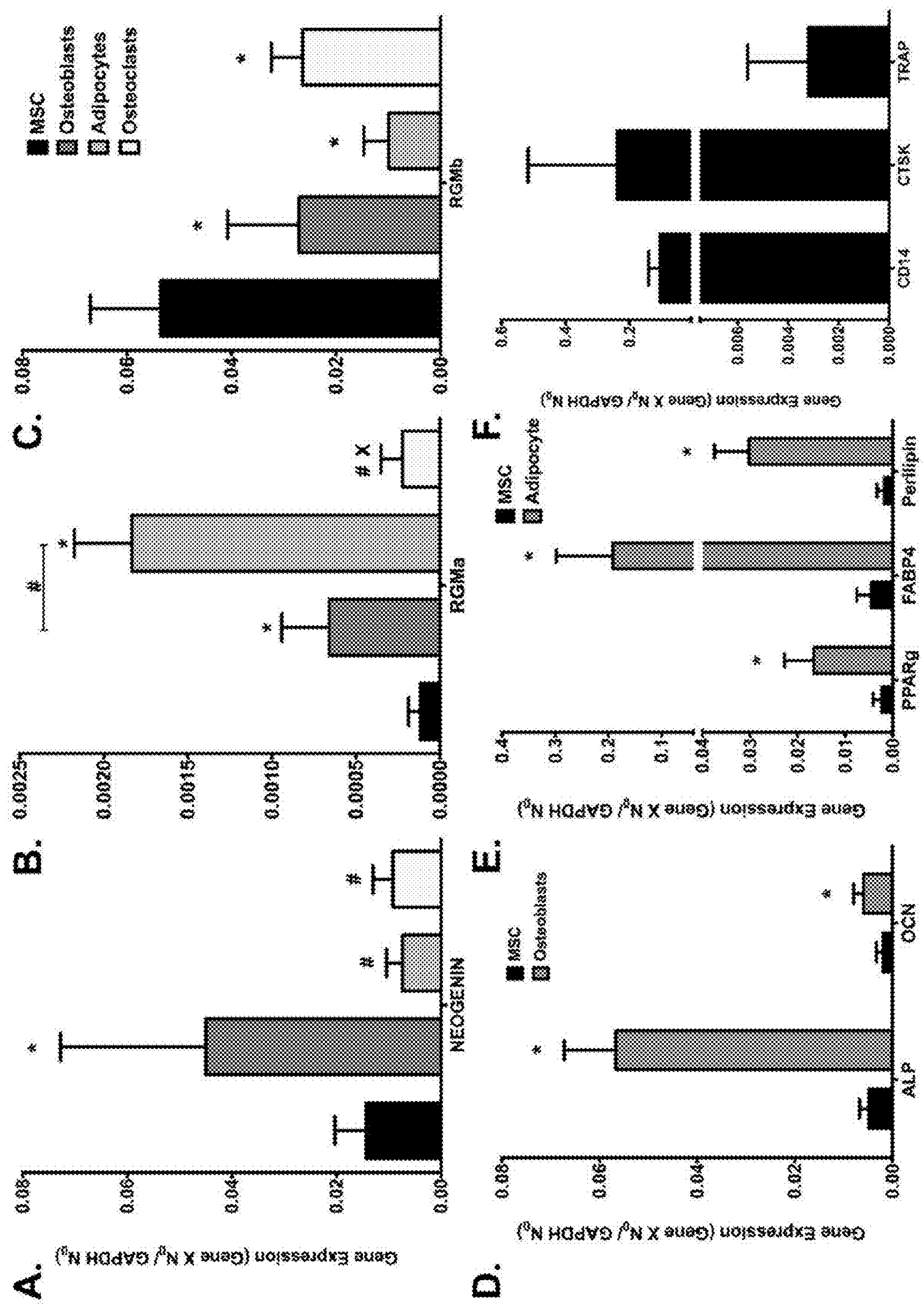
FIGS. 6A-6F.

Results:

The RGM-ligands and the neogenin receptor were expressed in mesenchymal lineage cells and osteoclasts. Neogenin gene expression was increased in cultures induced to become osteoblasts compared to MSC ($p<0.028$) and decreased in adipocyte and osteoclast cultures when compared to osteoblasts ($p<0.016$). (FIG. 6A) RGMa gene expression was increased in osteoblasts when compared to MSC cultures ($p<0.005$) and was further increased in cultures induced to become adipocytes when compared to osteoblasts ($p<0.0001$). (FIG. 6B) Conversely, RGMb gene expression was decreased in cultures of osteoblasts ($p<0.0035$), adipocytes ($p<0.0005$) and osteoclasts ($p<0.0035$) when compared to MSC. (FIG. 6C) RGMc gene expression was identified in MSC and osteoblasts; however, RGMc expression did not change after the addition of osteo-induction media. RGMc gene expression was never observed in adipocytes or osteoclasts. Lineage specific gene expression was confirmed in osteoblasts, adipocytes and osteoclasts. Alkaline phosphatase (ALP) and osteocalcin (OCN) gene expression increased in osteoblasts compared to MSC ($p<0.049$). (FIG. 6D) PPARg, fatty acid binding protein (FABP4) and perilipin increased in adipocytes versus MSC cultures ($p<0.005$). (FIG. 6E) CD14, cathepsin K (CSTK) and TRAP gene expression were observed in osteoclasts. (FIG. 6F) The full-length RGMa protein and the cleaved, soluble RGMa protein fragments were expressed in MSC lysates. RGMb protein expression was observed to be robust in MSC cultures. The cleaved, soluble RGMb protein fragment was also identified in protein derived from supernatants collected from MSC cultures. The difference in protein size between the full-length RMGa/RGMb and the cleaved, soluble fragments were both approximately 17-kD. RGMa could not be detected in osteoclasts RGMb protein expression was robust.

RGM-ligands localized with neogenin-receptor stained tissue. Neogenin receptor staining was observed throughout the growth plate, with increased staining observed in the more differentiated chondrocytes of the hypertrophic zone versus the less differentiated chondrocytes of the reserve and proliferative zones. In addition, neogenin staining was robust in the bone adjacent to the growth plate in parallel with tomato lectin staining, the latter of which is a marker of myeloid lineage cells. RGMa staining was only weakly expressed adjacent to the growth plate. RGMb staining was observed in the chondrocytes of the reserve and the hypertrophic zones. In addition, RGMb staining was intense in the region of the metaphysis adjacent to the growth plate, consistent with the high levels of expression observed in MSC that are abundant near chondro-osseous junction of the growth plate. Neogenin staining was observed within the bone marrow and was highly expressed in osteoblasts lining the endosteal surface. In addition, neogenin staining was observed within the periosteal layer, within adjacent muscle tissue and within the osteocytes (arrows) located in cortical bone. RGMa staining was observed in osteoblasts lining the endosteal surface and within the bone marrow. RGMb staining was observed within the singular cells within the bone marrow and in the osteoblasts lining the endosteal surface. RGMa staining was only rarely observed in cultured MSC (arrows) while neogenin staining was ubiquitous throughout MSC cultures. RGMb staining was observed in cultured MSC that also stained positive for neogenin. RGMb staining was also observed in cultured MSC that stained with nucleostemin, which is a phenotypic marker for MSC; however, RGMa could not be detected in MSC that stained with nucleostemin. Consistent with our gene expression data, the RGMb staining was greater in nucleostemin stained MSC than the RGMb staining observed in neogenin stained cells.

Figures 7A, 7B, 7C:
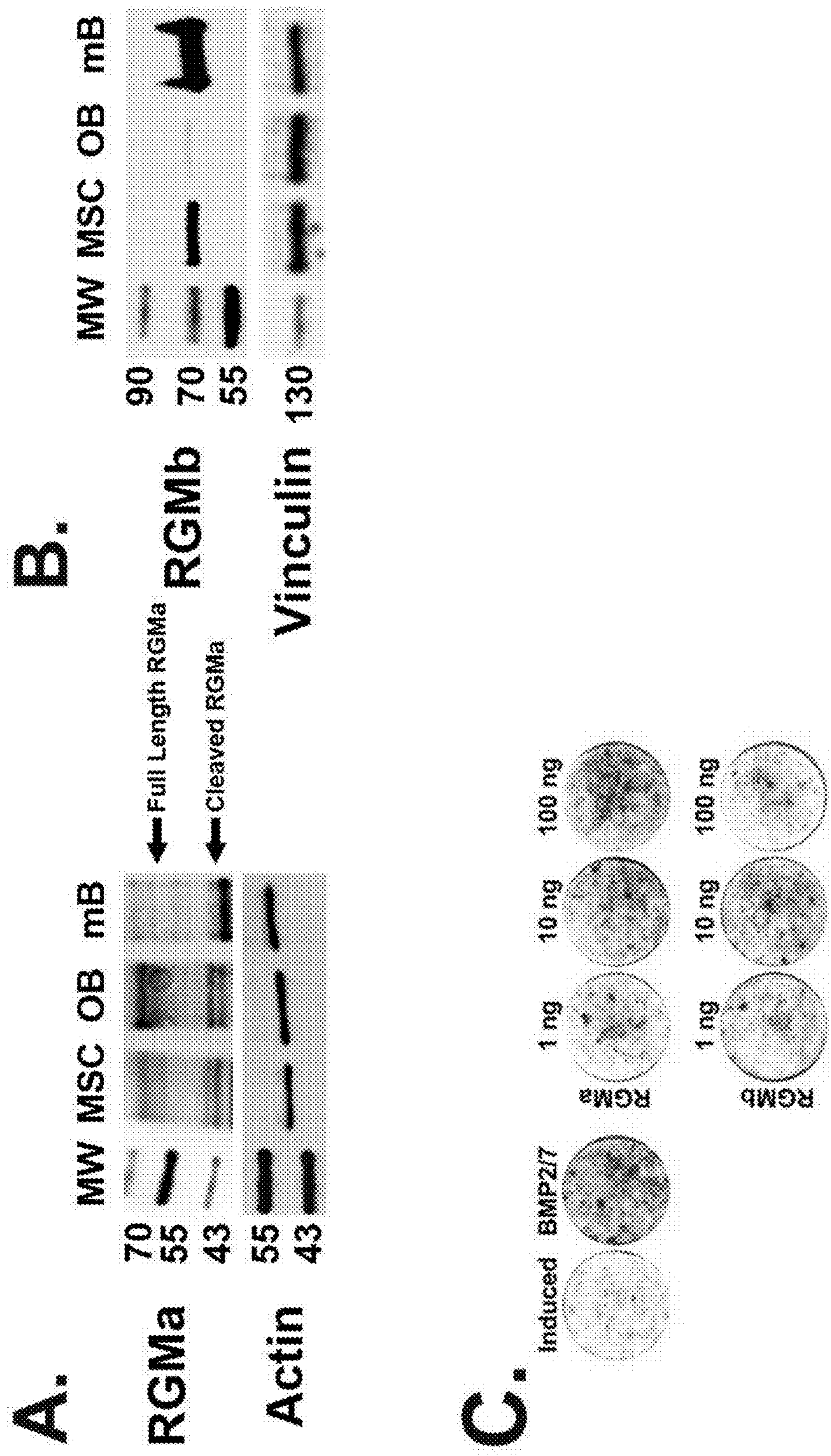
FIGS. 7A-7C.

The addition of the RGM-ligands to MSC cultures altered mineral accumulation in culture. The addition of osteoblast induction media to MSC cultures resulted in an increase in the expression of the full-length RGMa protein while no change was observed in the expression of the cleaved, soluble RGMa fragment. (FIG. 7A) In contrast, RGMb protein expression decreased in osteoblast cultures when compared to MSC cultures. (FIG. 7B) The cleaved, soluble fragment observed in MSC culture supernatants could not be detected in osteoblast cultures. The addition of the RGMa-ligand to cultured MSC induced to become osteoblasts produced a slight dose-dependent increase in mineral formation. (FIG. 7C) However, the effects of the RGMa-ligand on mineral formation were not greater than treatment with BMP2/7. In contrast, the administration of the RGMb-ligand failed to increase mineral formation in osteoblasts. (FIG. 7C)

Figures 8A, 8B, 8C, 8D, 8E:
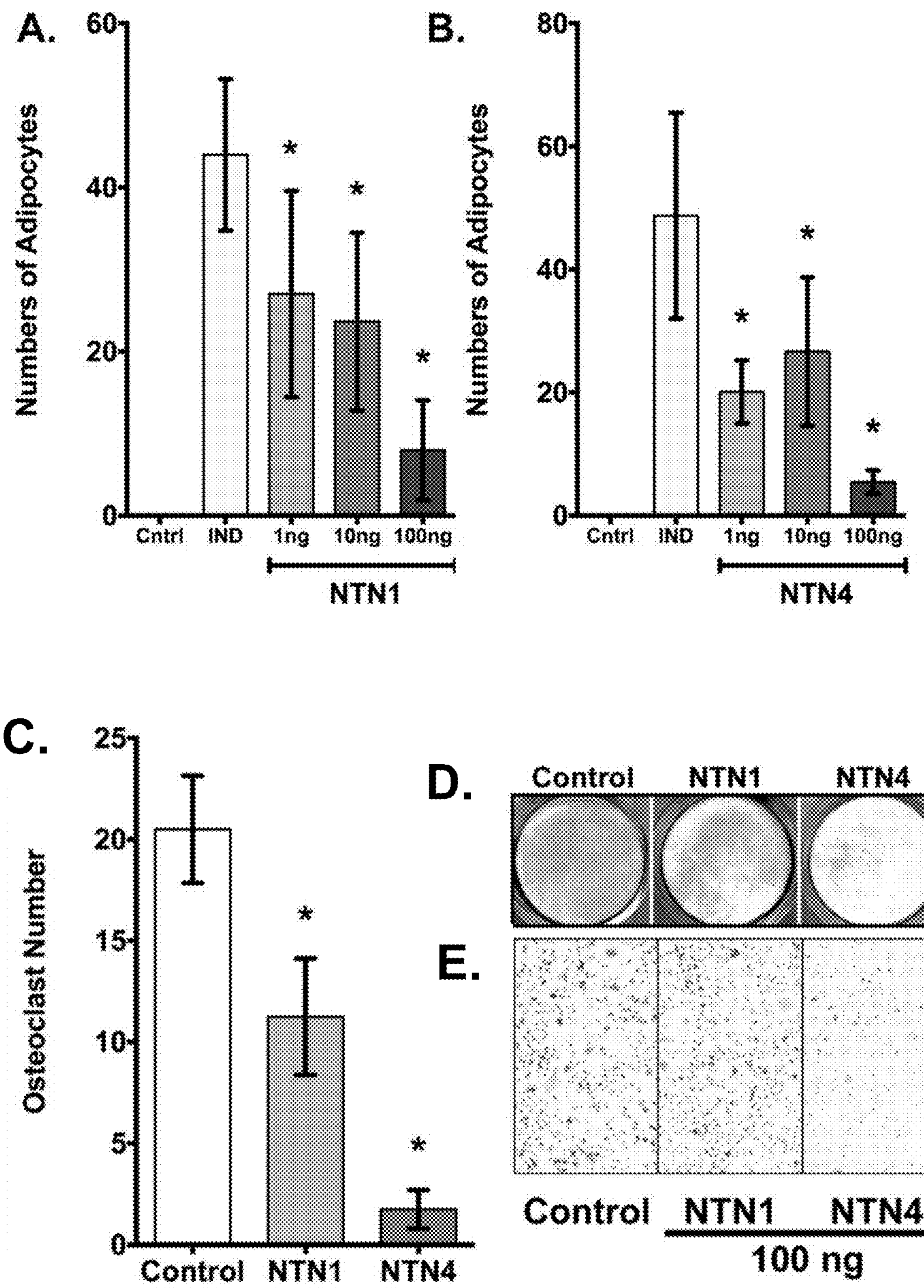
FIGS. 8A-8E.

The RGM-ligands increased adipocyte and osteoclast numbers in culture. The addition of the RGMa-ligand to MSC cultures resulted in a significant, 2-fold increase in the numbers of adipocytes ($p<0.0004$), independent of dose. (FIG. 8A) The RGMb-ligand also produced a significant, 2.5-fold increase in the numbers of adipocytes ($p<0.0037$) when added to MSC cultures. (FIG. 8B) RGMa gene expression was greatest in adipocytes and RGMa staining was observed to localize in clusters of cells within the bone marrow. An analysis of these regions with the adipocyte marker FABP4 demonstrated that RGMa staining localized to these FABP4 staining regions within the bone marrow. FABP4 was also observed to stain vascular endothelial cells. In monocytes cultured to become osteoclasts the addition of the RGMa-ligand resulted in a significant 1.72-fold increase in the numbers of osteoclasts ($p<0.002$). (FIGS. 8C-8E) Further, the addition of the RGMb-ligand also produced a significant, 1.55-fold increase in osteoclast numbers in culture ($p<0.007$).

Figures 9A, 9B, 9C, 9D, 9E, 9F, 9G:
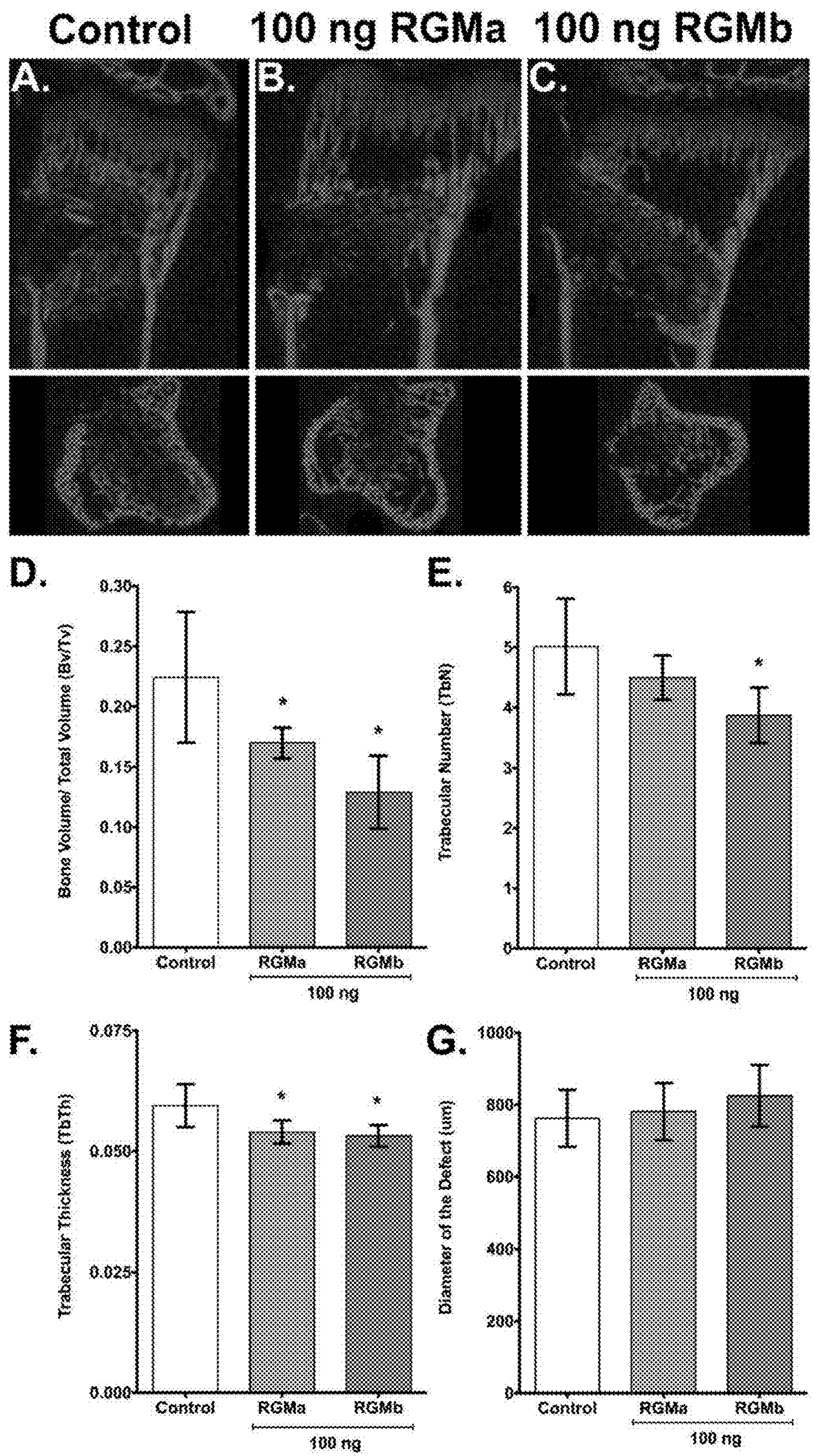
FIGS. 9A-9G.
Figures 10A, 10B, 10C, 10D, 10E, 10F, 10G, 10H, 10I, 10J, 10K, 10L:
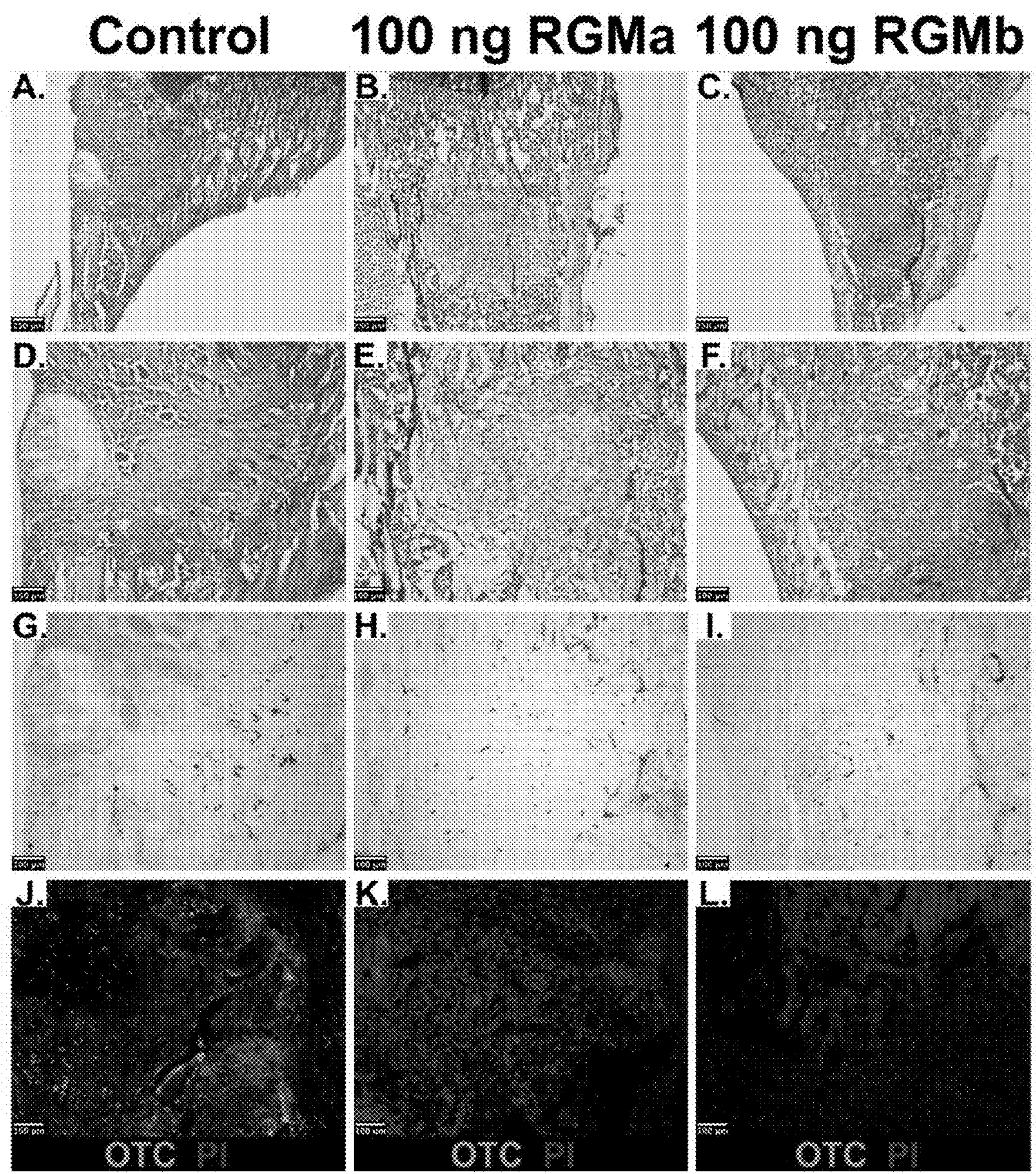
FIGS. 10A-10L: TRAP staining of the defects demonstrated that very few osteoclasts (red staining) were observed within the control, PBS treated defects (FIGS. 10A-10I). Although osteoclasts were observed surrounding the control defects. In contrast, increased numbers of osteoclasts (red staining) were observed within defects treated with the RGMa- or RGMb-ligands (FIGS. 10H and 10I). TRAP stained tissue was counter-stained with methyl green and imaged at 4× (FIGS. 10A-10C; scale bar=250-μm) or at 20× (FIGS. 10D-10F; scale bar=100-μm).

RGM-ligands decreased bone healing when added to a unicortical defect. The addition of RGMa to unicortical defects resulted in a significant decrease in bone volume within the defect (Bv/Tv) ($p<0.033$). (FIG. 9A) In parallel, treatment with the RGMb-ligand resulted in a significant decrease in Bv/Tv within the unicortical defects ($p<0.002$). (FIG. 9A) The decrease in Bv/Tv following the addition of RGMb corresponded with a significant decrease in trabecular number (TbN) ($p<0.01$). (FIG. 9B) Both the addition of RGMa ($p<0.014$) and RGMb ($p<0.012$) resulted in a significant decrease in trabecular thickness (TbTh). (FIG. 9C) The diameter of the defect was also measured; however, no significant difference was observed in the defect diameter when animals were treated with either of the two RGM-ligands. (FIG. 9D) TRAP staining revealed an increase in the numbers of osteoclasts in the unicortical defects treated with either RGMa or RGMb. (FIG. 10A-10I) Specifically, TRAP staining was not observed within the control group unicortical defects while TRAP staining was observed throughout the defects in RGMa or RMGb treated mice. (FIG. 10G, 10H and 10I) In parallel, OTC staining for mineral apposition was significant within the unicortical defects from the control groups. (FIG. 10J) Unicortical defects treated with RGMa or RGMb had very little OTC staining, suggesting reduced new bone growth occurring within the defect. (FIG. 10K and 10L)

EXAMPLE 3

The Slit1- and Slit2-Ligands Increased Bone Formation while Dlit3 Increased Bone Re-Absorption Methods: Human bone marrow was collected from consenting adult patients undergoing either an elective primary proximal femoral total hip arthroplasty or elective primary distal femoral total knee arthroplasty (n=6, mean age 65) as a part of an IRB approved study. Human MSC were derived from the adherent fraction of whole bone marrow aspirates. Monocytes were derived from the non-adherent fraction of bone marrow and enriched through a separate sub-culture using 100-ng/mL recombinant human macrophage colony-stimulating factor (MCSF; Wyeth). In parallel experiments described below, the femurs from 3-week (n=10) and 16-week (n=20) old male mice were collected and then the bone marrow was flushed from the femur according to the following: A 21-gauge needle was inserted into the femoral intramedular canal after the removal of the proximal and distal ends of the femur. Media was then carefully passed through the proximal end of the femur, which forced the bone marrow to pass out of the bone. Finally, the bone marrow pellet was mechanically disassociated using an 18-gauge needle and then passed through a 70-μm mesh filter. These whole bone marrow aspirates were used to generate osteoclasts. Cells were maintained in Dulbecco's Modification of Eagle's Media (DMEM) containing 10% fetal calf serum (v/v) and 1% penicillin-streptomycin-glutamine (PSG; Cellgro, Mediatech). Recombinant human slit-ligands (slit1, slit2 or slit3) were diluted in PBS (R&D Systems). The responsible IACUC committee approved all animal studies described in this work.

Gene Expression Analysis: MSC, osteoblasts and adipocytes derived from human bone marrow were assayed for changes in gene expression. In parallel, osteoclasts derived from human monocytes were also assayed for changes in myeloid gene expression. Gene data were derived from two independently generated samples collected from at least three patients. mRNA was purified using RNeasy Plus Mini columns (Qiagen) and cDNA was synthesized using the iScript cDNA Synthesis Kit (Bio-Rad). Gene expression was analyzed using quantitative PCR (qPCR) using 100-ng of cDNA mixed with Fast Plus EvaGreen Master Mix (Biotium). In each experiment GAPDH served as a control, negative controls contained no-template and a standard curve was generated using serial dilutions of a chemically synthesized sequence for GAPDH (0, 1, 10 and 100 femtograms; Integrated DNA Technologies). Gene expression was evaluated using Pfaffl's method, in which the efficiency of each primer (E) and the starting gene product concentration ($N_0$) are calculated from the linear region of the fluorescence-crossing threshold curve using the software LinRegPCR (v2013.0). Experiments were considered valid when the control gene GAPDH fell within the standard curve and the primer efficiencies (E) were calculated to be E>=1.8. The presence of a single gene product was confirmed using a melt-curve analysis and product size was confirmed using gene product gel-electrophoresis.

Protein Expression through Western Blot Analysis: Human MSC, osteoblasts and osteoclasts were lysed with cold RIPA buffer (Pierce Thermo Scientific) containing 2-mM iodoacetamide, 2-mM benzamidine hydrochloride, 0.1-mM ethylmaleimide, 1% PMSF and the Halt Protease Inhibitor Cocktail (Pierce Thermo Scientific). Protein was also assayed from supernatant samples derived from MSC cultures. Protein lysates were analyzed from at least two replicates generated from three patient samples. Total protein was assayed using the BCA Protein Assay Kit (Thermo) following the manufacturers instructions. Samples were loaded (20-μg/well) onto a 10-20% Mini-Protean Tris-Tricine Precast Gel (Bio-Rad) with the Page Ruler Pre-stained NIR Protein Ladder (Bio-Rad) and transferred to a nitrocellulose membrane (Bio-Rad). Primary antibodies (Santa Cruz Biotechnologies) directed against slit1 (1:500), slit2 (1:500), slit3 (1:500), ROBO1 or ROBO4 were identified on membranes blocked using 5% non-fat milk. Vinculin (1:500) or actin (1:500) served as loading controls. Antibodies were detected using an HRP-conjugated micro-polymer conjugated secondary antibody (ImmPress kit, Vector Labs) in conjunction with the Clarity Western ECL substrate (Bio-Rad). Mouse brain protein lysates (mB) were used as positive-expression controls.

Immunofluorescence and Morphology: Tibias from 3-week (n=10) and 16-week (n=20) old mice were fixed in 2% paraformaldehyde, simultaneously decalcified and cryoprotected using a solution of 15% EDTA and 30% sucrose, and then snap-frozen using liquid nitrogen and sectioned at 8-μm using a cryo-microtome (Leica 3050). Patterns in ligand and receptor expression were identified using the following primary antibodies: slit1 (1:250), slit2 (1:250), slit3 (1:250), ROBO1 (1:500), ROBO2 (1:500), ROBO4 (1:500) and FABP4 (1:250). Antibodies were detected using Alexa Fluor-488 or -568 secondary antibodies (1:500; Invitrogen). MSC were also grown on glass discs and fixed with 2% paraformaldehyde. MSC were incubated with primary antibodies against slit1 (1:250), slit2 (1:250), slit3 (1:250), ROBO1 (1:250), ROBO4 (1:250) and nucleostemin (1:250) Antibodies were detected using Alexa Fluor-488 or -568 antibodies (1:500; Invitrogen). Nuclei were counter-stained with 10-μg/ml 4',6-diamidino-2-phenylindole (DAPI, Sigma).

Osteogenesis: Osteogenic potential in MSC was assayed by chemically inducing mineral formation. MSC from at least three human patients were seeded at $5\times10^3$ cells per well and allowed to become confluent and woven prior to the addition of osteo-induction media. Induction media consisted of DMEM containing 20% FCS (v/v) and 1% PSG supplemented with 25-μg/mL of acscorbic-2-phosphate (Sigma), 100-nM dexamethasone (Sigma) and the following dosing regimen of β-glycerophosphate (BGP; Sigma): 1× media change with 5-mM BGP, 1× media change with 10-mM BGP and 1× media change with 20-mM of BGP. Slit-ligands (1-, 10- and 100-ng) were added at each post-induction media change. Positive control wells were treated with 25-ng of the recombinant human BMP2/BMP7-ligand (R&D Systems) with the first addition of induction media. After the appearance of mineral nodules, cells were fixed with 70% ice-cold EtOH (Sigma) and then stained using 40-mM alizarin red-S (pH 4.2, Sigma). Osteogenesis experiments were repeated at least twice for each patient.

Adipogenesis: Adipogenic potential in MSC was assayed by chemically inducing adipocyte differentiation and lipid accumulation. MSC from at least three human patient samples were seeded at $5\times10^3$ cells per well and allowed to become confluent prior to the addition of adipo-induction media. Induction media consisted of DMEM containing 10% FCS (v/v) and 1% PSG supplemented with 5-μM rosiglitizone (Caymen Chemical), 500-μM 3-isobutyl-1-methylxanthine (IBMX; Sigma), 1-μM dexamethasone (Sigma) and 1-μg/mL recombinant human insulin (rinsulin, Sheffield Bio-Science). Induction media including the slit-ligands (1-, 10- and 100-ng) was added to cultures at each media change; 2× media changes over a 7-day post-induction period. Cultures were fixed with 2% paraformaldehyde and imaged with the lipophilic fluorescent stain nile red (excitation at 488-nm; Sigma). Nuclei were counter-stained with DAPI. Estimates of adipocytes numbers were obtained through Cavalieri sampling in conjunction with a modification of the fractionator technique used in un-biased stereology, in which a particular well was divided into parallel sections that served as counting regions. Adipogenesis experiments were repeated at least twice.

TRAP Staining and the Assay of Osteoclast Number: Osteoclasts were derived from either an enriched population of human monocytes or from mouse non-enriched whole bone marrow aspirates. Three human patient bone marrow samples were assayed in parallel with samples collected from 3-week (n=10) and 16-week (n=20) mouse bone marrow. The monocyte fraction was stimulated to become osteoclasts by culturing $1\times10^6$ cells with 25-ng/mL of MCSF and 25-ng/mL of recombinant human or mouse RANK-ligand (R&D Systems) in the presence of the slit1-, slit2- or slit3-ligands (100-ng). Osteoclasts were stained with tartrate resistant acid phosphatase (TRAP; Sigma Leukocyte Acid Phosphatase Kit 387-A) and counted when cells stained TRAP-positive and had at least three nuclei. Estimates of osteoclast number were obtained by Cavalieri sampling and a modification of the fractionator technique.

Unicortical Defect Model: Male 3-week old C57BLJ6 mice (n=5 per treatment group) were injected with one of the slit-ligands (slit1, slit2 or slit3) following the creation of a unicortical defect. Briefly, a small incision (approximately 3-mm) was made just below the knee joint, located on the medial side of the tibia just below the tibial tuberosity on the tibial crest. In young animals the physeal plate is clearly visible and the drill bit was placed approximately 1-mm below this point. The drill-bit produces a unicortical defect with dimensions 300-μm diameter×1-mm depth. A Hamilton Neuros RN 10-4 syringe with a 33-gauge blunt tip needle was used to inject the slit-ligands (slit1, slit2 or slit3 at 100-ng in 2-4) directly into the unicortical defect at a rate no faster than approximately 0.1-4 per second. The left-limb tibias served as contra-lateral surgical controls, in which animals received a unicortical defect and 2-4 of saline was injected. These same mice were injected with oxytetracycline (50-μg/kg; OTC) administered intraperitoneally to measure bone apposition 48-hours prior to euthanasia. Mice were euthanized 5-days after surgery, hind limbs were collected and tibias were fixed for immunofluorescense, TRAP staining and OTC associated bone growth.

MicroCT Analysis of Unicortical Defects: High-resolution images of the tibia were acquired with a μCT imaging system (μCT40; Scanco Medical). Tibias were scanned at 45-keV with an isotropic voxel size of 12-μm. An analysis region was selected from axial sections to include the entire unicortical defect bounded by the endosteal cortical wall. The volume corrected bone volume (bone volume/total volume; Bv/Tv), trabecular number (TbN) and trabecular thickness (TbTh) were calculated using the Scanco software. The maximum diameter of the defect was determined using unbiased stereology, in which the maximum linear distance was measured between opposing sides of the defect through serial sections. The maximum diameter was determined using the BoneJ plug-in for ImageJ (NIH Research Services Branch;

Statistical Analyses: Prism statistical software (Graphpad) was used to analyze data. Means and standard deviations were calculated. Data were analyzed by 1-way or 2-way ANOVA using the Holm-Sidak post-hoc correction for multiple comparisons with significance set at $p<0.05$.

Figures 11A, 11B, 11C, 11D, 11E, 11F:
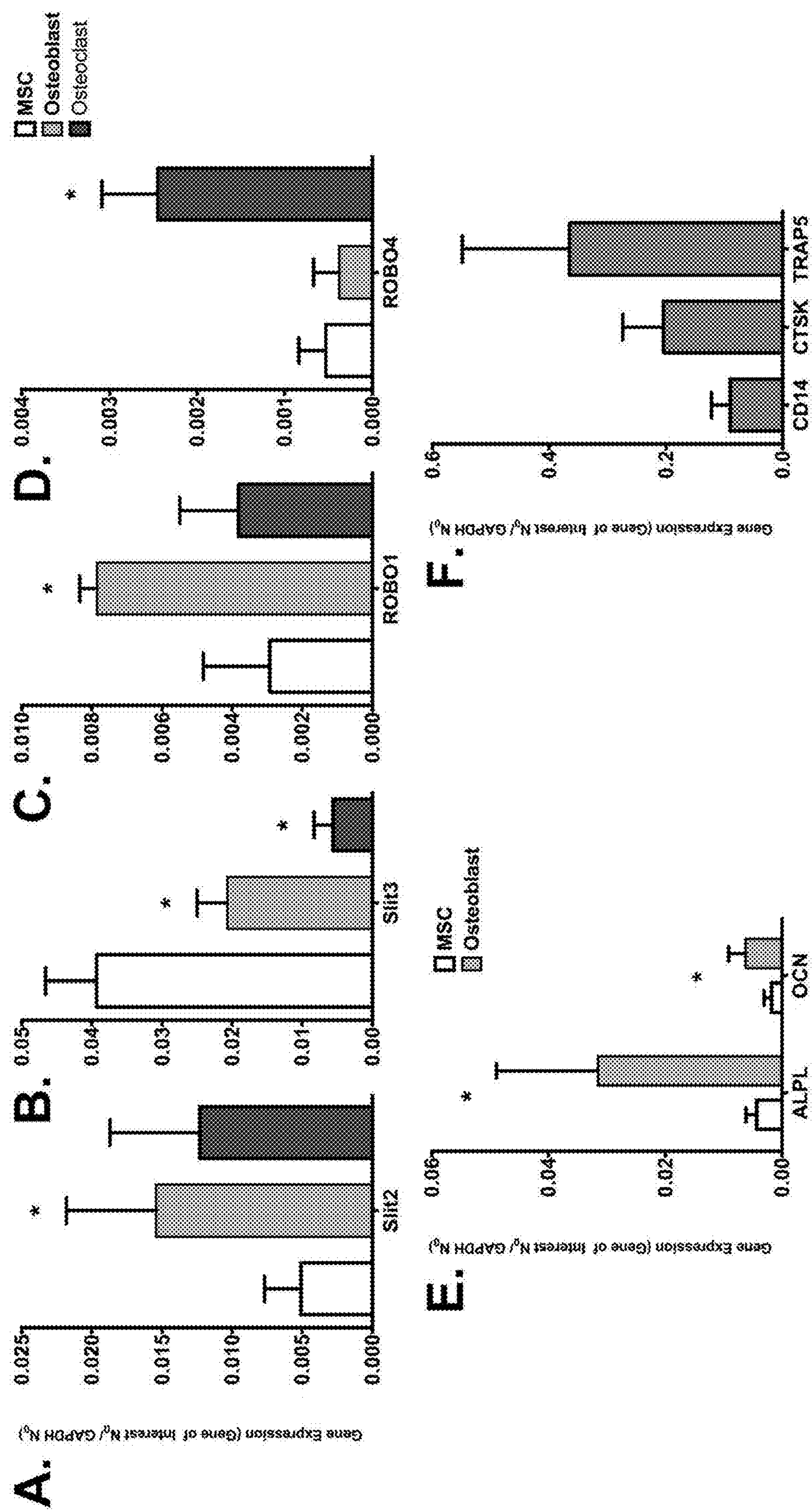
FIGS. 11A-11F.

Results:

The slit-ligands and the ROBO-receptors were seen in MSC and myeloid lineage cells. Slit2 gene expression was increased in osteoblasts ($p<0.021$) while slit3 gene expression was decreased in osteoblasts ($p<0.002$) and osteoclasts ($p<0.001$). (FIGS. 11A and 11B) The ROBO1 receptor gene expression increased significantly in osteoblasts relative to MSC ($p<0.018$) while ROBO2 gene expression was only observed in osteoblasts. (FIG. 11C) The ROBO4 receptor gene expression was increased significantly in osteoclasts relative to osteoblasts and MSC ($p<0.005$). (FIG. 11D) Alkaline phosphatase (ALP) and osteocalcin (OCN) gene expression increased in osteoblasts compared to MSC ($p<0.01$ and $p<0.015$, respectively). (FIG. 11E) CD14, cathepsin K (CSTK) and TRAP gene expression were observed in osteoclasts. (FIG. 11F) Slit3 expression was confirmed using immunochemistry, which showed slit3 expression was abundant in the bone marrow and within the cortical bone. The ROBO1-receptor stained was observed in the osteoblasts of the endosteal layer, consistent with gene data.

Figures 12A, 12B, 12C, 12D:
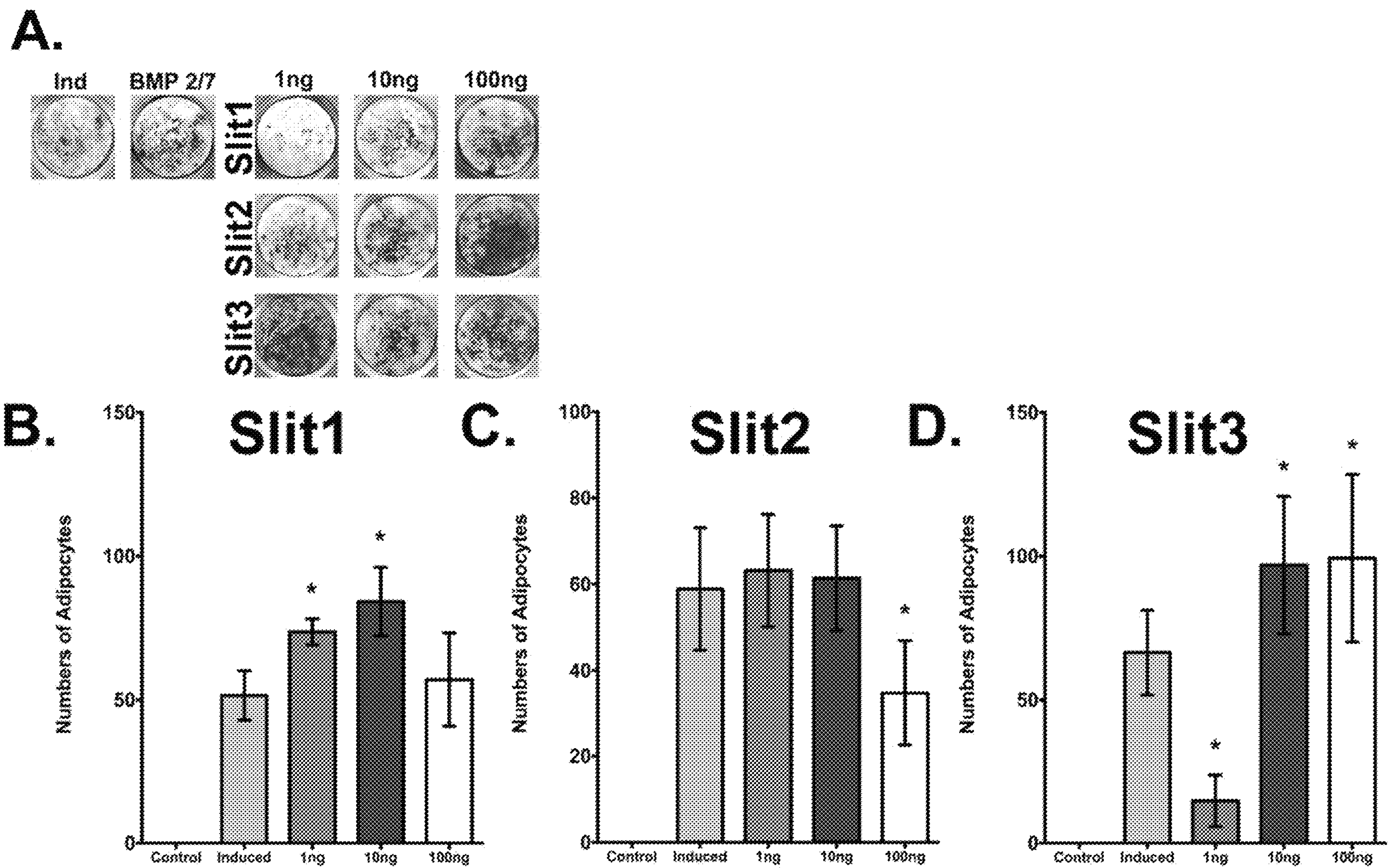
FIGS. 12A-12G.
Figure 12E:
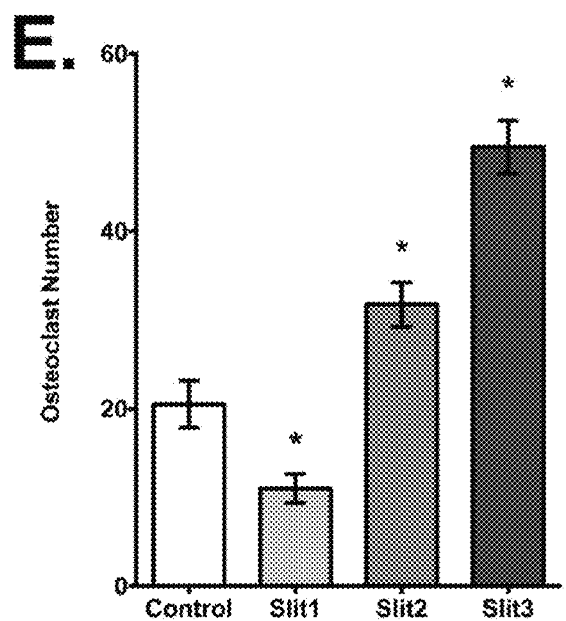
Figure 12F:
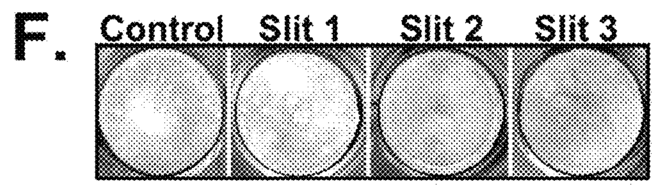
Figure 12G:
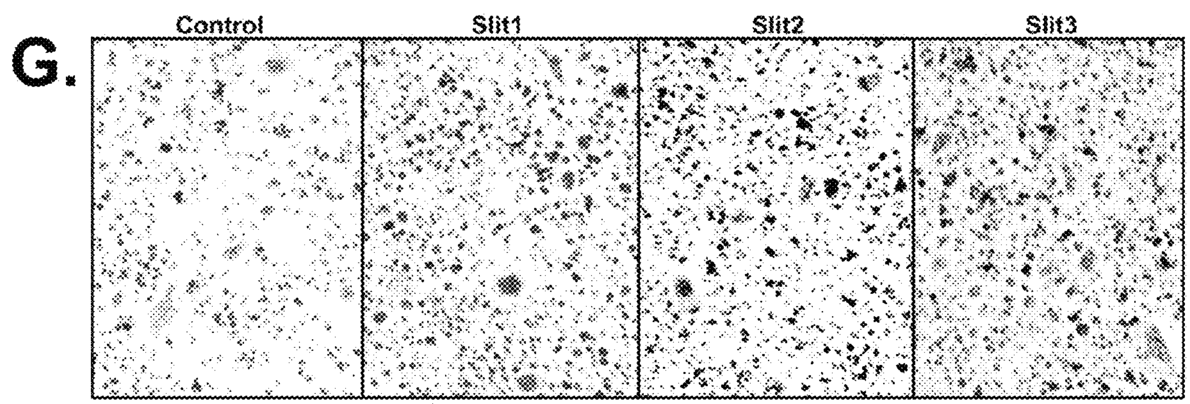

Slit1 and Slit2 increased mineral formation and increased adipocyte number while slit1 suppressed osteoclast number. The addition of slit1 or slit2 to MSC cultures induced to become osteoblasts increased mineral formation in culture while slit3 appeared to inhibit mineral accumulation at the 100-ng ligand dose. (FIG. 12A) Interestingly, the addition of slit1, slit2 or slit3 increased the numbers of adipocytes; however, the increase in adipocyte (fat cell) number observed was not dose dependent. (FIG. 12B-12D) Specifically, the 1- and 10-ng doses of slit1 increased adipocyte number ($p<0.015$) while the 100-ng dose of slit2 decreased adipocyte number ($p<0.012$). The addition of 1-ng of slit3 decreased adipocyte number (p<0.0.001) while the 10- and 100-ng doses increased adipocyte number ($p<0.015$). When slit1 was added to monocyte cultures induced to become osteoclasts, the numbers of osteoclasts was decreased substantially relative to non-treated controls ($p<0.0002$). (FIG. 12E-12G) In contrast, the addition of slit2 or slit3 resulted in an increase in the numbers of osteoclasts relative to the control non-treated cultures ($p<0.0001$). (FIG. 12E-12G)

Figures 13A, 13B, 13C:
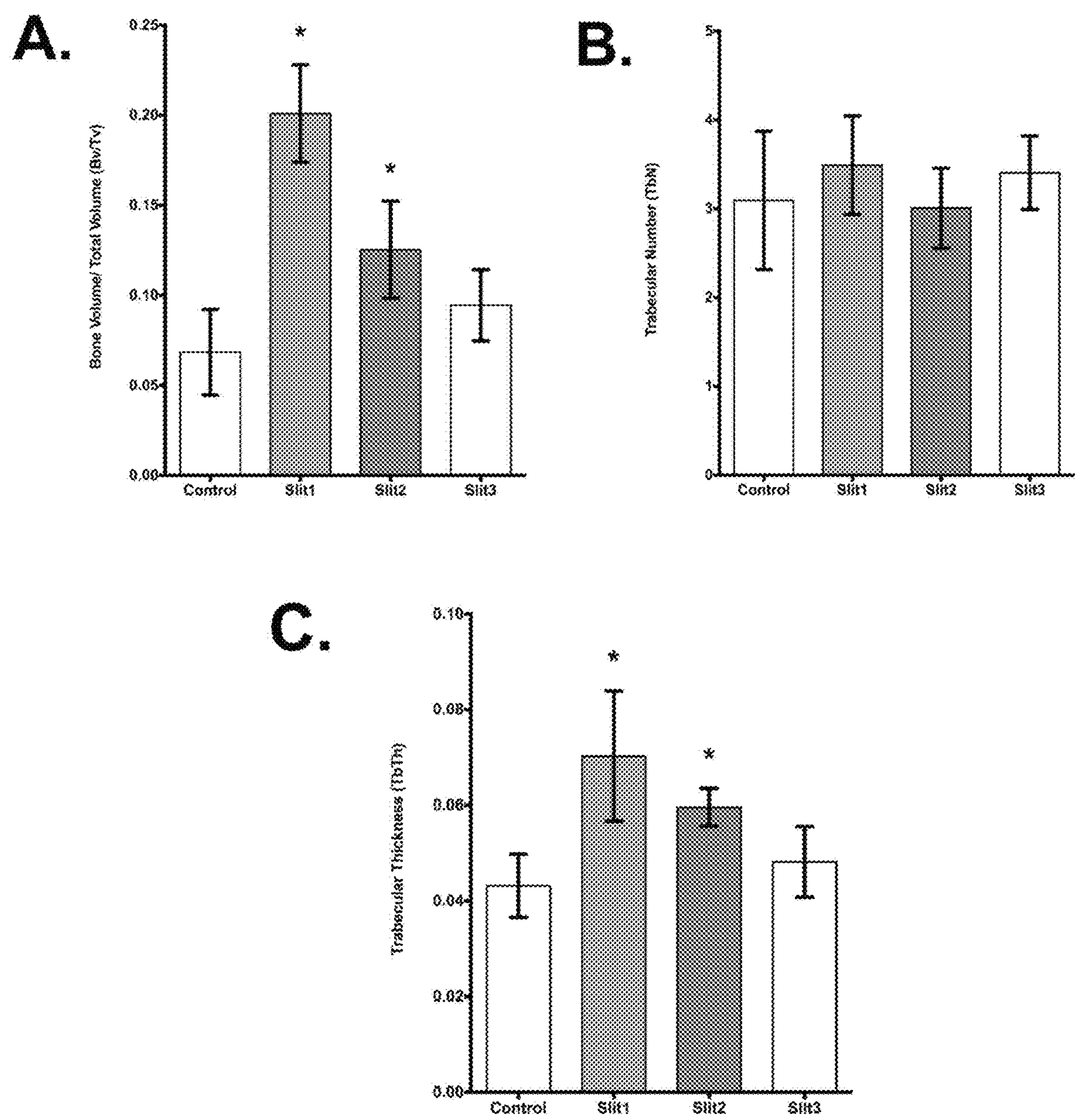
FIGS. 13A-13C.

Slit1 and slit2 increased bone healing and bone formation in a unicortical defect. Unicortical defects treated with the slit1 or slit2-ligand had substantially more bone within the defect 5-days after surgery compared to PBS treated contralateral controls. Bv/Tv (bone volume) within the defect increased 2.8-fold in mice treated with slit1 ($p<0.001$) and increased 74.2% in mice treated with slit2 ($p<0.0003$). (FIG. 13A) Slit3 had no effect on bone healing. In addition, there was no effect from the slit-ligands on trabecular number. (FIG. 13B) However, the addition of slit1 or slit to the defect increased trabecular thickness ($p<0.0015$ while the addition of the slit3-ligand had no effect. (FIG. 13C)

EXAMPLE 4

The Netrin-, RGM- and Slit-Ligands do not Stimulate Sarcoma Tumor Proliferation Despite Possessing the Neogenin-, UNC5 and ROBO-Receptors.

Methods: Human bone marrow was collected from consenting adult patients undergoing either an elective primary proximal femoral total hip arthroplasty or elective primary distal femoral total knee arthroplasty (n=6, mean age 65) as a part of an IRB approved study. Human MSC were derived from the adherent fraction of whole bone marrow aspirates. Ewing's sarcoma tumor cells (RDES, Hs822 and Hs863) and SaOS2 osteosarcoma tumor cells were obtained from ATCC. Cells were maintained in Dulbecco's Modification of Eagle's Media (DMEM) containing 10% fetal calf serum (v/v) and 1% penicillin-streptomycin-glutamine (PSG; Cellgro, Mediatech). Recombinant human netrin-ligands (netrin-1 or netrin-4), RGM-ligands (RGMa or RGMb) or slit-ligands (slit1, slit2 or slit3) were diluted in PBS (R&D Systems).

Gene Expression Analysis: MSC, osteoblasts and adipocytes derived from human bone marrow were assayed for changes in gene expression. In parallel, osteoclasts derived from human monocytes were also assayed for changes in myeloid gene expression. Gene data were derived from two independently generated samples collected from at least three patients. mRNA was purified using RNeasy Plus Mini columns (Qiagen) and cDNA was synthesized using the iScript cDNA Synthesis Kit (Bio-Rad). Gene expression was analyzed using quantitative PCR (qPCR) using 100-ng of cDNA mixed with Fast Plus EvaGreen Master Mix (Biotium). In each experiment GAPDH served as a control, negative controls contained no-template and a standard curve was generated using serial dilutions of a chemically synthesized sequence for GAPDH (0, 1, 10 and 100 femtograms; Integrated DNA Technologies). Gene expression was evaluated using Pfaffl's method, in which the efficiency of each primer (E) and the starting gene product concentration (No) are calculated from the linear region of the fluorescence-crossing threshold curve using the software LinRegPCR (v2013.0). Experiments were considered valid when the control gene GAPDH fell within the standard curve and the primer efficiencies (E) were calculated to be E>=1.8. The presence of a single gene product was confirmed using a melt-curve analysis and product size was confirmed using gene product gel-electrophoresis.

Immunofluorescence and Morphology: Archival sarcoma tumor biopsy samples (n=7) were stained for the neogenin-, UNC5b-, NGL1-, ROBO1- and ROBO4-receptors (1:100) in an IRB approved study. Antibodies were detected using an HRP-conjugated micro-polymer conjugated secondary antibody (ImmPress kit, Vector Labs) in conjunction with the ImmPACT NovaRed peroxidase substrate chromogen (Vector Labs). Sections were counter-stained with 2%-methyl green.

Assay of Cell Number: Following the addition of one of the nterin-, RGM- or slit-ligands, viable cell number was determined with the MTT assay. To each well, 100-ng of netrin-1, netrin-4, RGMa, RGMb, slit1, slit2, or slit3 was administered. After 72-hours, MTT (5 mg/ml (w/v), Sigma) was added to each well, incubated for 2-hours, after which the cells lysed with 500-μl of DMSO (Sigma). MTT was measured at 570-nm and the effects of therapy on cell proliferation were determined by normalizing treated wells relative to mean values from non-treated wells: Fold change in cell number=100* [treated cells optical density/mean control optical density].

Statistical Analyses: Prism statistical software (Graphpad) was used to analyze data. Means and standard deviations were calculated. Data were analyzed by 1-way or 2-way ANOVA using the Holm-Sidak post-hoc correction for multiple comparisons with significance set at $p<0.05$.

Figures 14A, 14B, 14C, 14D, 14E, 14F:
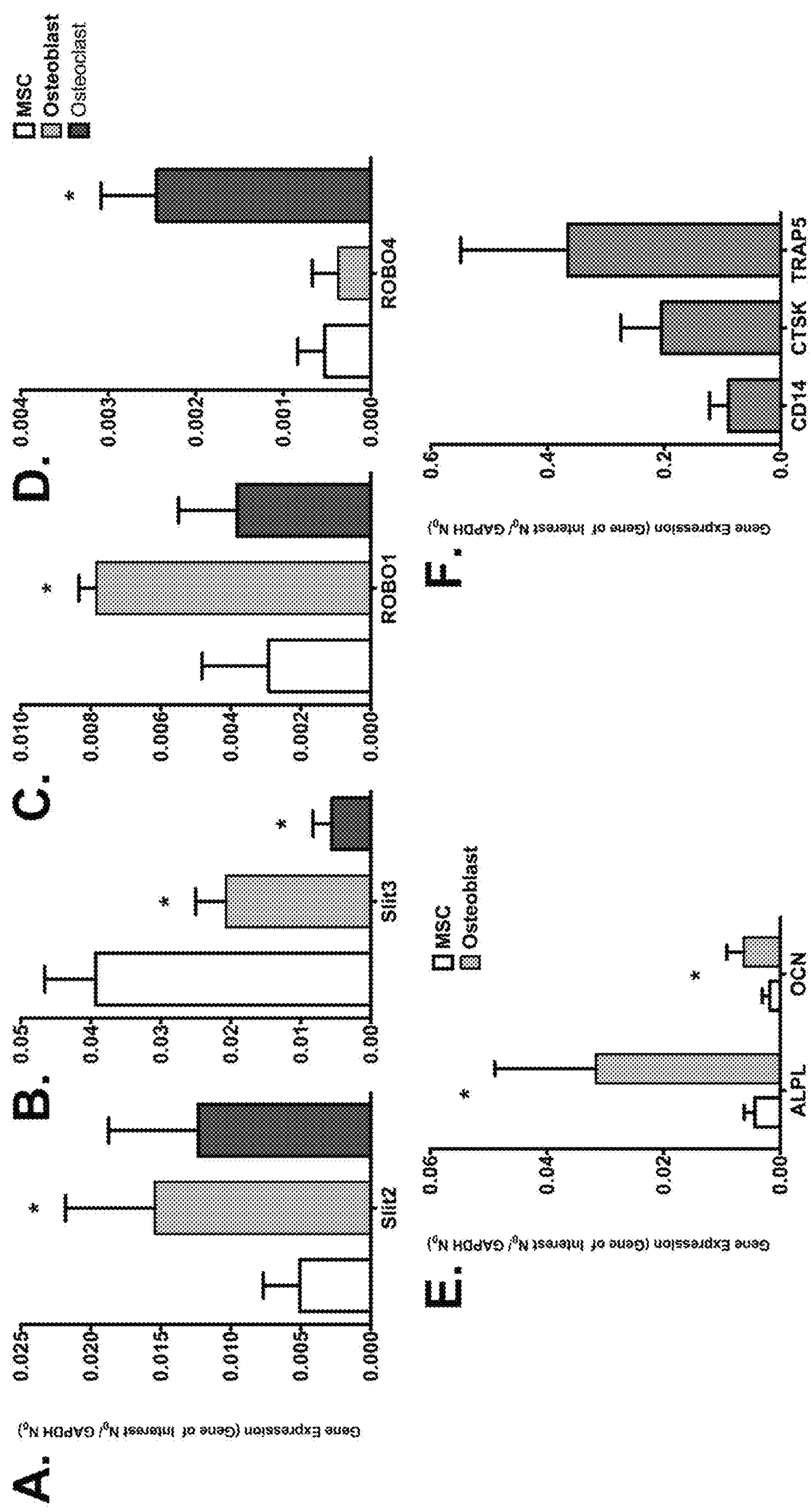
FIGS. 14A-14F.

Results:

Osteosarcoma and Ewing's sarcoma tumors express the netrin-, RGM- and slit-ligand receptors. Neurotrophic growth factor and receptor genes were widely expressed in MSC, osteoblasts (OB), Ewing's sarcoma (RDES, Hs822 and Hs863) and osteosarcoma (SaOS2). However, the following genes were not observed in the following sarcoma cell lines: RGMa was not observed in Hs863 cells. UNC5c was not present in RDES, Hs822 or Hs863 cells. UNC5d was not seen in Hs822 or Hs863 cells. NGL3 was not measured in Hs822, Hs863 or SaOS2 cells. DSCAM was not identified in Hs822 or Hs863 cells. Slit1 was not present in Hs822 cells while the ROBO4 receptor was not seen in RDES or Hs822 cells. In addition, DCC was only observed in the RDES ($p<0.0125$) cells while ROBO3 was not observed in any of the sarcoma cell lines. Though they were expressed, no significant increase in NTNS slit2, BOC gene expression was observed compared to MSC or osteoblasts. In contrast, the following genes were significantly expressed in one of the sarcoma tumor cell lines when compared to MSC: NTN1 was expressed in SaOS2 cells ($p<0.0018$). NTN3 was measured in RDES cells ($p<0.006$). NTNG1 and NTNG2 were observed in SaOS2 cells ($p<0.001$) and Hs822 cells ($p<0.0005$), respectively. UNC5d was present in RDES and SaOS2 cells ($p<0.009$). DSCAM was measured in RDES ($p<0.001$). NGL1, NGL2 and NGL3 were observed in RDES cells ($p<0.02$). Slit1 and CDON were measured in RDES cells ($p<0.04$) while SRGAP2 and ROBO2 were observed in SaOS2 cells ($p<0.011$). NTN4, RGMb and slit3 were all significantly increased in Hs822 cells compared to MSC (*, $p<0.003$). (FIGS. 14A, 14B and 14C) Conversely, NTN4, RGMb and slit3 were also significantly decreased in RDES, Hs863 and SaOS2 cells when compared to MSC (*, $p<0.03$). Neogenin gene expression was significantly increased in RDES and SaOS2 when compared to MSC (*, $p<0.0485$). (FIG. 14D) UNC5b gene expression was significantly increased in Hs822 and Hs863 cells compared to MSC (*, p<0.009). (FIG. 14E) ROBO1 was significantly increased in RDES cell compared to MSC (*, p<0.0025). (FIG. 14F) Neogenin-, UNC5b-, NGL1-, ROBO1-, and ROBO4-receptor expression was confirmed in CD99-positive Ewing's sarcoma tumor biopsy samples (brown staining). (FIG. 15)

The addition of the netrin-, RGM-, and slit-ligands did not increase sarcoma tumor cell number in culture. The addition of 100-ng of the RGMa- or RGMb-ligand resulted in a 12% decrease in RDES tumor cell number (p<0.0025). (FIG. 16A) The addition of 100-ng slit3-ligand resulted in a 20% decrease in RDES tumor cell number (p<0.001). (FIG. 16B) Smaller increases were observed in the other tumor cell lines. The NTN1-, NTN4-, slit1- and slit2-ligands had no effect on tumor cell proliferation.

Summary of Results from Examples 1-4:

The netrin-, slit- and RGM-ligands bind collagen and two major constituents of collagen matrices: heparin and laminin.

The netrin-1 and netrin-4 ligands increase bone formation and reduce bone re-absorption (destruction) through a reduction in osteoclast number.

The slit1- and slit2-ligands increase bone formation; however only the slit1-ligand reduces bone destruction through a reduction in osteoclast number.

The slit3-ligand doesn't change bone mass significantly but does increase osteoclast number, suggesting that it may be useful as a treatment for osteopetrosis (pathologic increased bone formation).

The RGMa- and RGMb-ligands increased osteoclast number and failed to increased bone mass, which suggest that both could be useful as therapies for osteopetrosis.

The netrin-1 and netrin-4 ligands decreased adipocyte (fat cell) number, which suggests that these ligands could be used to treat the increased fat accumulation that occurs in the bone marrow of osteonecrotic bones.

Despite possessing the netrin-, RGM- or slit-ligand receptors, the netrin-1, netrin-4, RGMa, RGMb, slit1, slit2 or slit3 ligands failed to increase sarcoma tumor cell proliferation.

What is claimed is:

1. A method for promoting bone formation or reducing bone destruction in a subject in need thereof, comprising administering an amount of a polypeptide to the subject, wherein the polypeptide comprises a netrin-1, netrin-4, slit1, or combinations thereof, wherein the amount of the polypeptide is effective to promote bone formation or reduce bone destruction.

2. The method of claim 1, wherein the polypeptide is administered locally to the site of injury.

3. The method of claim 1, wherein the polypeptide is administered with a collagen based carrier, either in the form of a collagen sponge, a powdered collagen, or a collagen based gelatin hydrogel.

4. The method of claim 2, wherein the injury comprises bone fracture or a surgical intervention such as would occur during the repair of a fracture or to accelerate the rate of spine fusion.

5. The method of claim 1, wherein the administration treats osteonecrosis (or osteoradionecrosis) by reducing fat cell number while promoting mesenchymal stem cells (MSC) recruitment to the site of bone necrosis.

* * * * *

SEQUENCE LISTING

```
<160> NUMBER OF SEQ ID NOS: 23

<210> SEQ ID NO 1
<211> LENGTH: 5757
<212> TYPE: DNA
<213> ORGANISM: Mus musculus

<400> SEQUENCE: 1

ggcggccgcg tcgtcactcg ggaggaagag gcggcggcgg tggcggccgg ggccggggct     60

ggggcagcgg cggccgcgcc gggcatggag ctggcaagcc cgcgttgaga caggacgctc    120

ttgctagccg ccagcgagag gctctctgca gtccggcgcg cgggctcccc ggcttgggcc    180

aggcaaactt ttctttctct tttgccatca cttagaggcg cctggtgcgg cgggcgaacc    240

gactccttgg cgcggcgggg ccggggcaag ctggccacag catgatgcgc gctgtgtggg    300

aggcgctggc ggcgctggcg gcggtggcgt gcctggtggg cgcggtgcgc ggcgggcccg    360

ggcttagcat gttcgccggc caggcggcgc agcctgatcc ttgctcggat gagaatggac    420

acccgcgccg ctgcatcccg gactttgtca acgcggcctt cggcaaggac gtgcgcgtgt    480

ccagcacctg cggccggccc ccggcgcgct actgcgtggt gagcgagcgt ggtgaagagc    540

ggctgcgctc ctgtcacctc tgcaactctt cggatcccaa gaaagcgcac ccgcccgcct    600

tcctcaccga cctcaataac ccgcacaacc tgacgtgctg gcagtccgag aactacctgc    660

agttcccgca caacgtgacg ctcactctgt cgctcggcaa gaagtttgag gtgacctatg    720

tgagcctgca attctgctcg ccgcggccag agtccatggc catctacaag tccatggact    780

acgggcgcac gtgggtgccc ttccagttct attccacgca gtgccgcaaa atgtacaacc    840

ggccgcaccg cgcgcctatc accaaacaga acgagcagga ggccgtgtgc accgactcgc    900

acaccgacat gcgcccgctc tctggcgggc tgatcgcttt cagcacgctg gacgggcggc    960

cctcggcgca cgacttcgac aactcgccgg tgctgcagga ctgggtcacg gccaccgaca   1020

tccgcgtggc tttcagccgc ctgcacacgt tcggcgacga gaacgaagac gactcggagc   1080

tggcgcgcga ctcctattac tatgcagtgt ctgacctgca ggttggcggc cgctgcaagt   1140

gcaacggcca cgcggcgcgt tgcgtgcgcg accgagacga cagtctggtg tgtgactgta   1200

ggcacaacac ggccggccct gaatgcgacc gttgcaagcc cttccactac gaccggccct   1260

ggcagcgcgc cacggcccgc gaggccaacg agtgcgtggc ctgcaactgc aacctccatg   1320
```

```
ctcggcgctg cagattcaac atggagctct ataagctatc agggcgcaag agcgggggag   1380
tctgtctcaa ctgccgccac aacactgcgg gccgccactg ccactactgc aaggagggct   1440
tctaccgaga catgggcaag cctatcaccc accggaaggc ttgcaaagcc tgtgattgcc   1500
acccagtggg tgctgctggc aagacctgca atcaaaccac tggccaatgt ccctgcaagg   1560
acggcgtgac gggcatcacc tgcaaccgat gtgccaaagg ctaccagcag agccgctccc   1620
ccatcgcccc ttgcatcaag attcctgtgg cgccacccac cactgcagcc agcagcgtgg   1680
aggaaccgga agactgtgac tcctattgca aggcctccaa aggcaagctg aagatgaaca   1740
tgaagaaata ctgcaggaag gactatgctg tccagatcca catcctgaag gccgacaaag   1800
caggggactg gtggaagttc accgtgaaca tcatctccgt gtacaagcag ggcacaagtc   1860
gtattcgccg tggtgaccag agtttgtgga tccgctcacg agacatcgcc tgcaagtgtc   1920
ccaaaatcaa gcccctcaag aagtacttgc tgttgggtaa tgccgaggac tcacctgacc   1980
agagtggcat cgtggcagac aagagcagcc tggtgatcca gtggcgggac acatgggcac   2040
ggcggctgcg caagttccag caacgggaga agaagggcaa gtgcaagaag gcctagcgcg   2100
gaggtggcgc gggctccagg agggcgggca gggcgctggc aaaggctggc agccttggac   2160
ttggccgtca ggggtttttt tgggagggtg ggggcggggc gaagtcgaag tggggcgggg   2220
ccctcagcgg ctccgcccca gccccaccct cacacccctg gctgcgctct tatgcgcatg   2280
gcagaaagca ccctgtattg acaggccagg ccctggagaa atgaggacaa gacatagcta   2340
cctcacggcg ctccttccag aacagagatg cgcttcccta gggctaggtg ggggtcgccg   2400
tggaggggtt agggaggtcc tgagaggcgg gaacagaatg gcacagtggt ctacagtcgc   2460
tgtgtttgat ggttattgaa gggggatgta agaactgtga atttttgggc ctgcagcctg   2520
ggcaggggca accaatccac caccagacac tagtcacgcc cccctccttt ctccatcacc   2580
cgctgtctag gaattcccac aggactccag actctgacaa caggtcccta tgttagaggg   2640
cccgatgaca ctgggatcag ccagctttgg tctccactgc cacctgctgg gctggtctcc   2700
tgggtggagt tcaccatctg tagggagggg agagttctcc tggggcctgc tctactccag   2760
tggggctggc ccaggctcct ggcccatcag agggcctagg gcctaaggac cctgaagtca   2820
agccgggtgg tcactgcctc tgctggagct gcctgtggaa ggaggcattg caaaccaaaa   2880
cctcccagag agtttccttg ctggaaactt ggaaacagcc ctttttatga cattttccag   2940
gggaggggga ggggtactgg cgggggttta gggcagtgac actatttgtg taatgacatc   3000
agctcccaca aggcctcaca gcaatgtcaa cagctggaga gggcctggtt aagtctggaa   3060
tgccagcggc tgtctaggca gtttgaacca ggcttggggg aaggggcttg cctgagtcag   3120
ggtagggtcg ctgctcagca aggtgcctgg cgtccaagct ggagggcaag gccaggaatg   3180
gtcaggttct tggggtccaa gcattctgtg actgcttcct gctgccgccc tcactgctgg   3240
ctccccagaa aagggacata gactccttgg ttaagaaacc cactctagct cccagctgtc   3300
ttggtctagc ctgggcagtc tggtctattc ctttctggct gccttctttg tggaggtccc   3360
caggccctcc tgtatgccta gctctctttt ctcttagaga cttaatgtcc tcacgcaggc   3420
agctccaagc ttcccttctg gttgcttccc aggccccttt agcctttccc tgcctccctg   3480
tactcgggcc tctagcctcg cgccccgcac actggatgag aggcctggcc ctctcagtca   3540
ggaaattggt ttcatttctc ctgcccactt ggctgccctg aagggccata tgagggatga   3600
agctcagccc ctcagtgaca cggctccctc tgcttctcca cttctgccca catcaccact   3660
```

```
gccacttact gagcaccctc ttggtgccag gcactttacc catatgctcc tggcctgttt   3720
tcaccacaaa cctgcgaggc agggattcac tcttgtcttc gtgttcacca gtaaaaagac   3780
atgtccacgt gcccaaggtc acaccagcac cggtactcag actctgacct caccacagtt   3840
gcacatcagc agttagccct cttgacactc ccacagtagg cgagggttgg gtgggatagt   3900
ggttaccact gagacccagg cagcttgtct ctagagaact ctgaggatat gagcctggag   3960
tatggtctgg gacagaccca gcaacacctc ctgaggaggc atcgggagtg gcggggaatg   4020
aggaatggac tccctagtgg aaagccgcaa gatccaggaa gacaggcatg gccatctgag   4080
agggcctgga gaggtggctt agctgcttcc ctagccggag gaagactaag gcttcagagg   4140
gaggctggca tgagcacaca gacctaccct ggcaagggtc aggtggcttc cctggtccaa   4200
gcttgagatt gagggcaagg tccactatcc aggagagcca gtatggtttg ttgggtacca   4260
tctgtagcaa ataacatcca gctgtacagc aggggtctca tttctgtacc agcatgtcta   4320
atgctctggc cagcttccac ccttgaaccc tggagtccag tctcacctgg tatccagcga   4380
agtctcttaa ctagacttcc cccacgcccc tgctaagcaa cagagacgtc ttgttagaaa   4440
tctaccaagg cctcctgccc tgccctctgt ggcctgctca atgggggcta cattaaatag   4500
ccaaaatgag ccaagttgtg gataaggtca ttgctgaggg agcagggttt gtcacagcca   4560
ccacctctgt ggaccagaat ccagcccacc tctcctctgc ctgagagcca gccttaggga   4620
ggcagctgtc tcctacccac cctagggagg agatggaaag ggggaagaag acatcctctt   4680
tgtacagtta ggaaggggtg caaaatggaa gtaggttttt gagtttgaga gtgtattaac   4740
agagttgtga tatgtaggtc tttgaagaaa accataccag gttagtcact taccagtcaa   4800
gatttcccag ctgtcccttt gcttaccatt tgggtagtct ggtcccctgt caccagaatg   4860
cctcctttgc tgacacacag tggcacaaag gtatgtggtg aaggtgatga catgctccta   4920
ggtacagctg tgagctgtgg tttctggcca gagcttctgt cccagaaagc agggcaggag   4980
gcaggaccat ccggctcctt cagatgggag ggagggtcag atgccaaggg caaagcctag   5040
ggaggctggg gtggcctctc cgagggcctt agggactttc tagaactctg cctcagtggt   5100
tacatacagg cagtgggtac aggctgtctt agaattgccc ctgagctgga acaagactga   5160
aatgaggaga cccttcagga ctgacctggg gaatggttcc tttagggtct caacacttga   5220
aggactccat ccaggaaacc tagagagtgg gcaagatagg ctcactaatg ggccgtggtt   5280
cacagacaga tattcctgtg gaccagagcc atgccatacc ccaggggtat caaaattgtc   5340
tttgtggggc cttgcccctg ccaaaaacta agccagcctc acctcttgtg tcagcggact   5400
tccttcccct ttccctgatc tgggtacacc cccccggcct ccctcctgtg tcaccgattc   5460
tgctcacaca gaattgtaaa tgtttagttg tgaccatgac atattgtttg ggccagtgtt   5520
cctttccaat gcatactaat atattatggt tattatatat gaatatattt aatgacatgg   5580
agaaagttgt ggattttctt tctttttctt tcttttttttt tttaaagttt ttttgttgtt   5640
agagttgtaa tggacccaga cggaacttgt aacgtgggcc ctacatgata gaactaaatc   5700
cagatatcat taaataaact cttgtatact gttctgtgaa aaaaaaaaaa aaaaaaa      5757
```

<210> SEQ ID NO 2
<211> LENGTH: 604
<212> TYPE: PRT
<213> ORGANISM: Mus musculus

<400> SEQUENCE: 2

```
Met Met Arg Ala Val Trp Glu Ala Leu Ala Ala Leu Ala Ala Val Ala
```

-continued

```
1               5                   10                  15

Cys Leu Val Gly Ala Val Arg Gly Gly Pro Gly Leu Ser Met Phe Ala
            20                  25                  30

Gly Gln Ala Ala Gln Pro Asp Pro Cys Ser Asp Glu Asn Gly His Pro
        35                  40                  45

Arg Arg Cys Ile Pro Asp Phe Val Asn Ala Ala Phe Gly Lys Asp Val
    50                  55                  60

Arg Val Ser Ser Thr Cys Gly Arg Pro Pro Ala Arg Tyr Cys Val Val
65                  70                  75                  80

Ser Glu Arg Gly Glu Glu Arg Leu Arg Ser Cys His Leu Cys Asn Ser
            85                  90                  95

Ser Asp Pro Lys Lys Ala His Pro Pro Ala Phe Leu Thr Asp Leu Asn
            100                 105                 110

Asn Pro His Asn Leu Thr Cys Trp Gln Ser Glu Asn Tyr Leu Gln Phe
        115                 120                 125

Pro His Asn Val Thr Leu Thr Leu Ser Leu Gly Lys Lys Phe Glu Val
    130                 135                 140

Thr Tyr Val Ser Leu Gln Phe Cys Ser Pro Arg Pro Glu Ser Met Ala
145                 150                 155                 160

Ile Tyr Lys Ser Met Asp Tyr Gly Arg Thr Trp Val Pro Phe Gln Phe
            165                 170                 175

Tyr Ser Thr Gln Cys Arg Lys Met Tyr Asn Arg Pro His Arg Ala Pro
            180                 185                 190

Ile Thr Lys Gln Asn Glu Gln Glu Ala Val Cys Thr Asp Ser His Thr
        195                 200                 205

Asp Met Arg Pro Leu Ser Gly Gly Leu Ile Ala Phe Ser Thr Leu Asp
    210                 215                 220

Gly Arg Pro Ser Ala His Asp Phe Asp Asn Ser Pro Val Leu Gln Asp
225                 230                 235                 240

Trp Val Thr Ala Thr Asp Ile Arg Val Ala Phe Ser Arg Leu His Thr
            245                 250                 255

Phe Gly Asp Glu Asn Glu Asp Asp Ser Glu Leu Ala Arg Asp Ser Tyr
            260                 265                 270

Tyr Tyr Ala Val Ser Asp Leu Gln Val Gly Gly Arg Cys Lys Cys Asn
        275                 280                 285

Gly His Ala Ala Arg Cys Val Arg Asp Arg Asp Asp Ser Leu Val Cys
    290                 295                 300

Asp Cys Arg His Asn Thr Ala Gly Pro Glu Cys Asp Arg Cys Lys Pro
305                 310                 315                 320

Phe His Tyr Asp Arg Pro Trp Gln Arg Ala Thr Ala Arg Glu Ala Asn
            325                 330                 335

Glu Cys Val Ala Cys Asn Cys Asn Leu His Ala Arg Arg Cys Arg Phe
            340                 345                 350

Asn Met Glu Leu Tyr Lys Leu Ser Gly Arg Lys Ser Gly Gly Val Cys
        355                 360                 365

Leu Asn Cys Arg His Asn Thr Ala Gly Arg His Cys His Tyr Cys Lys
    370                 375                 380

Glu Gly Phe Tyr Arg Asp Met Gly Lys Pro Ile Thr His Arg Lys Ala
385                 390                 395                 400

Cys Lys Ala Cys Asp Cys His Pro Val Gly Ala Ala Gly Lys Thr Cys
            405                 410                 415

Asn Gln Thr Thr Gly Gln Cys Pro Cys Lys Asp Gly Val Thr Gly Ile
            420                 425                 430
```

```
Thr Cys Asn Arg Cys Ala Lys Gly Tyr Gln Gln Ser Arg Ser Pro Ile
        435                 440                 445

Ala Pro Cys Ile Lys Ile Pro Val Ala Pro Pro Thr Thr Ala Ala Ser
    450                 455                 460

Ser Val Glu Glu Pro Glu Asp Cys Asp Ser Tyr Cys Lys Ala Ser Lys
465                 470                 475                 480

Gly Lys Leu Lys Met Asn Met Lys Lys Tyr Cys Arg Lys Asp Tyr Ala
                485                 490                 495

Val Gln Ile His Ile Leu Lys Ala Asp Lys Ala Gly Asp Trp Trp Lys
            500                 505                 510

Phe Thr Val Asn Ile Ile Ser Val Tyr Lys Gln Gly Thr Ser Arg Ile
        515                 520                 525

Arg Arg Gly Asp Gln Ser Leu Trp Ile Arg Ser Arg Asp Ile Ala Cys
    530                 535                 540

Lys Cys Pro Lys Ile Lys Pro Leu Lys Lys Tyr Leu Leu Leu Gly Asn
545                 550                 555                 560

Ala Glu Asp Ser Pro Asp Gln Ser Gly Ile Val Ala Asp Lys Ser Ser
                565                 570                 575

Leu Val Ile Gln Trp Arg Asp Thr Trp Ala Arg Arg Leu Arg Lys Phe
            580                 585                 590

Gln Gln Arg Glu Lys Lys Gly Lys Cys Lys Lys Ala
        595                 600


<210> SEQ ID NO 3
<211> LENGTH: 5954
<212> TYPE: DNA
<213> ORGANISM: Homo sapiens

<400> SEQUENCE: 3

cttcgggggc gagcgcgcgt gtgtgtgagt gcgcgccggc cagcgcgcct tctgcggcag      60

gcggacagat cctcggcgcg gcagggccgg ggcaagctgg acgcagcatg atgcgcgcag     120

tgtgggaggc gctggcggcg ctggcggcgg tggcgtgcct ggtgggcgcg gtgcgcggcg     180

ggcccgggct cagcatgttc gcgggccagg cggcgcagcc cgatccctgc tcggacgaga     240

acggccaccc gcgccgctgc atcccggact ttgtcaatgc ggccttcggc aaggacgtgc     300

gcgtgtccag cacctgcggc cggcccccgg cgcgctactg cgtggtgagc gagcgcggcg     360

aggagcggct gcgctcgtgc cacctctgca acgcgtccga ccccaagaag gcgcacccgc     420

ccgccttcct caccgacctc aacaacccgc acaacctgac gtgctggcag tccgagaact     480

acctgcagtt cccgcacaac gtcacgctca cactgtccct cggcaagaag ttcgaagtga     540

cctacgtgag cctgcagttc tgctcgccgc ggcccgagtc catggccatc tacaagtcca     600

tggactacgg gcgcacgtgg gtgcccttcc agttctactc cacgcagtgc cgcaagatgt     660

acaaccggcc gcaccgcgcg cccatcacca agcagaacga gcaggaggcc gtgtgcaccg     720

actcgcacac cgacatgcgc ccgctctcgg gcggcctcat cgccttcagc acgctggacg     780

ggcggccctc ggcgcacgac ttcgacaact cgcccgtgct gcaggactgg gtcacggcca     840

cagacatccg cgtggccttc agccgcctgc acacgttcgg cgacgagaac gaggacgact     900

cggagctggc gcgcgactcg tacttctacg cggtgtccga cctgcaggtg ggcggccggt     960

gcaagtgcaa cggccacgcg gcccgctgcg tgcgcgaccg cgacgacagc ctggtgtgcg    1020

actgcaggca caacacggcc ggcccggagt gcgaccgctg caagcccttc cactacgacc    1080

ggccctggca gcgcgccaca gcccgcgaag ccaacgagtg cgtggcctgt aactgcaacc    1140
```

```
tgcatgcccg gcgctgccgc ttcaacatgg agctctacaa gctttcgggg cgcaagagcg   1200
gaggtgtctg cctcaactgt cgccacaaca ccgccggccg ccactgccat tactgcaagg   1260
agggctacta ccgcgacatg ggcaagccca tcacccaccg gaaggcctgc aaagcctgtg   1320
attgccaccc tgtgggtgct gctggcaaaa cctgcaacca aaccaccggc cagtgtccct   1380
gcaaggacgg cgtgacgggt atcacctgca accgctgcgc caaaggctac cagcagagcc   1440
gctctcccat cgcccctgc ataaagatcc ctgtagcgcc gccgacgact gcagccagca    1500
gcgtggagga gcctgaagac tgcgattcct actgcaaggc ctccaagggg aagctgaaga   1560
ttaacatgaa aaagtactgc aagaaggact atgccgtcca gatccacatc ctgaaggcgg   1620
acaaggcggg ggactggtgg aagttcacgg tgaacatcat ctccgtgtat aagcagggca   1680
cgagccgcat ccgccgcggt gaccagagcc tgtggatccg ctcgcgggac atcgcctgca   1740
agtgtcccaa aatcaagccc ctcaagaagt acctgctgct gggcaacgcg gaggactctc   1800
cggaccagag cggcatcgtg gccgataaaa gcagcctggt gatccagtgg cgggacacgt   1860
gggcgcggcg gctgcgcaag ttccagcagc gtgagaagaa gggcaagtgc aagaaggcct   1920
agcgccgagg cagcgggcgg gcgggcgggc gggcgccagg gcggggccga gcgagagcgg   1980
gcgccttggc ccggccgccg cggacttggc ccgcgagggc tttcccaggt gggggaggg    2040
agggggcggg gccgcacggc gcggggggcg ggaccctcgg cggcccctcc ccctaccccc   2100
accctgcgcg ctctgggcgg gagccgcgtg cacgcggggc ggggtgcgcc gccggccggg   2160
ccctggagaa atgacgagac gtagctacct cacggggctc cttccagagc agagacgcgc   2220
ttccctgggc ctgggcgcgg ccgccgtgga ggggctgggg gcagcctgcc ctggggcccg   2280
ggggcgggcg cagaatcgca caactggggc cccaggcgcg gggcgtggat ggcgcggaga   2340
cgtggacggg aggagaactg tgaattctca agcccgtagt gtgggcgggg cgcggagcac   2400
ccaccaaacc accacccgac acgcagccga cgggatcccc ccctttctcc ccggcccctt   2460
ctagcagttc cccgcgggcc acctggctgt cacagcctgg actcctccat ctgaaggggc   2520
ctggcagcat ttggggagtg gacagctcct gtccagccag catgccccag gcggcctctg   2580
tctccactgc tacctgctga gtgggtccta ctgggtgggg gcttggggtc ggtgagtggt   2640
tcacctgtgg agagaggaga ggaagcccct gctgctgcct gtctctgccc ctgcccctgc   2700
ccctgcccag cgtggggctg gcccatccgg aaggcagtgg gcccagggac acccctgaga   2760
agcccaagcc gggtggtcac cgcctcatgc tggagctgcc tgttggagga ggcatcgcaa   2820
acgcaaaacc tcccagagag tttccttttg gaaacttgga accagccctt tttatgacgt   2880
tttccagggg gagggggagg ggcactggct gggtttacgg cagtgacact atttatgtaa   2940
atgacatcag ctcccgcaag gcccctcagc aatgtcaaca gctggaaagg gcctgaacgg   3000
gcttggagtc tgcaggctgc gaaggcactt gggcctggct tggggccggg ggcttgtttg   3060
agctgggatg gggtttgctg gctcagtgaa gtaccagagt gcctgagcca tgggtgggca   3120
ggggcacagg aatgaccagg ttcctggggg ccaaggaggc catgctggct tctccaaggg   3180
aaggcacaga ggctgccggc ctgcccccta cagctgtctt gggtctggcc tgggccacac   3240
cttgaccgtg cctttccaga cggtctttgt ggagtctgcc cgtgccctcc actgtgcccc   3300
agccctcctt ccaaaatctc ctagagacac ggtcctcaag caggcagccc cttttgttct   3360
gacctcctca cacagggtcc attcctgtgc cctggggcct cctggctccc tgccttcctg   3420
ggctctctgc actgcccggg cctctggccc acatcctcac acccggcgca ctgaattaag   3480
```

```
aggcctggct cccctcacag tcaggaaatt ggtttcactt tcccggccag agtttggctg   3540
ctcaaaaggg tcataccaag tatgaagctc ggcccccggt ggtctggctt ccctccgcct   3600
tccccacatt tacccgcatc acggctgcca tttattgagc acctgctgtg tgccaggcac   3660
tttacccaca tgctcccagt gtgtactcat gacaaccctg tgggacaggg actcattatc   3720
accagcaagg agactggagt acacgtgccc aaggtcatgc tgcaaattgg tggcaggact   3780
ggggctcaaa ctccagagcc cgactttctg accaggggcc acgctggccc tcactgcact   3840
ccagctctgc agcctacccg cccaatccct gtgcaggctg ggagggtgct cttgggggag   3900
tggccaccga gcccctggcc ctggttactg cctcttgagg acactggcat ctgggctgga   3960
gaacaggagc ccggggtggg gtagggcatg gggacaatca catcttcaga ggaggcagca   4020
aagtggtgcg ggatgcaggg acggacttgc cagatggcag ctccaggttc caggaaggca   4080
ggccttggat gctccgaaga ggtggtagaa aggtgttttt agaaaggtgt tttggctgcc   4140
tcagggtggt tggagagact ccaggagaga ctggcagagg tgcctcaggg gcagggagca   4200
gacagacctg ccctgggaag gggcatttgg cttccctgaa tccagcccaa ggctagaaga   4260
cagggcccct ctccaagctg tcagcgcccc tcggatgccc agtgtggtgt gctgggcgcc   4320
atcagcatca caaggcacta cgctgctggg gcggttgtcc tatttctgtc tatgccagtg   4380
tggtttcttc accctgccca gaagggctgt ggcagcccca cgatatccca ccctgggtct   4440
gggtctcacg ggtgtcctgt gaggggcttg catttgtggt ggtctctgag gccacctcag   4500
caacggagct ggcgacacgc caagcaacaa ggcatcttgc ggaaaattca gccagtgtcc   4560
tgcccctccc ttcggctcag caccccgcag ggcacaggct gtccgcccgg tggtctggcc   4620
cttggggaat gcgtcagggt gaccagatcc accatgctag cagccaggtc actgttggga   4680
ttgcacggtc gtcacgagct gcctttccta tccacacacc cagccaggac ccagcccacc   4740
actcccgact gcagccccgg cctctgcggt gagcaccatc cttgggaaag cacccctcct   4800
ccactccggt gccccactcc aaggagcaga gggaaatggg aattgaggtg tcccggtttg   4860
tacagttagg aagggatgta aaacggaact agattttgat tttgaagagt gtattaacca   4920
gaattgtgct atgtaggtgt ttgtttgaag aaaaacatac cagattagtc tttgtttttg   4980
aaacagcttc cccagttgtc ctttttctta ccagctgggt ggtctggtgc ccctgacagc   5040
tgagtgcctg ctttacggac acgcagtaat gccgaagatt tgcgggggag gacatagggc   5100
tgtccccggg attcacctgc tggctgtggt ctctgcccac tgcttctgtc cttggaaagc   5160
agggcaggag gcagcatccc caggggcctc tatgtgggag ggagggacac ctggggtcac   5220
aacccaggga gggagggtca cagcccaggg aggctgggag ctgctccaag gccctggaac   5280
tctgcctcag tcgcggcatg ctggagaggg gtacggactt actttcttgg agttgtccca   5340
ggttggaatg agactgaact caagaagaga ccctaaggga ctggggaatg gttcctgcct   5400
tcaggaaagt gaaagacgct taggctgtca acacttaaag gaagtcccct tgaagcccag   5460
agtggacaga ctagacccat tgatggggcc actggccatg gtccgtggac aagacattcc   5520
tgtgggccat ggcacaccgg gggggatcaa aatgtgtact tgtggggtct cgccccttgc   5580
caaaagccaa accagtccca ctcctgtcat tggacgtttc ttcccattcc ctcctcccaa   5640
atgcacttcc cctcctccct ctgccccctc ctgtgttttg gatttctgtt cactcagaat   5700
tgtaaatgtt tagttgtgac catgacgtat tgtttgggtc aatgtccctt tccaatgcat   5760
actaatatat tatggttatt atatatgaat atatttaatg acatggaaaa agttgtggat   5820
tttctttctt tcctttttt tgggggggggg tggggggttg gttagagttg taatggaccc   5880
```

```
agatggaact tgtaatgtgg gccccacatg atagaactaa attcagatat cattaaataa   5940

actcttgtac acta                                                     5954


<210> SEQ ID NO 4
<211> LENGTH: 604
<212> TYPE: PRT
<213> ORGANISM: Homo sapiens

<400> SEQUENCE: 4

Met Met Arg Ala Val Trp Glu Ala Leu Ala Ala Leu Ala Ala Val Ala
1               5                   10                  15

Cys Leu Val Gly Ala Val Arg Gly Gly Pro Gly Leu Ser Met Phe Ala
            20                  25                  30

Gly Gln Ala Ala Gln Pro Asp Pro Cys Ser Asp Glu Asn Gly His Pro
        35                  40                  45

Arg Arg Cys Ile Pro Asp Phe Val Asn Ala Ala Phe Gly Lys Asp Val
    50                  55                  60

Arg Val Ser Ser Thr Cys Gly Arg Pro Pro Ala Arg Tyr Cys Val Val
65                  70                  75                  80

Ser Glu Arg Gly Glu Glu Arg Leu Arg Ser Cys His Leu Cys Asn Ala
                85                  90                  95

Ser Asp Pro Lys Lys Ala His Pro Pro Ala Phe Leu Thr Asp Leu Asn
            100                 105                 110

Asn Pro His Asn Leu Thr Cys Trp Gln Ser Glu Asn Tyr Leu Gln Phe
        115                 120                 125

Pro His Asn Val Thr Leu Thr Leu Ser Leu Gly Lys Lys Phe Glu Val
    130                 135                 140

Thr Tyr Val Ser Leu Gln Phe Cys Ser Pro Arg Pro Glu Ser Met Ala
145                 150                 155                 160

Ile Tyr Lys Ser Met Asp Tyr Gly Arg Thr Trp Val Pro Phe Gln Phe
                165                 170                 175

Tyr Ser Thr Gln Cys Arg Lys Met Tyr Asn Arg Pro His Arg Ala Pro
            180                 185                 190

Ile Thr Lys Gln Asn Glu Gln Glu Ala Val Cys Thr Asp Ser His Thr
        195                 200                 205

Asp Met Arg Pro Leu Ser Gly Gly Leu Ile Ala Phe Ser Thr Leu Asp
    210                 215                 220

Gly Arg Pro Ser Ala His Asp Phe Asp Asn Ser Pro Val Leu Gln Asp
225                 230                 235                 240

Trp Val Thr Ala Thr Asp Ile Arg Val Ala Phe Ser Arg Leu His Thr
                245                 250                 255

Phe Gly Asp Glu Asn Glu Asp Asp Ser Glu Leu Ala Arg Asp Ser Tyr
            260                 265                 270

Phe Tyr Ala Val Ser Asp Leu Gln Val Gly Gly Arg Cys Lys Cys Asn
        275                 280                 285

Gly His Ala Ala Arg Cys Val Arg Asp Arg Asp Asp Ser Leu Val Cys
    290                 295                 300

Asp Cys Arg His Asn Thr Ala Gly Pro Glu Cys Asp Arg Cys Lys Pro
305                 310                 315                 320

Phe His Tyr Asp Arg Pro Trp Gln Arg Ala Thr Ala Arg Glu Ala Asn
                325                 330                 335

Glu Cys Val Ala Cys Asn Cys Asn Leu His Ala Arg Arg Cys Arg Phe
            340                 345                 350
```

```
Asn Met Glu Leu Tyr Lys Leu Ser Gly Arg Lys Ser Gly Gly Val Cys
        355                 360                 365

Leu Asn Cys Arg His Asn Thr Ala Gly Arg His Cys His Tyr Cys Lys
    370                 375                 380

Glu Gly Tyr Tyr Arg Asp Met Gly Lys Pro Ile Thr His Arg Lys Ala
385                 390                 395                 400

Cys Lys Ala Cys Asp Cys His Pro Val Gly Ala Ala Gly Lys Thr Cys
                405                 410                 415

Asn Gln Thr Thr Gly Gln Cys Pro Cys Lys Asp Gly Val Thr Gly Ile
            420                 425                 430

Thr Cys Asn Arg Cys Ala Lys Gly Tyr Gln Gln Ser Arg Ser Pro Ile
        435                 440                 445

Ala Pro Cys Ile Lys Ile Pro Val Ala Pro Pro Thr Thr Ala Ala Ser
    450                 455                 460

Ser Val Glu Glu Pro Glu Asp Cys Asp Ser Tyr Cys Lys Ala Ser Lys
465                 470                 475                 480

Gly Lys Leu Lys Ile Asn Met Lys Lys Tyr Cys Lys Lys Asp Tyr Ala
                485                 490                 495

Val Gln Ile His Ile Leu Lys Ala Asp Lys Ala Gly Asp Trp Trp Lys
            500                 505                 510

Phe Thr Val Asn Ile Ile Ser Val Tyr Lys Gln Gly Thr Ser Arg Ile
        515                 520                 525

Arg Arg Gly Asp Gln Ser Leu Trp Ile Arg Ser Arg Asp Ile Ala Cys
    530                 535                 540

Lys Cys Pro Lys Ile Lys Pro Leu Lys Lys Tyr Leu Leu Leu Gly Asn
545                 550                 555                 560

Ala Glu Asp Ser Pro Asp Gln Ser Gly Ile Val Ala Asp Lys Ser Ser
                565                 570                 575

Leu Val Ile Gln Trp Arg Asp Thr Trp Ala Arg Arg Leu Arg Lys Phe
            580                 585                 590

Gln Gln Arg Glu Lys Lys Gly Lys Cys Lys Lys Ala
        595                 600
```

<210> SEQ ID NO 5
<211> LENGTH: 2411
<212> TYPE: DNA
<213> ORGANISM: Mus musculus

<400> SEQUENCE: 5

```
gagaaggacg ggaccgagcc tcggcggcca cagaaggtgg gaaaagcgga ggaggacagc      60

cgggaggcgg cggcggccgg gaagtgaaag gtctcgcaaa gttcagcgtc ggctgcgggc     120

gccgagccct gggcgagcgg cgcacccgcc ctcagggccg ctcagccggc agcggccagg     180

ccggctatga tcccggggct cccgccgctg ctgagctgcc cgggccccgc caggccggtg     240

cgcgacggtc accccgccgc ctggcgcggc cccggcccgc ggctctgtgc ccacggtgcc     300

cactgagcga gcctggcgct ccgggaggag gaagaaccac agagccccccg gtgctcccga     360

ggaccactgc cgcttcatcc cacccgctcc cgcagctgcc cggccatggg gagctgcgca     420

cggctgctgc tgctctgggg ctgctccgcg gtggccgcag gcttgaatgg agtagccgga     480

gcgaactccc gctgtgagaa agcatgcaac cctcgcatgg gaaacttggc tttgggaaga     540

aagctccggg cagacacaat gtgtggccag aacgccaccg aactcttctg cttctacagt     600

gagaatgctg acctcacttg ccggcagccc aagtgtgata aatgcaacgc tgcccattct     660

cacctggctc acccaccctc tgccatggca gactcatcct tcaggtttcc ccggacatgg     720
```

```
tggcagtctg cagaggatgt gcacagggaa aagattcagc tagacctgga agcagaattc    780

tacttcactc acctaattat ggtgttcaag tctcccaggc ctgcagccat ggtgctggac    840

cggtcccagg actttgggaa gacctggaag ccttacaagt actttgcaac aaactgctcg    900

gctacttttg gcctggaaga tgatgttgtc aagaagggag ctatttgcac gtctagatac    960

tcaaatcctt tcccgtgcac cggaggagag gttattttca gagccctgtc accaccatac   1020

gacatagaaa acccttacag tgccaaagtg caggagcagc tgaagatcac caacctccga   1080

gtgcggctgc tcaagcgaca gtcctgccct tgtcagataa acgacctgaa cgcaaaacct   1140

caccatttta tgcactacgc agtctatgac ttcatcgtca agggcagctg cttctgcaac   1200

ggccacgctg accagtgctt acctgtggag ggcttcagac ccatcaaggc ccCgggagcg   1260

ttccacgtgg tccacgggag gtgtatgtgt aagcacaaca cagcaggcag ccactgccag   1320

cactgtgcac cattgtacaa tgaccggccc tgggaggcag cggacggcag aacaggggct   1380

cctaacgaat gcagaacttg caagtgcaat gggcacgcgg acacctgtca cttcgacgtc   1440

aacgtgtggg aggcgtcggg gaaccgcagc ggcggtgtct gcaacaactg tcagcacaac   1500

actgagggtc agcactgtca acgctgtaag cccggtttct accgcgacct cagaagaccc   1560

ttctctgccc ctgacgcttg caaagcgtgt tcctgccacc cggttggatc ggcgatcctt   1620

cctttcagct cagtgacctt ctgcgacccc agcaatggtg actgcccctg caagcctggg   1680

gtggcggggc cacattgcga cagatgcatg gtgggatact ggggctttgg agactacggc   1740

tgcagacctt gcgattgtgc ggggagctgc gacccgctca cgggagactg catcagcagt   1800

aacgctgatg tagactggta ccacgaagtc cccgcctttc actcgatgca caataagagt   1860

gagcccagct gggaatggga ggatgagcaa ggattttctg ccctccgaca ctcaggtaaa   1920

tgtgaatgta aggaacaggt gttaggaaac ccccaaagcct tctgtggaat gaagtattca   1980

tatgtgttaa aaatcaagat cttatcagcc cacgacaaag gctcccatgc cgaagtcaat   2040

gtgaagatta agaaagtctt aaagtccacc aaactgaaga tcttacgagg caagagaacg   2100

ctataccag agtcctggac taacagaggc tgcacctgtc caatcctcaa tccaggattg   2160

gagtacctgg tcgctggcca cgaggacgta agaacaggca aattaattgt gaatatgaaa   2220

agctttgtcc agcactggaa accagctctt ggcagaagag tcatgcacat cttaaaaaga   2280

gactgcgtgt agcactgaag gtcttaagca cacaagggct tttctctggg tagcagatac   2340

acaagtctaa tgaaaaagag acctcaaaat aaaactggaa tattttttaa gtgccaaaat   2400

gtaggggggg g                                                        2411
```

```
<210> SEQ ID NO 6
<211> LENGTH: 628
<212> TYPE: PRT
<213> ORGANISM: Mus musculus

<400> SEQUENCE: 6

Met Gly Ser Cys Ala Arg Leu Leu Leu Leu Trp Gly Cys Ser Ala Val
1               5                   10                  15

Ala Ala Gly Leu Asn Gly Val Ala Gly Ala Asn Ser Arg Cys Glu Lys
            20                  25                  30

Ala Cys Asn Pro Arg Met Gly Asn Leu Ala Leu Gly Arg Lys Leu Arg
        35                  40                  45

Ala Asp Thr Met Cys Gly Gln Asn Ala Thr Glu Leu Phe Cys Phe Tyr
    50                  55                  60
```

-continued

```
Ser Glu Asn Ala Asp Leu Thr Cys Arg Gln Pro Lys Cys Asp Lys Cys
65                  70                  75                  80

Asn Ala Ala His Ser His Leu Ala His Pro Pro Ser Ala Met Ala Asp
                85                  90                  95

Ser Ser Phe Arg Phe Pro Arg Thr Trp Trp Gln Ser Ala Glu Asp Val
            100                 105                 110

His Arg Glu Lys Ile Gln Leu Asp Leu Glu Ala Glu Phe Tyr Phe Thr
        115                 120                 125

His Leu Ile Met Val Phe Lys Ser Pro Arg Pro Ala Ala Met Val Leu
    130                 135                 140

Asp Arg Ser Gln Asp Phe Gly Lys Thr Trp Lys Pro Tyr Lys Tyr Phe
145                 150                 155                 160

Ala Thr Asn Cys Ser Ala Thr Phe Gly Leu Glu Asp Asp Val Val Lys
                165                 170                 175

Lys Gly Ala Ile Cys Thr Ser Arg Tyr Ser Asn Pro Phe Pro Cys Thr
            180                 185                 190

Gly Gly Glu Val Ile Phe Arg Ala Leu Ser Pro Pro Tyr Asp Ile Glu
        195                 200                 205

Asn Pro Tyr Ser Ala Lys Val Gln Glu Gln Leu Lys Ile Thr Asn Leu
    210                 215                 220

Arg Val Arg Leu Leu Lys Arg Gln Ser Cys Pro Cys Gln Ile Asn Asp
225                 230                 235                 240

Leu Asn Ala Lys Pro His His Phe Met His Tyr Ala Val Tyr Asp Phe
                245                 250                 255

Ile Val Lys Gly Ser Cys Phe Cys Asn Gly His Ala Asp Gln Cys Leu
            260                 265                 270

Pro Val Glu Gly Phe Arg Pro Ile Lys Ala Pro Gly Ala Phe His Val
        275                 280                 285

Val His Gly Arg Cys Met Cys Lys His Asn Thr Ala Gly Ser His Cys
    290                 295                 300

Gln His Cys Ala Pro Leu Tyr Asn Asp Arg Pro Trp Glu Ala Ala Asp
305                 310                 315                 320

Gly Arg Thr Gly Ala Pro Asn Glu Cys Arg Thr Cys Lys Cys Asn Gly
                325                 330                 335

His Ala Asp Thr Cys His Phe Asp Val Asn Val Trp Glu Ala Ser Gly
            340                 345                 350

Asn Arg Ser Gly Gly Val Cys Asn Asn Cys Gln His Asn Thr Glu Gly
        355                 360                 365

Gln His Cys Gln Arg Cys Lys Pro Gly Phe Tyr Arg Asp Leu Arg Arg
    370                 375                 380

Pro Phe Ser Ala Pro Asp Ala Cys Lys Ala Cys Ser Cys His Pro Val
385                 390                 395                 400

Gly Ser Ala Ile Leu Pro Phe Ser Ser Val Thr Phe Cys Asp Pro Ser
                405                 410                 415

Asn Gly Asp Cys Pro Cys Lys Pro Gly Val Ala Gly Pro His Cys Asp
            420                 425                 430

Arg Cys Met Val Gly Tyr Trp Gly Phe Gly Asp Tyr Gly Cys Arg Pro
        435                 440                 445

Cys Asp Cys Ala Gly Ser Cys Asp Pro Leu Thr Gly Asp Cys Ile Ser
    450                 455                 460

Ser Asn Ala Asp Val Asp Trp Tyr His Glu Val Pro Ala Phe His Ser
465                 470                 475                 480

Met His Asn Lys Ser Glu Pro Ser Trp Glu Trp Glu Asp Glu Gln Gly
```

```
                485                 490                 495

Phe Ser Ala Leu Arg His Ser Gly Lys Cys Glu Cys Lys Glu Gln Val
            500                 505                 510

Leu Gly Asn Pro Lys Ala Phe Cys Gly Met Lys Tyr Ser Tyr Val Leu
        515                 520                 525

Lys Ile Lys Ile Leu Ser Ala His Asp Lys Gly Ser His Ala Glu Val
    530                 535                 540

Asn Val Lys Ile Lys Lys Val Leu Lys Ser Thr Lys Leu Lys Ile Leu
545                 550                 555                 560

Arg Gly Lys Arg Thr Leu Tyr Pro Glu Ser Trp Thr Asn Arg Gly Cys
                565                 570                 575

Thr Cys Pro Ile Leu Asn Pro Gly Leu Glu Tyr Leu Val Ala Gly His
            580                 585                 590

Glu Asp Val Arg Thr Gly Lys Leu Ile Val Asn Met Lys Ser Phe Val
        595                 600                 605

Gln His Trp Lys Pro Ala Leu Gly Arg Arg Val Met His Ile Leu Lys
    610                 615                 620

Arg Asp Cys Val
625


<210> SEQ ID NO 7
<211> LENGTH: 3634
<212> TYPE: DNA
<213> ORGANISM: Homo sapiens

<400> SEQUENCE: 7

ggacgggacg gagccggggc agccagaaga ggtgggaaaa gcggaggagg acgcccagga     60

ggaggcggcg gcggcggccg ggaagtgaaa ggtctcgcaa agttcagcgg cggctgcggg    120

cgccgagccc cgggctagcg gcagacgagc ccgcagggcc gctccgcggg gcagcgcagc    180

caggccggct atggtcccgg ggctcccgcc gccccccagg tgcccgggac ccgccaggcc    240

ggtgcgcgag ggtcacccca cctccccgcg cggtcccggc ccctggctcc cagctgccgg    300

cgaccgctga ccgagcccgg cgccccagga ggaggaagaa accagggccc cgttccctcc    360

cgaggacggc ggcgcttcat cccgcagccc agaggtctcg gctccctccg gcacccgccc    420

ggcccggctg ctcccggctc ctcccggcca tggggagctg cgcgcggctg ctgctgctct    480

ggggctgcac ggtggtggcc gcaggactga gtggagtagc tggagtgagt tcccgctgtg    540

aaaaagcctg caaccctcgg atgggaaatt tggctttggg gcgaaaactc tgggcagaca    600

ccacctgcgg tcagaatgct accgaactgt actgcttcta cagtgagaac acggatctga    660

cttgtcggca gcccaaatgt gacaagtgca atgctgccta tcctcacctg gctcacctgc    720

catctgccat ggcagactca tccttccggt ttcctcgcac atggtggcag tctgcggagg    780

atgtgcacag agaaaagatc cagttagacc tggaagctga attctacttc actcacctaa    840

ttgtgatgtt caagtccccc aggccggctg ccatggtgct ggaccgctcc caggactttg    900

ggaaaacatg gaagccttat aagtactttg cgactaactg ctccgctaca tttggcctgg    960

aagatgatgt tgtcaagaag ggcgctattt gtacttctaa atactccagt ccttttccat   1020

gcactggagg agaggttatt ttcaaagctt tgtcaccacc atacgataca gagaaccctt   1080

acagtgccaa agttcaggag cagctgaaga tcaccaacct tcgcgtgcag ctgctgaaac   1140

gacagtcttg tccctgtcag agaaatgacc tgaacgaaga gcctcaacat tttacacact   1200

atgcaatcta tgatttcatt gtcaagggca gctgcttctg caatggccac gctgatcaat   1260
```

```
gcatacctgt tcatggcttc agacctgtca aggccccagg aacattccac atggtccatg   1320
ggaagtgtat gtgtaagcac aacacagcag gcagccactg ccagcactgt gccccgttat   1380
acaatgaccg gccatgggag gcagctgatg gcaaaacggg ggctcccaac gagtgcagaa   1440
cctgcaagtg taatgggcat gctgatacct gtcacttcga cgttaatgtg tgggaggcat   1500
cagggaatcg tagtggtggt gtctgtgatg actgtcagca caacacagaa ggacagtatt   1560
gccagaggtg caagccaggc ttctatcgtg acctgcggag acccttctca gctccagatg   1620
cttgcaaacc gtgttcctgc catccagtag gatcagctgt ccttcctgcc aactcagtga   1680
ccttctgcga ccccagcaat ggtgactgcc cttgcaagcc tggggtggca gggcgacgtt   1740
gtgacaggtg catggtggga tactggggct tcggagacta tggctgtcga ccatgtgact   1800
gtgcggggag ctgtgaccct atcaccggag actgcatcag cagccacaca gacatagact   1860
ggtatcatga agttcctgac ttccgtcccg tgcacaataa gagcgaacca gcctgggagt   1920
gggaggatgc gcaggggttt tctgcacttc tacactcagg taaatgcgaa tgtaaggaac   1980
agacattagg aaatgccaag gcattctgtg gaatgaaata ttcatatgtg ctaaaaataa   2040
agattttatc agctcatgat aaaggtactc atgttgaggt caatgtgaag attaaaaagg   2100
tcttaaaatc taccaaactg aagattttcc gaggaaagcg aacattatat ccagaatcat   2160
ggacggacag aggatgcact tgtccaatcc tcaatcctgg tttggaatac cttgtagcag   2220
gacatgagga tataagaaca ggcaaactaa ttgtgaatat gaaaagcttt gtccagcact   2280
ggaaaccttc tcttggaaga aaagtcatgg atattttaaa aagagagtgc aagtagcatt   2340
aagatggata gcacataatg gcacttgtct atgtacaaaa cacaaacttt agagcaagaa   2400
gacctcagac aggaaactgg aatttttaa agtgccaaaa catatagaaa tgtttgaatg   2460
catgggtctt atctaactta tctcttctgg acccatgttt aaatacagtt ttatttcatg   2520
aagagaaatg aaaacccccta cactgatatc tgttttctat gggactgatt ctgaaattct   2580
taactattaa gaatatttta atagcagcat gacatttagc agtaatccat taagggcagt   2640
acctctaaca aggacgcctt ccagcttcag cgatgttact tacgtttgat gctacttaaa   2700
gtaatgaatg acgttttaag gaatccctaa ccctactatc agaaaaggtg tttgttaaag   2760
agccttctct tgtgtgttac gcatgaactt tggtctgtag gtgttaaatg gaacctctcc   2820
atgtgtatat agtatttcct tgtataaagc actttactac ctaccacttg tgttgtgaac   2880
gtttggtgac tgctgttgaa agaaggaaaa gggtgtgtga gaaagcctac tgaagcagca   2940
gcactgccac tacatgtgga caaaagtgac catataaaag aagttgtgct atttaactct   3000
gaatacttgg agaaactagg tgaagatgca accagaaagg agaatatgta tgcgtgaagt   3060
ctcagctttg agctggaggc tagattccaa gatgacagcc atgatgaaac tttttaaaaa   3120
actaaaccag aagagacttt aaaataagag aaagaaatca taaatgtaga catatgcttg   3180
gctaaagggg aaatggactt taaattttaa agagctcatt tgcaatgcac ttgtatacac   3240
ttcaaaaatt attgtagaca cagaatttgt tatatttttg tgcttagtat ttaaacctga   3300
acattgaaac agttttcctc cttgtctttc ttaacagtaa tagtcattat atttacctgt   3360
tttttaacac aatgtatgtg atagtcaaaa aatcacagtt tttcattatt attcatcttc   3420
tgtacccacg cataaccact atacatagtt tcttttgtac ttgaatatac aaaacatgaa   3480
cacagtgcca tatgaataat ttcacataca gaaccttttt ttctctgaag tcctgtggac   3540
ttgcaaatat atatatatat tgctttgtta atttgttttt atatttcata tatgtaataa   3600
aggaatatga tctgaaaaaa aaaaaaaaaa aaaa                              3634
```

<210> SEQ ID NO 8
<211> LENGTH: 628
<212> TYPE: PRT
<213> ORGANISM: Homo sapiens

<400> SEQUENCE: 8

```
Met Gly Ser Cys Ala Arg Leu Leu Leu Leu Trp Gly Cys Thr Val Val
1               5                   10                  15

Ala Ala Gly Leu Ser Gly Val Ala Gly Val Ser Ser Arg Cys Glu Lys
            20                  25                  30

Ala Cys Asn Pro Arg Met Gly Asn Leu Ala Leu Gly Arg Lys Leu Trp
        35                  40                  45

Ala Asp Thr Thr Cys Gly Gln Asn Ala Thr Glu Leu Tyr Cys Phe Tyr
    50                  55                  60

Ser Glu Asn Thr Asp Leu Thr Cys Arg Gln Pro Lys Cys Asp Lys Cys
65                  70                  75                  80

Asn Ala Ala Tyr Pro His Leu Ala His Leu Pro Ser Ala Met Ala Asp
                85                  90                  95

Ser Ser Phe Arg Phe Pro Arg Thr Trp Trp Gln Ser Ala Glu Asp Val
            100                 105                 110

His Arg Glu Lys Ile Gln Leu Asp Leu Glu Ala Glu Phe Tyr Phe Thr
        115                 120                 125

His Leu Ile Val Met Phe Lys Ser Pro Arg Pro Ala Ala Met Val Leu
    130                 135                 140

Asp Arg Ser Gln Asp Phe Gly Lys Thr Trp Lys Pro Tyr Lys Tyr Phe
145                 150                 155                 160

Ala Thr Asn Cys Ser Ala Thr Phe Gly Leu Glu Asp Asp Val Val Lys
                165                 170                 175

Lys Gly Ala Ile Cys Thr Ser Lys Tyr Ser Ser Pro Phe Pro Cys Thr
            180                 185                 190

Gly Gly Glu Val Ile Phe Lys Ala Leu Ser Pro Pro Tyr Asp Thr Glu
        195                 200                 205

Asn Pro Tyr Ser Ala Lys Val Gln Glu Gln Leu Lys Ile Thr Asn Leu
    210                 215                 220

Arg Val Gln Leu Leu Lys Arg Gln Ser Cys Pro Cys Gln Arg Asn Asp
225                 230                 235                 240

Leu Asn Glu Glu Pro Gln His Phe Thr His Tyr Ala Ile Tyr Asp Phe
                245                 250                 255

Ile Val Lys Gly Ser Cys Phe Cys Asn Gly His Ala Asp Gln Cys Ile
            260                 265                 270

Pro Val His Gly Phe Arg Pro Val Lys Ala Pro Gly Thr Phe His Met
        275                 280                 285

Val His Gly Lys Cys Met Cys Lys His Asn Thr Ala Gly Ser His Cys
    290                 295                 300

Gln His Cys Ala Pro Leu Tyr Asn Asp Arg Pro Trp Glu Ala Ala Asp
305                 310                 315                 320

Gly Lys Thr Gly Ala Pro Asn Glu Cys Arg Thr Cys Lys Cys Asn Gly
                325                 330                 335

His Ala Asp Thr Cys His Phe Asp Val Asn Val Trp Glu Ala Ser Gly
            340                 345                 350

Asn Arg Ser Gly Gly Val Cys Asp Asp Cys Gln His Asn Thr Glu Gly
        355                 360                 365

Gln Tyr Cys Gln Arg Cys Lys Pro Gly Phe Tyr Arg Asp Leu Arg Arg
```

```
    370                 375                 380

Pro Phe Ser Ala Pro Asp Ala Cys Lys Pro Cys Ser Cys His Pro Val
385                 390                 395                 400

Gly Ser Ala Val Leu Pro Ala Asn Ser Val Thr Phe Cys Asp Pro Ser
                405                 410                 415

Asn Gly Asp Cys Pro Cys Lys Pro Gly Val Ala Gly Arg Arg Cys Asp
            420                 425                 430

Arg Cys Met Val Gly Tyr Trp Gly Phe Gly Asp Tyr Gly Cys Arg Pro
        435                 440                 445

Cys Asp Cys Ala Gly Ser Cys Asp Pro Ile Thr Gly Asp Cys Ile Ser
    450                 455                 460

Ser His Thr Asp Ile Asp Trp Tyr His Glu Val Pro Asp Phe Arg Pro
465                 470                 475                 480

Val His Asn Lys Ser Glu Pro Ala Trp Glu Trp Glu Asp Ala Gln Gly
                485                 490                 495

Phe Ser Ala Leu Leu His Ser Gly Lys Cys Glu Cys Lys Glu Gln Thr
            500                 505                 510

Leu Gly Asn Ala Lys Ala Phe Cys Gly Met Lys Tyr Ser Tyr Val Leu
        515                 520                 525

Lys Ile Lys Ile Leu Ser Ala His Asp Lys Gly Thr His Val Glu Val
    530                 535                 540

Asn Val Lys Ile Lys Lys Val Leu Lys Ser Thr Lys Leu Lys Ile Phe
545                 550                 555                 560

Arg Gly Lys Arg Thr Leu Tyr Pro Glu Ser Trp Thr Asp Arg Gly Cys
                565                 570                 575

Thr Cys Pro Ile Leu Asn Pro Gly Leu Glu Tyr Leu Val Ala Gly His
            580                 585                 590

Glu Asp Ile Arg Thr Gly Lys Leu Ile Val Asn Met Lys Ser Phe Val
        595                 600                 605

Gln His Trp Lys Pro Ser Leu Gly Arg Lys Val Met Asp Ile Leu Lys
    610                 615                 620

Arg Glu Cys Lys
625
```

<210> SEQ ID NO 9
<211> LENGTH: 7949
<212> TYPE: DNA
<213> ORGANISM: Homo sapiens

<400> SEQUENCE: 9

```
gggagaggga gacgcaggcg gcgaaacggc agaggagccg agccccctcc gcccaaggcg     60

ccctccctcc gtccgcgcac aggcgccgtc gcttggagga gcaaggtgcc tcccagcccg    120

caggggcgcc gcgcgcaagc ccgcgggctc ttcggtggct ctgccccggg actgcacctg    180

gaggcggccc cggacgggga tggtcagcgg ctgctgccgt ctggctcgcg agcgggacgc    240

tgtgagggca ccatggcgct gactcccggg tgggggtcct cggcggggcc ggtccggccg    300

gagctctggc tgctgctgtg ggcagccgcg tggcgcctgg gtgcctcggc gtgccccgcc    360

ctctgcacct gcaccggaac cacggtggac tgccacggca cggggctgca ggccattccc    420

aagaatatac ctcggaacac cgagcgcctg gaactcaatg gcaacaacat cactcggatc    480

cataagaatg actttgcggg gctcaagcag ctgcgggtgc tgcagctgat ggagaaccag    540

attggagcag tggaacgtgg tgcttttgat gacatgaagg agctggagcg gctgcgactg    600

aaccgaaacc agctgcacat gttaccggaa ctgctgttcc agaacaacca ggctttgtca    660
```

```
agactggact tgagtgagaa cgccatccag gccatcccca ggaaagcttt tcggggagct    720
acggacctta aaaatttaca gctggacaag aaccagatca gctgcattga ggaaggggcc    780
ttccgtgctc tgcgggggct ggaggtgctg accctgaaca acaacaatat caccaccatc    840
cccgtgtcca gcttcaacca tatgcccaag ctacggacct tccgcctgca ctccaaccac    900
ctgttttgcg actgccacct ggcctggctc tcgcagtggc tgaggcagcg gccaaccatc    960
gggctcttca cccagtgctc gggcccagcc agcctgcgtg gcctcaatgt ggcagaggtc   1020
cagaagagtg agttcagctg ctcaggccag ggagaagcgg ggcgcgtgcc cacctgcacc   1080
ctgtcctccg gctcctgccc ggccatgtgc acctgcagca atggcatcgt ggactgtcgt   1140
ggaaaaggcc tcactgccat cccggccaac ctgcccgaga ccatgacgga gatacgcctg   1200
gagctgaacg gcatcaagtc catccctcct ggagccttct caccctacag aaagctacgg   1260
aggatagacc tgagcaacaa tcagatcgct gagattgcac ccgacgcctt ccagggcctc   1320
cgctccctga actcgctggt cctctatgga aacaagatca cagacctccc ccgtggtgtg   1380
tttggaggcc tatacaccct acagctcctg ctcctgaatg ccaacaagat caactgcatc   1440
cggcccgatg ccttccagga cctgcagaac ctctcactgc tctccctgta tgacaacaag   1500
atccagagcc tcgccaaggg cactttcacc tccctgcggg ccatccagac tctgcacctg   1560
gcgcagaacc ctttcatttg cgactgtaac ctcaagtggc tggcagactt cctgcgcacc   1620
aatcccatcg agacgagtgg tgcccgctgt gccagtcccc ggcgcctcgc caacaagcgc   1680
atcgggcaga tcaagagcaa gaagttccgg tgctcagcca aagagcagta cttcattcca   1740
ggcacggagg attaccagct gaacagcgag tgcaacagcg acgtggtctg tccccacaag   1800
tgccgctgtg aggccaacgt ggtggagtgc tccagcctga agctcaccaa gatccctgag   1860
cgcatccccc agtccacggc agaactgcga ttgaataaca atgagatttc catcctggag   1920
gccactggga tgtttaaaaa acttacacat ctgaagaaaa tcaatctgag caacaacaag   1980
gtgtcagaaa ttgaagatgg ggccttcgag ggcgcagcct ctgtgagcga gctgcaccta   2040
actgccaacc agctggagtc catccggagc ggcatgttcc ggggtctgga tggcttgagg   2100
accctaatgc tgcggaacaa ccgcatcagc tgcatccaca acgacagctt cacgggcctg   2160
cgcaacgtcc ggctcctctc gctctacgac aaccagatca ccaccgtatc cccaggagcc   2220
ttcgacaccc tccagtccct ctccacactg aatctcctgg ccaacccttt caactgcaac   2280
tgccagctgg cctggctagg aggctggcta cggaagcgca agatcgtgac ggggaacccg   2340
cgatgccaga accctgactt tttgcggcag attcccctgc aggacgtggc cttccctgac   2400
ttcaggtgtg aggaaggcca ggaggagggg ggctgcctgc cccgcccaca gtgcccacag   2460
gagtgcgcct gcctggacac cgtggtccga tgcagcaaca agcacctgcg ggccctgccc   2520
aagggcattc ccaagaatgt cacagaactc tatttggacg ggaaccagtt cacgctggtt   2580
ccgggacagc tgtctacctt caagtacctg cagctcgtgg acctgagcaa caacaagatc   2640
agttccttaa gcaattcctc cttcaccaac atgagccagc tgaccactct gatcctcagc   2700
tacaatgccc tgcagtgcat cccgcctttg gccttccagg gactccgctc cctgcgcctg   2760
ctgtctctcc acggcaatga catctccacc ctccaagagg gcatctttgc agacgtgacc   2820
tccctgtctc acctggccat tggtgccaac cccctatact gtgactgcca cctccgctgg   2880
ctgtccagct gggtgaagac tggctacaag gaaccgggca ttgctcgttg tgctgggccc   2940
caggacatgg agggcaagct gctcctcacc acgcctgcca agaagtttga atgccaaggt   3000
```

```
cctccaacgc tggctgtcca ggccaagtgt gatctctgct tgtccagtcc gtgccagaac   3060
cagggcacct gccacaacga ccccttgag gtgtacaggt gcgcctgccc cagcggctat   3120
aagggtcgag actgtgaggt gtccctggac agctgttcca gtggcccctg tgaaaatggg   3180
ggcacctgcc atgcacagga gggcgaggat gccccgttca cgtgctcctg tcccaccggc   3240
tttgaaggac caacctgtgg ggtgaacaca gatgactgtg tggatcatgc ctgtgccaat   3300
gggggcgtct gtgtggatgg tgtgggcaac tacacctgcc agtgcccct gcagtatgag   3360
ggaaaggcct gtgagcagct ggtggacttg tgctctccgg atctgaaccc atgtcaacac   3420
gaggcccagt gtgtgggcac ccggatgggg cccaggtgtg agtgcatgcc aggttatgca   3480
ggtgacaact gcagtgagaa ccaggatgac tgcagggacc accgctgcca gaatggggcc   3540
cagtgtatgg atgaagtcaa cagctactcc tgcctctgtg ctgagggcta cagtggacag   3600
ctctgtgaga tccctcccca tctgcctgcc cccaagagcc cctgtgaggg gactgagtgc   3660
cagaatgggg ccaactgtgt ggaccagggc aacaggcctg tgtgccagtg cctcccaggc   3720
ttcggtggcc ctgagtgtga gaagttgctc agtgtcaact ttgtggatcg ggacacttac   3780
ctgcagttca ctgacctgca aaactggcca cgggccaaca tcacgttgca ggtctccacg   3840
gcagaggaca atgggatcct tctgtacaac ggggacaacg accacattgc agttgagctg   3900
taccagggcc atgtgcgtgt cagctacgac ccaggcagct accccagctc tgccatctac   3960
agtgctgaga cgatcaacga tggcaattc cacaccgttg agctggttgc ctttgaccag   4020
atggtgaatc tctccattga tggcgggagc cccatgacca tggacaactt tggcaaacat   4080
tacacgctca acagcgaggc gccactctat gtgggaggga tgcccgtgga tgtcaactca   4140
gctgccttcc gcctgtggca gatcctcaac ggcaccggct tccacggttg catccgaaac   4200
ctgtacatca acaacgagct gcaggacttc accaagacgc agatgaagcc aggcgtggtg   4260
ccaggctgcg aaccctgccg caagctctac tgcctgcatg gcatctgcca gcccaatgcc   4320
accccagggc ccatgtgcca ctgcgaggct ggctgggtgg gcctgcactg tgaccagccc   4380
gctgacggcc cctgccatgg ccacaagtgt gtccatgggc aatgcgtgcc cctcgacgct   4440
ctttcctaca gctgccagtg ccaggatggg tactcggggg cactgtgcaa ccaggccggg   4500
gccctggcag agccctgcag aggcctgcag tgcctgcatg gccactgcca ggcctcaggc   4560
accaaggggg cacactgtgt gtgtgacccc ggcttttcgg gcgagctgtg tgagcaagag   4620
tccgagtgcc ggggggaccc tgtccgggac tttcaccagg tccagagggg ctatgccatc   4680
tgccagacca cgcgccccct gtcatgggtg gagtgccggg gctcgtgccc aggccagggc   4740
tgctgccagg gccttcggct gaagcggagg aagttcacct ttgagtgcag cgatgggacc   4800
tcttttgccg aggaggtgga aaagcccacc aagtgtggct gtgccctctg cgcatagcgc   4860
tgggcgtgga caggccggtg agggcgggca aggggcccca gccgctgcag cagcggagac   4920
agtcgccagc agctgggctg gggtgcaggt catcacagga cggctcctgg gcagctgggc   4980
cctcctgggt ggggtggtgc cagagcagcc ttttaaaagc aaattgcgcc atagctgggg   5040
gcagcggggg tgggcgaggc ctgagctgcg ggctgccctc tccggaagtg ccttgcacaa   5100
ataggcgctt aataaatatt tgttgagtga atgtgtgcgt gaggtcaggc caagaagtgc   5160
agaacgatga caccccctcct tacctgctat ctgaatctgg agaagaaaaa tgacagcctt   5220
ccaaaccaac ccttcccttt ggcctgtggc ccaggctggc ttggaactgg gtctgtggcc   5280
ccagaagcct cttacccctc tgcgggcaac catgaagtac tgtcagcctc cccgggaagc   5340
cagcctggtt cattctgctg ctacagaatc tgctggtggt aggccaggct ctggagcggg   5400
```

```
ggtgccgcct cctgctggcc agggagggtc ggacccttgc cccctgggct gactggcagc   5460
tctgcagcca cggcttggga acgaggctgt gggtggaggt ggttcttagg accaggcctc   5520
tgaatcctaa agttctagca tgactactgt agctgcgagg gcttatgtgg aggaaacagt   5580
cacaggggct gctcagggtg gcagacccca ctaaagaggg cagagggttc tttgctctag   5640
ataaacaaac atcatctgcc tccagacact ggccacagta ggagtattgg tcctgggctt   5700
ccccagccac cagtcagcca caagctgtcg gtgacctatt ggtagaggga ctgggtgtga   5760
gggtctgggc cagggtgctt gacctgggag cagctggttc agagtccttc acaccgcagg   5820
ccagtaggga gcagtggaag ggacagtgct ccaggcattg ggaagtccct gctggctcta   5880
tcactcgggg caaacttctc cccacctggg ccttgggttc ttcagctata aaatggccag   5940
aggtgggggg cgggatgact aaaggaacag tgcagactcc cccactgtgg tcttgggagg   6000
ccagaggagt tagaagacct atctatctat ctatctatct acattgatca catcaaaagt   6060
atttatgtgc ctaacccggg gctggggatt gtggacgttc tggcctaatg gacagatgtg   6120
aactcatccc agagcatcgc aggaatgacc aggatgcccg ggaagagttg agctgagtgg   6180
gggctccagc cacagacagc ggcccaggcc agggagttgc tggcaacgaa ggagccagtg   6240
gtggaagaag aagaggccct gaatatacga ttgcctgccc acgttgtctt ctcttccata   6300
cacagtgaaa atgtagaaag atggtttgtg aggccaaact gtgaatgggc taaagggagg   6360
caaagttgca ctctccttcc ccagagggct caccaagagg gcacaccccc gggggttctg   6420
gtgggcaacg gggggtgagca tgtccctgcc ctggctccct ccatctgtga ccaggaggca   6480
tggctgggtg tatgttcagg tgaggctcag agtggcattg tgtccctgtc ccctgcccag   6540
ggcagtgagg ggagcccttg atgctgatta gaaggctaga actggggtag aggtgcctgg   6600
catgtctcat gccatgggga ctcaatctag caactgtgag tcctggggtc cctgtgatgg   6660
gaagagggca gtgccctgcc caatgtggca ggtgtcctca tggcaggatc tgcccctcac   6720
cagggggctg ggatctactt gcttggagct ctgagcaagg ccacaatgcc cgccccccacc   6780
cccaagtaga ctgcagcctg ggcctcatgg ggcttctccc aggcccacat ggcatccctc   6840
tctgagtttc caggccaccg tgggaccctg cagagcatct gcaccgggct ggatagggca   6900
gaaaagctca agggcagcta gcttgcctct tccctggaag aaaggtgctc tgggactcac   6960
caaccctgag aaagatagct ttcctggcca ccaccattcc ccaccaccct ggagaagcca   7020
attcccaggc ttgaagggca ctggctggca ggaggcctct tcattctgca ggaggtggaa   7080
aggacacctg tagacaggtg atgctcaccc ctcacctggc gccatggggc tgggaggtga   7140
gcggctggca tgtttgttcc tagggagcac catgtgagct taaggctccc ctgaccggcc   7200
ccaccacatg gcccagcctc ctagcacagc agcgctgacc tcagtgcagt ctgaggattg   7260
gaatccacca tgagatgatg tgagagctgt gtgccccagg atcaactttt tctccaactt   7320
ggccatcagc cagcgagttg ctaaggacct gagtcagcac tcacgttgcc tattcacact   7380
ccgcttgaaa gtccggaagg tggctactgc aaaatcaccc ctctgagaag tcctctctcc   7440
acatcttgtc cccctttgtg aagaccccta gttcgctctg cattttaggc atgaagagat   7500
acagcagggt gcgtccggag ggagctgtgg ccttgcaaca ccactggcaa cagggccggg   7560
gctcccggtg aaggtgtcag gaagtggaaa aggctggact ttgtctcctc tttgcctgct   7620
ggtagcctaa ccgcaaaagt atctctttat acagaatact tacagattct aatatatatt   7680
tgtatttcat tttgttacag tatttttata tgttaaagtc aacatccagc gtcttgtttt   7740
```

```
gcctttcaga tgctatgtgg tcgtggcacg ttttgttggg ggtttctgta gtcgtcttgt   7800

ttggatcaac tcctagaggc tggtttagaa caggcccatg agggagctgc acctgccctg   7860

gaagtattgt tttagactat gtcgatattg tctgttgtct tccatgtgaa catgacattg   7920

agtcactctg caaaaaaaaa aaaaaaaaa                                      7949


<210> SEQ ID NO 10
<211> LENGTH: 1534
<212> TYPE: PRT
<213> ORGANISM: Homo sapiens

<400> SEQUENCE: 10

Met Ala Leu Thr Pro Gly Trp Gly Ser Ser Ala Gly Pro Val Arg Pro
1               5                   10                  15

Glu Leu Trp Leu Leu Leu Trp Ala Ala Ala Trp Arg Leu Gly Ala Ser
            20                  25                  30

Ala Cys Pro Ala Leu Cys Thr Cys Thr Gly Thr Thr Val Asp Cys His
        35                  40                  45

Gly Thr Gly Leu Gln Ala Ile Pro Lys Asn Ile Pro Arg Asn Thr Glu
    50                  55                  60

Arg Leu Glu Leu Asn Gly Asn Asn Ile Thr Arg Ile His Lys Asn Asp
65                  70                  75                  80

Phe Ala Gly Leu Lys Gln Leu Arg Val Leu Gln Leu Met Glu Asn Gln
                85                  90                  95

Ile Gly Ala Val Glu Arg Gly Ala Phe Asp Asp Met Lys Glu Leu Glu
            100                 105                 110

Arg Leu Arg Leu Asn Arg Asn Gln Leu His Met Leu Pro Glu Leu Leu
        115                 120                 125

Phe Gln Asn Asn Gln Ala Leu Ser Arg Leu Asp Leu Ser Glu Asn Ala
    130                 135                 140

Ile Gln Ala Ile Pro Arg Lys Ala Phe Arg Gly Ala Thr Asp Leu Lys
145                 150                 155                 160

Asn Leu Gln Leu Asp Lys Asn Gln Ile Ser Cys Ile Glu Glu Gly Ala
                165                 170                 175

Phe Arg Ala Leu Arg Gly Leu Glu Val Leu Thr Leu Asn Asn Asn Asn
            180                 185                 190

Ile Thr Thr Ile Pro Val Ser Ser Phe Asn His Met Pro Lys Leu Arg
        195                 200                 205

Thr Phe Arg Leu His Ser Asn His Leu Phe Cys Asp Cys His Leu Ala
    210                 215                 220

Trp Leu Ser Gln Trp Leu Arg Gln Arg Pro Thr Ile Gly Leu Phe Thr
225                 230                 235                 240

Gln Cys Ser Gly Pro Ala Ser Leu Arg Gly Leu Asn Val Ala Glu Val
                245                 250                 255

Gln Lys Ser Glu Phe Ser Cys Ser Gly Gln Gly Glu Ala Gly Arg Val
            260                 265                 270

Pro Thr Cys Thr Leu Ser Ser Gly Ser Cys Pro Ala Met Cys Thr Cys
        275                 280                 285

Ser Asn Gly Ile Val Asp Cys Arg Gly Lys Gly Leu Thr Ala Ile Pro
    290                 295                 300

Ala Asn Leu Pro Glu Thr Met Thr Glu Ile Arg Leu Glu Leu Asn Gly
305                 310                 315                 320

Ile Lys Ser Ile Pro Pro Gly Ala Phe Ser Pro Tyr Arg Lys Leu Arg
                325                 330                 335
```

-continued

```
Arg Ile Asp Leu Ser Asn Asn Gln Ile Ala Glu Ile Ala Pro Asp Ala
            340                 345                 350

Phe Gln Gly Leu Arg Ser Leu Asn Ser Leu Val Leu Tyr Gly Asn Lys
        355                 360                 365

Ile Thr Asp Leu Pro Arg Gly Val Phe Gly Gly Leu Tyr Thr Leu Gln
    370                 375                 380

Leu Leu Leu Leu Asn Ala Asn Lys Ile Asn Cys Ile Arg Pro Asp Ala
385                 390                 395                 400

Phe Gln Asp Leu Gln Asn Leu Ser Leu Leu Ser Leu Tyr Asp Asn Lys
                405                 410                 415

Ile Gln Ser Leu Ala Lys Gly Thr Phe Thr Ser Leu Arg Ala Ile Gln
            420                 425                 430

Thr Leu His Leu Ala Gln Asn Pro Phe Ile Cys Asp Cys Asn Leu Lys
        435                 440                 445

Trp Leu Ala Asp Phe Leu Arg Thr Asn Pro Ile Glu Thr Ser Gly Ala
    450                 455                 460

Arg Cys Ala Ser Pro Arg Arg Leu Ala Asn Lys Arg Ile Gly Gln Ile
465                 470                 475                 480

Lys Ser Lys Lys Phe Arg Cys Ser Ala Lys Glu Gln Tyr Phe Ile Pro
                485                 490                 495

Gly Thr Glu Asp Tyr Gln Leu Asn Ser Glu Cys Asn Ser Asp Val Val
            500                 505                 510

Cys Pro His Lys Cys Arg Cys Glu Ala Asn Val Val Glu Cys Ser Ser
        515                 520                 525

Leu Lys Leu Thr Lys Ile Pro Glu Arg Ile Pro Gln Ser Thr Ala Glu
    530                 535                 540

Leu Arg Leu Asn Asn Asn Glu Ile Ser Ile Leu Glu Ala Thr Gly Met
545                 550                 555                 560

Phe Lys Lys Leu Thr His Leu Lys Lys Ile Asn Leu Ser Asn Asn Lys
                565                 570                 575

Val Ser Glu Ile Glu Asp Gly Ala Phe Glu Gly Ala Ala Ser Val Ser
            580                 585                 590

Glu Leu His Leu Thr Ala Asn Gln Leu Glu Ser Ile Arg Ser Gly Met
        595                 600                 605

Phe Arg Gly Leu Asp Gly Leu Arg Thr Leu Met Leu Arg Asn Asn Arg
    610                 615                 620

Ile Ser Cys Ile His Asn Asp Ser Phe Thr Gly Leu Arg Asn Val Arg
625                 630                 635                 640

Leu Leu Ser Leu Tyr Asp Asn Gln Ile Thr Thr Val Ser Pro Gly Ala
                645                 650                 655

Phe Asp Thr Leu Gln Ser Leu Ser Thr Leu Asn Leu Leu Ala Asn Pro
            660                 665                 670

Phe Asn Cys Asn Cys Gln Leu Ala Trp Leu Gly Gly Trp Leu Arg Lys
        675                 680                 685

Arg Lys Ile Val Thr Gly Asn Pro Arg Cys Gln Asn Pro Asp Phe Leu
    690                 695                 700

Arg Gln Ile Pro Leu Gln Asp Val Ala Phe Pro Asp Phe Arg Cys Glu
705                 710                 715                 720

Glu Gly Gln Glu Glu Gly Gly Cys Leu Pro Arg Pro Gln Cys Pro Gln
                725                 730                 735

Glu Cys Ala Cys Leu Asp Thr Val Val Arg Cys Ser Asn Lys His Leu
            740                 745                 750

Arg Ala Leu Pro Lys Gly Ile Pro Lys Asn Val Thr Glu Leu Tyr Leu
```

-continued

```
        755                 760                 765

Asp Gly Asn Gln Phe Thr Leu Val Pro Gly Gln Leu Ser Thr Phe Lys
    770                 775                 780

Tyr Leu Gln Leu Val Asp Leu Ser Asn Asn Lys Ile Ser Ser Leu Ser
785                 790                 795                 800

Asn Ser Ser Phe Thr Asn Met Ser Gln Leu Thr Thr Leu Ile Leu Ser
                805                 810                 815

Tyr Asn Ala Leu Gln Cys Ile Pro Pro Leu Ala Phe Gln Gly Leu Arg
            820                 825                 830

Ser Leu Arg Leu Leu Ser Leu His Gly Asn Asp Ile Ser Thr Leu Gln
        835                 840                 845

Glu Gly Ile Phe Ala Asp Val Thr Ser Leu Ser His Leu Ala Ile Gly
    850                 855                 860

Ala Asn Pro Leu Tyr Cys Asp Cys His Leu Arg Trp Leu Ser Ser Trp
865                 870                 875                 880

Val Lys Thr Gly Tyr Lys Glu Pro Gly Ile Ala Arg Cys Ala Gly Pro
                885                 890                 895

Gln Asp Met Glu Gly Lys Leu Leu Leu Thr Thr Pro Ala Lys Lys Phe
            900                 905                 910

Glu Cys Gln Gly Pro Pro Thr Leu Ala Val Gln Ala Lys Cys Asp Leu
        915                 920                 925

Cys Leu Ser Ser Pro Cys Gln Asn Gln Gly Thr Cys His Asn Asp Pro
    930                 935                 940

Leu Glu Val Tyr Arg Cys Ala Cys Pro Ser Gly Tyr Lys Gly Arg Asp
945                 950                 955                 960

Cys Glu Val Ser Leu Asp Ser Cys Ser Ser Gly Pro Cys Glu Asn Gly
                965                 970                 975

Gly Thr Cys His Ala Gln Glu Gly Glu Asp Ala Pro Phe Thr Cys Ser
            980                 985                 990

Cys Pro Thr Gly Phe Glu Gly Pro  Thr Cys Gly Val Asn  Thr Asp Asp
        995                 1000                1005

Cys Val  Asp His Ala Cys Ala  Asn Gly Gly Val Cys  Val Asp Gly
    1010                1015                1020

Val Gly  Asn Tyr Thr Cys Gln  Cys Pro Leu Gln Tyr  Glu Gly Lys
    1025                1030                1035

Ala Cys  Glu Gln Leu Val Asp  Leu Cys Ser Pro Asp  Leu Asn Pro
    1040                1045                1050

Cys Gln  His Glu Ala Gln Cys  Val Gly Thr Pro Asp  Gly Pro Arg
    1055                1060                1065

Cys Glu  Cys Met Pro Gly Tyr  Ala Gly Asp Asn Cys  Ser Glu Asn
    1070                1075                1080

Gln Asp  Asp Cys Arg Asp His  Arg Cys Gln Asn Gly  Ala Gln Cys
    1085                1090                1095

Met Asp  Glu Val Asn Ser Tyr  Ser Cys Leu Cys Ala  Glu Gly Tyr
    1100                1105                1110

Ser Gly  Gln Leu Cys Glu Ile  Pro Pro His Leu Pro  Ala Pro Lys
    1115                1120                1125

Ser Pro  Cys Glu Gly Thr Glu  Cys Gln Asn Gly Ala  Asn Cys Val
    1130                1135                1140

Asp Gln  Gly Asn Arg Pro Val  Cys Gln Cys Leu Pro  Gly Phe Gly
    1145                1150                1155

Gly Pro  Glu Cys Glu Lys Leu  Leu Ser Val Asn Phe  Val Asp Arg
    1160                1165                1170
```

```
Asp Thr  Tyr Leu Gln Phe Thr  Asp Leu Gln Asn Trp  Pro Arg Ala
    1175                 1180                 1185

Asn Ile  Thr Leu Gln Val Ser  Thr Ala Glu Asp Asn  Gly Ile Leu
    1190                 1195                 1200

Leu Tyr  Asn Gly Asp Asn Asp  His Ile Ala Val Glu  Leu Tyr Gln
    1205                 1210                 1215

Gly His  Val Arg Val Ser Tyr  Asp Pro Gly Ser Tyr  Pro Ser Ser
    1220                 1225                 1230

Ala Ile  Tyr Ser Ala Glu Thr  Ile Asn Asp Gly Gln  Phe His Thr
    1235                 1240                 1245

Val Glu  Leu Val Ala Phe Asp  Gln Met Val Asn Leu  Ser Ile Asp
    1250                 1255                 1260

Gly Gly  Ser Pro Met Thr Met  Asp Asn Phe Gly Lys  His Tyr Thr
    1265                 1270                 1275

Leu Asn  Ser Glu Ala Pro Leu  Tyr Val Gly Gly Met  Pro Val Asp
    1280                 1285                 1290

Val Asn  Ser Ala Ala Phe Arg  Leu Trp Gln Ile Leu  Asn Gly Thr
    1295                 1300                 1305

Gly Phe  His Gly Cys Ile Arg  Asn Leu Tyr Ile Asn  Asn Glu Leu
    1310                 1315                 1320

Gln Asp  Phe Thr Lys Thr Gln  Met Lys Pro Gly Val  Val Pro Gly
    1325                 1330                 1335

Cys Glu  Pro Cys Arg Lys Leu  Tyr Cys Leu His Gly  Ile Cys Gln
    1340                 1345                 1350

Pro Asn  Ala Thr Pro Gly Pro  Met Cys His Cys Glu  Ala Gly Trp
    1355                 1360                 1365

Val Gly  Leu His Cys Asp Gln  Pro Ala Asp Gly Pro  Cys His Gly
    1370                 1375                 1380

His Lys  Cys Val His Gly Gln  Cys Val Pro Leu Asp  Ala Leu Ser
    1385                 1390                 1395

Tyr Ser  Cys Gln Cys Gln Asp  Gly Tyr Ser Gly Ala  Leu Cys Asn
    1400                 1405                 1410

Gln Ala  Gly Ala Leu Ala Glu  Pro Cys Arg Gly Leu  Gln Cys Leu
    1415                 1420                 1425

His Gly  His Cys Gln Ala Ser  Gly Thr Lys Gly Ala  His Cys Val
    1430                 1435                 1440

Cys Asp  Pro Gly Phe Ser Gly  Glu Leu Cys Glu Gln  Glu Ser Glu
    1445                 1450                 1455

Cys Arg  Gly Asp Pro Val Arg  Asp Phe His Gln Val  Gln Arg Gly
    1460                 1465                 1470

Tyr Ala  Ile Cys Gln Thr Thr  Arg Pro Leu Ser Trp  Val Glu Cys
    1475                 1480                 1485

Arg Gly  Ser Cys Pro Gly Gln  Gly Cys Cys Gln Gly  Leu Arg Leu
    1490                 1495                 1500

Lys Arg  Arg Lys Phe Thr Phe  Glu Cys Ser Asp Gly  Thr Ser Phe
    1505                 1510                 1515

Ala Glu  Glu Val Glu Lys Pro  Thr Lys Cys Gly Cys  Ala Leu Cys
    1520                 1525                 1530

Ala

<210> SEQ ID NO 11
<211> LENGTH: 1531
<212> TYPE: PRT
```

<213> ORGANISM: Mus musculus

<400> SEQUENCE: 11

```
Met Ala Leu Thr Pro Gln Arg Gly Ser Ser Ser Gly Leu Ser Arg Pro
1               5                   10                  15

Glu Leu Trp Leu Leu Leu Trp Ala Ala Ala Trp Arg Leu Gly Ala Thr
            20                  25                  30

Ala Cys Pro Ala Leu Cys Thr Cys Thr Gly Thr Thr Val Asp Cys His
        35                  40                  45

Gly Thr Gly Leu Gln Ala Ile Pro Lys Asn Ile Pro Arg Asn Thr Glu
    50                  55                  60

Arg Leu Glu Leu Asn Gly Asn Asn Ile Thr Arg Ile His Lys Asn Asp
65                  70                  75                  80

Phe Ala Gly Leu Lys Gln Leu Arg Val Leu Gln Leu Met Glu Asn Gln
                85                  90                  95

Ile Gly Ala Val Glu Arg Gly Ala Phe Asp Asp Met Lys Glu Leu Glu
            100                 105                 110

Arg Leu Arg Leu Asn Arg Asn Gln Leu Gln Val Leu Pro Glu Leu Leu
        115                 120                 125

Phe Gln Asn Asn Gln Ala Leu Ser Arg Leu Asp Leu Ser Glu Asn Phe
    130                 135                 140

Leu Gln Ala Val Pro Arg Lys Ala Phe Arg Gly Ala Thr Asp Leu Lys
145                 150                 155                 160

Asn Leu Gln Leu Asp Lys Asn Arg Ile Ser Cys Ile Glu Glu Gly Ala
                165                 170                 175

Phe Arg Ala Leu Arg Gly Leu Glu Val Leu Thr Leu Asn Asn Asn Asn
            180                 185                 190

Ile Thr Thr Ile Pro Val Ser Ser Phe Asn His Met Pro Lys Leu Arg
        195                 200                 205

Thr Phe Arg Leu His Ser Asn His Leu Phe Cys Asp Cys His Leu Ala
    210                 215                 220

Trp Leu Ser Gln Trp Leu Arg Gln Arg Pro Thr Ile Gly Leu Phe Thr
225                 230                 235                 240

Gln Cys Ser Gly Pro Ala Ser Leu Arg Gly Leu Asn Val Ala Glu Val
                245                 250                 255

Gln Lys Gly Glu Phe Ser Cys Ser Gly Gln Gly Glu Ala Ala Gly Ala
            260                 265                 270

Pro Ala Cys Thr Leu Ser Ser Gly Ser Cys Pro Ala Met Cys Ser Cys
        275                 280                 285

Ser Ser Gly Ile Val Asp Cys Arg Gly Lys Gly Leu Thr Ala Ile Pro
    290                 295                 300

Ala Asn Leu Pro Glu Thr Met Thr Glu Ile Arg Leu Glu Leu Asn Gly
305                 310                 315                 320

Ile Lys Ser Ile Pro Pro Gly Ala Phe Ser Pro Tyr Arg Lys Leu Arg
                325                 330                 335

Arg Ile Asp Leu Ser Asn Asn Gln Ile Ala Glu Ile Ala Pro Asp Ala
            340                 345                 350

Phe Gln Gly Leu Arg Ser Leu Asn Ser Leu Val Leu Tyr Gly Asn Lys
        355                 360                 365

Ile Thr Asp Leu Pro Arg Gly Val Phe Gly Gly Leu Tyr Thr Leu Gln
    370                 375                 380

Leu Leu Leu Leu Asn Ala Asn Lys Ile Asn Cys Ile Arg Pro Asp Ala
385                 390                 395                 400
```

-continued

```
Phe Gln Asp Leu Gln Asn Leu Ser Leu Leu Ser Leu Tyr Asp Asn Lys
                405                 410                 415

Ile Gln Ser Leu Ala Lys Gly Thr Phe Thr Ser Leu Arg Ala Ile Gln
            420                 425                 430

Thr Leu His Leu Ala Gln Asn Pro Phe Ile Cys Asp Cys Asn Leu Lys
        435                 440                 445

Trp Leu Ala Asp Phe Leu Arg Thr Asn Pro Ile Glu Thr Thr Gly Ala
    450                 455                 460

Arg Cys Ala Ser Pro Arg Arg Leu Ala Asn Lys Arg Ile Gly Gln Ile
465                 470                 475                 480

Lys Ser Lys Lys Phe Arg Cys Ser Ala Lys Glu Gln Tyr Phe Ile Pro
                485                 490                 495

Gly Thr Glu Asp Tyr His Leu Asn Ser Glu Cys Thr Ser Asp Val Ala
            500                 505                 510

Cys Pro His Lys Cys Arg Cys Glu Ala Ser Val Val Glu Cys Ser Ser
        515                 520                 525

Leu Lys Leu Ser Lys Ile Pro Glu Arg Ile Pro Gln Ser Thr Thr Glu
    530                 535                 540

Leu Arg Leu Asn Asn Asn Glu Ile Ser Ile Leu Glu Ala Thr Gly Leu
545                 550                 555                 560

Phe Lys Lys Leu Ser His Leu Lys Lys Ile Asn Leu Ser Asn Asn Lys
                565                 570                 575

Val Ser Glu Ile Glu Asp Gly Thr Phe Glu Gly Ala Ala Ser Val Ser
            580                 585                 590

Glu Leu His Leu Thr Ala Asn Gln Leu Glu Ser Ile Arg Ser Gly Met
        595                 600                 605

Phe Arg Gly Leu Asp Gly Leu Arg Thr Leu Met Leu Arg Asn Asn Arg
    610                 615                 620

Ile Ser Cys Ile His Asn Asp Ser Phe Thr Gly Leu Arg Asn Val Arg
625                 630                 635                 640

Leu Leu Ser Leu Tyr Asp Asn His Ile Thr Thr Ile Ser Pro Gly Ala
                645                 650                 655

Phe Asp Thr Leu Gln Ala Leu Ser Thr Leu Asn Leu Leu Ala Asn Pro
            660                 665                 670

Phe Asn Cys Asn Cys His Leu Ser Trp Leu Gly Asp Trp Leu Arg Lys
        675                 680                 685

Arg Lys Ile Val Thr Gly Asn Pro Arg Cys Gln Asn Pro Asp Phe Leu
    690                 695                 700

Arg Gln Ile Pro Leu Gln Asp Val Ala Phe Pro Asp Phe Arg Cys Glu
705                 710                 715                 720

Glu Gly Gln Glu Glu Val Gly Cys Leu Pro Arg Pro Gln Cys Pro Gln
                725                 730                 735

Glu Cys Ala Cys Leu Asp Thr Val Val Arg Cys Ser Asn Lys His Leu
            740                 745                 750

Gln Ala Leu Pro Lys Gly Ile Pro Lys Asn Val Thr Glu Leu Tyr Leu
        755                 760                 765

Asp Gly Asn Gln Phe Thr Leu Val Pro Gly Gln Leu Ser Thr Phe Lys
    770                 775                 780

Tyr Leu Gln Leu Val Asp Leu Ser Asn Asn Lys Ile Ser Ser Leu Ser
785                 790                 795                 800

Asn Ser Ser Phe Thr Asn Met Ser Gln Leu Thr Thr Leu Ile Leu Ser
                805                 810                 815

Tyr Asn Ala Leu Gln Cys Ile Pro Pro Leu Ala Phe Gln Gly Leu Arg
```

```
            820                 825                 830

Ser Leu Arg Leu Leu Ser Leu His Gly Asn Asp Val Ser Thr Leu Gln
        835                 840                 845

Glu Gly Ile Phe Ala Asp Val Thr Ser Leu Ser His Leu Ala Ile Gly
    850                 855                 860

Ala Asn Pro Leu Tyr Cys Asp Cys Arg Leu Arg Trp Leu Ser Ser Trp
865                 870                 875                 880

Val Lys Thr Gly Tyr Lys Glu Pro Gly Ile Ala Arg Cys Ala Gly Pro
                885                 890                 895

Pro Glu Met Glu Gly Lys Leu Leu Leu Thr Thr Pro Ala Lys Lys Phe
            900                 905                 910

Glu Cys Gln Gly Pro Pro Ser Leu Ala Val Gln Ala Lys Cys Asp Pro
        915                 920                 925

Cys Leu Ser Ser Pro Cys Gln Asn Gln Gly Thr Cys His Asn Asp Pro
    930                 935                 940

Leu Glu Val Tyr Arg Cys Thr Cys Pro Ser Gly Tyr Lys Gly Arg His
945                 950                 955                 960

Cys Glu Val Ser Leu Asp Gly Cys Ser Ser Asn Pro Cys Gly Asn Gly
                965                 970                 975

Gly Thr Cys His Ala Gln Glu Gly Glu Asp Ala Gly Phe Thr Cys Ser
            980                 985                 990

Cys Pro Ser Gly Phe Glu Gly Pro  Thr Cys Gly Val Asp  Thr Asp Asp
        995                 1000                1005

Cys Val  Lys His Ala Cys Val  Asn Gly Gly Val Cys  Val Asp Gly
    1010                1015                1020

Val Gly  Asn Tyr Thr Cys Gln  Cys Pro Leu Gln Tyr  Thr Gly Arg
    1025                1030                1035

Ala Cys  Glu Gln Leu Val Asp  Phe Cys Ser Pro Asp  Met Asn Pro
    1040                1045                1050

Cys Gln  His Glu Ala Gln Cys  Val Gly Thr Pro Asp  Gly Pro Arg
    1055                1060                1065

Cys Glu  Cys Met Leu Gly Tyr  Thr Gly Asp Asn Cys  Ser Glu Asn
    1070                1075                1080

Gln Asp  Asp Cys Lys Asp His  Lys Cys Gln Asn Gly  Ala Gln Cys
    1085                1090                1095

Val Asp  Glu Val Asn Ser Tyr  Ala Cys Leu Cys Val  Glu Gly Tyr
    1100                1105                1110

Ser Gly  Gln Leu Cys Glu Ile  Pro Pro Ala Pro Arg  Ser Ser Cys
    1115                1120                1125

Glu Gly  Thr Glu Cys Gln Asn  Gly Ala Asn Cys Val  Asp Gln Gly
    1130                1135                1140

Ser Arg  Pro Val Cys Gln Cys  Leu Pro Gly Phe Gly  Gly Pro Glu
    1145                1150                1155

Cys Glu  Lys Leu Leu Ser Val  Asn Phe Val Asp Arg  Asp Thr Tyr
    1160                1165                1170

Leu Gln  Phe Thr Asp Leu Gln  Asn Trp Pro Arg Ala  Asn Ile Thr
    1175                1180                1185

Leu Gln  Val Ser Thr Ala Glu  Asp Asn Gly Ile Leu  Leu Tyr Asn
    1190                1195                1200

Gly Asp  Asn Asp His Ile Ala  Val Glu Leu Tyr Gln  Gly His Val
    1205                1210                1215

Arg Val  Ser Tyr Asp Pro Gly  Ser Tyr Pro Ser Ser  Ala Ile Tyr
    1220                1225                1230
```

```
Ser Ala  Glu Thr Ile Asn Asp  Gly Gln Phe His Thr  Val Glu Leu
    1235                 1240                 1245

Val Thr  Phe Asp Gln Met Val  Asn Leu Ser Ile Asp  Gly Gly Ser
    1250                 1255                 1260

Pro Met  Thr Met Asp Asn Phe  Gly Lys His Tyr Thr  Leu Asn Ser
    1265                 1270                 1275

Glu Ala  Pro Leu Tyr Val Gly  Gly Met Pro Val Asp  Val Asn Ser
    1280                 1285                 1290

Ala Ala  Phe Arg Leu Trp Gln  Ile Leu Asn Gly Thr  Ser Phe His
    1295                 1300                 1305

Gly Cys  Ile Arg Asn Leu Tyr  Ile Asn Asn Glu Leu  Gln Asp Phe
    1310                 1315                 1320

Thr Lys  Thr Gln Met Lys Pro  Gly Val Val Pro Gly  Cys Glu Pro
    1325                 1330                 1335

Cys Arg  Lys Leu Tyr Cys Leu  His Gly Ile Cys Gln  Pro Asn Ala
    1340                 1345                 1350

Thr Pro  Gly Pro Val Cys His  Cys Glu Ala Gly Trp  Gly Gly Leu
    1355                 1360                 1365

His Cys  Asp Gln Pro Val Asp  Gly Pro Cys His Gly  His Lys Cys
    1370                 1375                 1380

Val His  Gly Lys Cys Val Pro  Leu Asp Ala Leu Ala  Tyr Ser Cys
    1385                 1390                 1395

Gln Cys  Gln Asp Gly Tyr Ser  Gly Ala Leu Cys Asn  Gln Val Gly
    1400                 1405                 1410

Ala Val  Ala Glu Pro Cys Gly  Gly Leu Gln Cys Leu  His Gly His
    1415                 1420                 1425

Cys Gln  Ala Ser Ala Thr Lys  Gly Ala His Cys Val  Cys Ser Pro
    1430                 1435                 1440

Gly Phe  Ser Gly Glu Leu Cys  Glu Gln Glu Ser Glu  Cys Arg Gly
    1445                 1450                 1455

Asp Pro  Val Arg Asp Phe His  Arg Val Gln Arg Gly  Tyr Ala Ile
    1460                 1465                 1470

Cys Gln  Thr Thr Arg Pro Leu  Ser Trp Val Glu Cys  Arg Gly Ala
    1475                 1480                 1485

Cys Pro  Gly Gln Gly Cys Cys  Gln Gly Leu Arg Leu  Lys Arg Arg
    1490                 1495                 1500

Lys Leu  Thr Phe Glu Cys Ser  Asp Gly Thr Ser Phe  Ala Glu Glu
    1505                 1510                 1515

Val Glu  Lys Pro Thr Lys Cys  Gly Cys Ala Gln Cys  Ala
    1520                 1525                 1530
```

<210> SEQ ID NO 12
<211> LENGTH: 4950
<212> TYPE: DNA
<213> ORGANISM: Homo sapiens

<400> SEQUENCE: 12

```
cagagcaggg tggagagggc ggtgggaggc gtgtgcctga gtgggctcta ctgccttgtt      60

ccatattatt ttgtgcacat tttccctggc actctgggtt gctagccccg ccgggcactg     120

ggcctcagac actgcgcggt tccctcggag cagcaagcta aagaaagccc ccagtgccgg     180

cgaggaagga ggcggcgggg aaagatgcgc ggcgttggct ggcagatgct gtccctgtcg     240

ctggggttag tgctggcgat cctgaacaag gtggcaccgc aggcgtgccc ggcgcagtgc     300
```

```
tcttgctcgg gcagcacagt ggactgtcac gggctggcgc tgcgcagcgt gcccaggaat    360
atcccccgca acaccgagag actggattta aatggaaata acatcacaag aattacgaag    420
acagattttg ctggtcttag acatctaaga gttcttcagc ttatggagaa taagattagc    480
accattgaaa gaggagcatt ccaggatctt aaagaactag agagactgcg tttaaacaga    540
aatcaccttc agctgtttcc tgagttgctg tttcttggga ctgcgaagct atacaggctt    600
gatctcagtg aaaaccaaat tcaggcaatc ccaaggaaag ctttccgtgg ggcagttgac    660
ataaaaaatt tgcaactgga ttacaaccag atcagctgta ttgaagatgg ggcattcagg    720
gctctccggg acctggaagt gctcactctc aacaataaca acattactag actttctgtg    780
gcaagtttca accatatgcc taaacttagg acttttcgac tgcattcaaa caacctgtat    840
tgtgactgcc acctggcctg gctctccgac tggcttcgcc aaaggcctcg ggttggtctg    900
tacactcagt gtatgggccc ctcccacctg agaggccata atgtagccga ggttcaaaaa    960
cgagaatttg tctgcagtgg tcaccagtca tttatggctc cttcttgtag tgttttgcac   1020
tgccctgccg cctgtacctg tagcaacaat atcgtagact gtcgtgggaa aggtctcact   1080
gagatcccca caaatcttcc agagaccatc acagaaatac gtttggaaca gaacacaatc   1140
aaagtcatcc ctcctggagc tttctcacca tataaaaagc ttagacgaat tgacctgagc   1200
aataatcaga tctctgaact tgcaccagat gctttccaag gactacgctc tctgaattca   1260
cttgtcctct atggaaataa aatcacagaa ctccccaaaa gtttatttga aggactgttt   1320
tccttacagc tcctattatt gaatgccaac aagataaact gccttcgggt agatgctttt   1380
caggatctcc acaacttgaa ccttctctcc ctatatgaca acaagcttca gaccatcgcc   1440
aaggggacct tttcacctct tcgggccatt caaactatgc atttggccca gaaccccttt   1500
atttgtgact gccatctcaa gtggctagcg gattatctcc ataccaaccc gattgagacc   1560
agtggtgccc gttgcaccag cccccgccgc ctggcaaaca aaagaattgg acagatcaaa   1620
agcaagaaat tccgttgttc agctaaagaa cagtatttca ttccaggtac agaagattat   1680
cgatcaaaat taagtggaga ctgctttgcg gatctggctt gccctgaaaa gtgtcgctgt   1740
gaaggaacca cagtagattg ctctaatcaa aagctcaaca aaatcccgga gcacattccc   1800
cagtacactg cagagttgcg tctcaataat aatgaattta ccgtgttgga agccacagga   1860
atctttaaga aacttcctca attacgtaaa ataaacttta gcaacaataa gatcacagat   1920
attgaggagg gagcatttga aggagcatct ggtgtaaatg aaatacttct tacgagtaat   1980
cgtttggaaa atgtgcagca taagatgttc aagggattgg aaagcctcaa aactttgatg   2040
ttgagaagca atcgaataac ctgtgtgggg aatgacagtt tcataggact cagttctgtg   2100
cgtttgcttt ctttgtatga taatcaaatt actacagttg caccaggggc atttgatact   2160
ctccattctt tatctactct aaacctcttg gccaatcctt ttaactgtaa ctgctacctg   2220
gcttggttgg gagagtggct gagaaagaag agaattgtca cgggaaatcc tagatgtcaa   2280
aaaccatact tcctgaaaga aatacccatc caggatgtgg ccattcagga cttcacttgt   2340
gatgacggaa atgatgacaa tagttgctcc ccactttctc gctgtcctac tgaatgtact   2400
tgcttggata cagtcgtccg atgtagcaac aagggtttga aggtcttgcc gaaaggtatt   2460
ccaagagatg tcacagagtt gtatctggat ggaaaccaat ttacactggt tcccaaggaa   2520
ctctccaact acaaacattt aacacttata gacttaagta acaacagaat aagcacgctt   2580
tctaatcaga gcttcagcaa catgacccag ctcctcacct taattcttag ttacaaccgt   2640
ctgagatgta ttcctcctcg cacctttgat ggattaaagt ctcttcgatt actttctcta   2700
```

```
catggaaatg acatttctgt tgtgcctgaa ggtgctttca atgatctttc tgcattatca   2760
catctagcaa ttggagccaa ccctctttac tgtgattgta acatgcagtg gttatccgac   2820
tgggtgaagt cggaatataa ggagcctgga attgctcgtt gtgctggtcc tggagaaatg   2880
gcagataaac ttttactcac aactccctcc aaaaaattta cctgtcaagg tcctgtggat   2940
gtcaatattc tagctaagtg taacccctgc ctatcaaatc cgtgtaaaaa tgatggcaca   3000
tgtaatagtg atccagttga cttttaccga tgcacctgtc catatggttt caaggggcag   3060
gactgtgatg tcccaattca tgcctgcatc agtaacccat gtaaacatgg aggaacttgc   3120
cacttaaagg aaggagaaga agatggattc tggtgtattt gtgctgatgg atttgaagga   3180
gaaaattgtg aagtcaacgt tgatgattgt gaagataatg actgtgaaaa taattctaca   3240
tgtgtcgatg gcattaataa ctacacatgc ctttgcccac ctgagtatac aggtgagttg   3300
tgtgaggaga agctggactt ctgtgcccag gacctgaacc cctgccagca cgattcaaag   3360
tgcatcctaa ctccaaaggg attcaaatgt gactgcacac cagggtacgt aggtgaacac   3420
tgcgacatcg attttgacga ctgccaagac aacaagtgta aaaacggagc ccactgcaca   3480
gatgcagtga acggctatac gtgcatatgc cccgaaggtt acagtggctt gttctgtgag   3540
ttttctccac ccatggtcct ccctcgtacc agcccctgtg ataattttga ttgtcagaat   3600
ggagctcagt gtatcgtcag aataaatgag ccaatatgtc agtgtttgcc tggctatcag   3660
ggagaaaagt gtgaaaaatt ggttagtgtg aattttataa acaaagagtc ttatcttcag   3720
attccttcag ccaaggttcg gcctcagacg aacataacac ttcagattgc cacagatgaa   3780
gacagcggaa tcctcctgta taagggtgac aaagaccata tcgcggtaga actctatcgg   3840
gggcgtgttc gtgccagcta tgacaccggc tctcatccag cttctgccat ttacagtgtg   3900
gagacaatca atgatggaaa cttccacatt gtggaactac ttgccttgga tcagagtctc   3960
tctttgtccg tggatggtgg gaaccccaaa atcatcacta acttgtcaaa gcagtccact   4020
ctgaattttg actctccact ctatgtagga ggcatgccag ggaagagtaa cgtggcatct   4080
ctgcgccagg cccctgggca gaacggaacc agcttccacg gctgcatccg gaacctttac   4140
atcaacagtg agctgcagga cttccagaag gtgccgatgc aaacaggcat tttgcctggc   4200
tgtgagccat gccacaagaa ggtgtgtgcc catggcacat gccagcccag cagccaggca   4260
ggcttcacct gcgagtgcca ggaaggatgg atggggcccc tctgtgacca acggaccaat   4320
gacccttgcc ttggaaataa atgcgtacat ggcacctgct tgcccatcaa tgcgttctcc   4380
tacagctgta agtgcttgga gggccatgga ggtgtcctct gtgatgaaga ggaggatctg   4440
tttaacccat gccaggcgat caagtgcaag cacgggaagt gcaggctttc aggtctgggg   4500
cagccctact gtgaatgcag cagtggatac acgggggaca gctgtgatcg agaaatctct   4560
tgtcgagggg aaaggataag agattattac caaaagcagc agggctatgc tgcttgccaa   4620
acaaccaaga aggtgtcccg attagagtgc agaggtgggt gtgcaggagg gcagtgctgt   4680
ggaccgctga ggagcaagcg gcggaaatac tctttcgaat gcactgacgg ctcctccttt   4740
gtggacgagg ttgagaaagt ggtgaagtgc ggctgtacga ggtgtgtgtc ctaaacacac   4800
tcccggcagc tctgtctttg gaaaaggttg tatacttctt gaccatgtgg gactaatgaa   4860
tgcttcatag tggaaatatt tgaaatatat tgtaaaatac agaacagact tatttttatt   4920
atgagaataa agactttttt tctgcatttg                                    4950
```

<210> SEQ ID NO 13

```
<211> LENGTH: 1529
<212> TYPE: PRT
<213> ORGANISM: Homo sapiens

<400> SEQUENCE: 13

Met Arg Gly Val Gly Trp Gln Met Leu Ser Leu Ser Leu Gly Leu Val
1               5                   10                  15

Leu Ala Ile Leu Asn Lys Val Ala Pro Gln Ala Cys Pro Ala Gln Cys
            20                  25                  30

Ser Cys Ser Gly Ser Thr Val Asp Cys His Gly Leu Ala Leu Arg Ser
        35                  40                  45

Val Pro Arg Asn Ile Pro Arg Asn Thr Glu Arg Leu Asp Leu Asn Gly
    50                  55                  60

Asn Asn Ile Thr Arg Ile Thr Lys Thr Asp Phe Ala Gly Leu Arg His
65                  70                  75                  80

Leu Arg Val Leu Gln Leu Met Glu Asn Lys Ile Ser Thr Ile Glu Arg
                85                  90                  95

Gly Ala Phe Gln Asp Leu Lys Glu Leu Glu Arg Leu Arg Leu Asn Arg
            100                 105                 110

Asn His Leu Gln Leu Phe Pro Glu Leu Leu Phe Leu Gly Thr Ala Lys
        115                 120                 125

Leu Tyr Arg Leu Asp Leu Ser Glu Asn Gln Ile Gln Ala Ile Pro Arg
    130                 135                 140

Lys Ala Phe Arg Gly Ala Val Asp Ile Lys Asn Leu Gln Leu Asp Tyr
145                 150                 155                 160

Asn Gln Ile Ser Cys Ile Glu Asp Gly Ala Phe Arg Ala Leu Arg Asp
                165                 170                 175

Leu Glu Val Leu Thr Leu Asn Asn Asn Asn Ile Thr Arg Leu Ser Val
            180                 185                 190

Ala Ser Phe Asn His Met Pro Lys Leu Arg Thr Phe Arg Leu His Ser
        195                 200                 205

Asn Asn Leu Tyr Cys Asp Cys His Leu Ala Trp Leu Ser Asp Trp Leu
    210                 215                 220

Arg Gln Arg Pro Arg Val Gly Leu Tyr Thr Gln Cys Met Gly Pro Ser
225                 230                 235                 240

His Leu Arg Gly His Asn Val Ala Glu Val Gln Lys Arg Glu Phe Val
                245                 250                 255

Cys Ser Gly His Gln Ser Phe Met Ala Pro Ser Cys Ser Val Leu His
            260                 265                 270

Cys Pro Ala Ala Cys Thr Cys Ser Asn Asn Ile Val Asp Cys Arg Gly
        275                 280                 285

Lys Gly Leu Thr Glu Ile Pro Thr Asn Leu Pro Glu Thr Ile Thr Glu
    290                 295                 300

Ile Arg Leu Glu Gln Asn Thr Ile Lys Val Ile Pro Pro Gly Ala Phe
305                 310                 315                 320

Ser Pro Tyr Lys Lys Leu Arg Arg Ile Asp Leu Ser Asn Asn Gln Ile
                325                 330                 335

Ser Glu Leu Ala Pro Asp Ala Phe Gln Gly Leu Arg Ser Leu Asn Ser
            340                 345                 350

Leu Val Leu Tyr Gly Asn Lys Ile Thr Glu Leu Pro Lys Ser Leu Phe
        355                 360                 365

Glu Gly Leu Phe Ser Leu Gln Leu Leu Leu Leu Asn Ala Asn Lys Ile
    370                 375                 380

Asn Cys Leu Arg Val Asp Ala Phe Gln Asp Leu His Asn Leu Asn Leu
```

```
385                 390                 395                 400

Leu Ser Leu Tyr Asp Asn Lys Leu Gln Thr Ile Ala Lys Gly Thr Phe
                405                 410                 415

Ser Pro Leu Arg Ala Ile Gln Thr Met His Leu Ala Gln Asn Pro Phe
            420                 425                 430

Ile Cys Asp Cys His Leu Lys Trp Leu Ala Asp Tyr Leu His Thr Asn
        435                 440                 445

Pro Ile Glu Thr Ser Gly Ala Arg Cys Thr Ser Pro Arg Arg Leu Ala
    450                 455                 460

Asn Lys Arg Ile Gly Gln Ile Lys Ser Lys Lys Phe Arg Cys Ser Ala
465                 470                 475                 480

Lys Glu Gln Tyr Phe Ile Pro Gly Thr Glu Asp Tyr Arg Ser Lys Leu
                485                 490                 495

Ser Gly Asp Cys Phe Ala Asp Leu Ala Cys Pro Glu Lys Cys Arg Cys
            500                 505                 510

Glu Gly Thr Thr Val Asp Cys Ser Asn Gln Lys Leu Asn Lys Ile Pro
        515                 520                 525

Glu His Ile Pro Gln Tyr Thr Ala Glu Leu Arg Leu Asn Asn Asn Glu
    530                 535                 540

Phe Thr Val Leu Glu Ala Thr Gly Ile Phe Lys Lys Leu Pro Gln Leu
545                 550                 555                 560

Arg Lys Ile Asn Phe Ser Asn Asn Lys Ile Thr Asp Ile Glu Glu Gly
                565                 570                 575

Ala Phe Glu Gly Ala Ser Gly Val Asn Glu Ile Leu Leu Thr Ser Asn
            580                 585                 590

Arg Leu Glu Asn Val Gln His Lys Met Phe Lys Gly Leu Glu Ser Leu
        595                 600                 605

Lys Thr Leu Met Leu Arg Ser Asn Arg Ile Thr Cys Val Gly Asn Asp
    610                 615                 620

Ser Phe Ile Gly Leu Ser Ser Val Arg Leu Leu Ser Leu Tyr Asp Asn
625                 630                 635                 640

Gln Ile Thr Thr Val Ala Pro Gly Ala Phe Asp Thr Leu His Ser Leu
                645                 650                 655

Ser Thr Leu Asn Leu Leu Ala Asn Pro Phe Asn Cys Asn Cys Tyr Leu
            660                 665                 670

Ala Trp Leu Gly Glu Trp Leu Arg Lys Lys Arg Ile Val Thr Gly Asn
        675                 680                 685

Pro Arg Cys Gln Lys Pro Tyr Phe Leu Lys Glu Ile Pro Ile Gln Asp
    690                 695                 700

Val Ala Ile Gln Asp Phe Thr Cys Asp Asp Gly Asn Asp Asp Asn Ser
705                 710                 715                 720

Cys Ser Pro Leu Ser Arg Cys Pro Thr Glu Cys Thr Cys Leu Asp Thr
                725                 730                 735

Val Val Arg Cys Ser Asn Lys Gly Leu Lys Val Leu Pro Lys Gly Ile
            740                 745                 750

Pro Arg Asp Val Thr Glu Leu Tyr Leu Asp Gly Asn Gln Phe Thr Leu
        755                 760                 765

Val Pro Lys Glu Leu Ser Asn Tyr Lys His Leu Thr Leu Ile Asp Leu
    770                 775                 780

Ser Asn Asn Arg Ile Ser Thr Leu Ser Asn Gln Ser Phe Ser Asn Met
785                 790                 795                 800

Thr Gln Leu Leu Thr Leu Ile Leu Ser Tyr Asn Arg Leu Arg Cys Ile
                805                 810                 815
```

```
Pro Pro Arg Thr Phe Asp Gly Leu Lys Ser Leu Arg Leu Leu Ser Leu
            820                 825                 830

His Gly Asn Asp Ile Ser Val Val Pro Glu Gly Ala Phe Asn Asp Leu
        835                 840                 845

Ser Ala Leu Ser His Leu Ala Ile Gly Ala Asn Pro Leu Tyr Cys Asp
    850                 855                 860

Cys Asn Met Gln Trp Leu Ser Asp Trp Val Lys Ser Glu Tyr Lys Glu
865                 870                 875                 880

Pro Gly Ile Ala Arg Cys Ala Gly Pro Gly Glu Met Ala Asp Lys Leu
                885                 890                 895

Leu Leu Thr Thr Pro Ser Lys Lys Phe Thr Cys Gln Gly Pro Val Asp
            900                 905                 910

Val Asn Ile Leu Ala Lys Cys Asn Pro Cys Leu Ser Asn Pro Cys Lys
        915                 920                 925

Asn Asp Gly Thr Cys Asn Ser Asp Pro Val Asp Phe Tyr Arg Cys Thr
    930                 935                 940

Cys Pro Tyr Gly Phe Lys Gly Gln Asp Cys Asp Val Pro Ile His Ala
945                 950                 955                 960

Cys Ile Ser Asn Pro Cys Lys His Gly Gly Thr Cys His Leu Lys Glu
                965                 970                 975

Gly Glu Glu Asp Gly Phe Trp Cys Ile Cys Ala Asp Gly Phe Glu Gly
            980                 985                 990

Glu Asn Cys Glu Val Asn Val Asp  Asp Cys Glu Asp Asn  Asp Cys Glu
        995                 1000                1005

Asn Asn  Ser Thr Cys Val Asp  Gly Ile Asn Asn Tyr  Thr Cys Leu
    1010                1015                1020

Cys Pro  Pro Glu Tyr Thr Gly  Glu Leu Cys Glu Glu  Lys Leu Asp
    1025                1030                1035

Phe Cys  Ala Gln Asp Leu Asn  Pro Cys Gln His Asp  Ser Lys Cys
    1040                1045                1050

Ile Leu  Thr Pro Lys Gly Phe  Lys Cys Asp Cys Thr  Pro Gly Tyr
    1055                1060                1065

Val Gly  Glu His Cys Asp Ile  Asp Phe Asp Asp Cys  Gln Asp Asn
    1070                1075                1080

Lys Cys  Lys Asn Gly Ala His  Cys Thr Asp Ala Val  Asn Gly Tyr
    1085                1090                1095

Thr Cys  Ile Cys Pro Glu Gly  Tyr Ser Gly Leu Phe  Cys Glu Phe
    1100                1105                1110

Ser Pro  Pro Met Val Leu Pro  Arg Thr Ser Pro Cys  Asp Asn Phe
    1115                1120                1125

Asp Cys  Gln Asn Gly Ala Gln  Cys Ile Val Arg Ile  Asn Glu Pro
    1130                1135                1140

Ile Cys  Gln Cys Leu Pro Gly  Tyr Gln Gly Glu Lys  Cys Glu Lys
    1145                1150                1155

Leu Val  Ser Val Asn Phe Ile  Asn Lys Glu Ser Tyr  Leu Gln Ile
    1160                1165                1170

Pro Ser  Ala Lys Val Arg Pro  Gln Thr Asn Ile Thr  Leu Gln Ile
    1175                1180                1185

Ala Thr  Asp Glu Asp Ser Gly  Ile Leu Leu Tyr Lys  Gly Asp Lys
    1190                1195                1200

Asp His  Ile Ala Val Glu Leu  Tyr Arg Gly Arg Val  Arg Ala Ser
    1205                1210                1215
```

```
Tyr Asp  Thr Gly Ser His Pro  Ala Ser Ala Ile Tyr  Ser Val Glu
    1220                 1225                 1230

Thr Ile  Asn Asp Gly Asn Phe  His Ile Val Glu Leu  Leu Ala Leu
    1235                 1240                 1245

Asp Gln  Ser Leu Ser Leu Ser  Val Asp Gly Gly Asn  Pro Lys Ile
    1250                 1255                 1260

Ile Thr  Asn Leu Ser Lys Gln  Ser Thr Leu Asn Phe  Asp Ser Pro
    1265                 1270                 1275

Leu Tyr  Val Gly Gly Met Pro  Gly Lys Ser Asn Val  Ala Ser Leu
    1280                 1285                 1290

Arg Gln  Ala Pro Gly Gln Asn  Gly Thr Ser Phe His  Gly Cys Ile
    1295                 1300                 1305

Arg Asn  Leu Tyr Ile Asn Ser  Glu Leu Gln Asp Phe  Gln Lys Val
    1310                 1315                 1320

Pro Met  Gln Thr Gly Ile Leu  Pro Gly Cys Glu Pro  Cys His Lys
    1325                 1330                 1335

Lys Val  Cys Ala His Gly Thr  Cys Gln Pro Ser Ser  Gln Ala Gly
    1340                 1345                 1350

Phe Thr  Cys Glu Cys Gln Glu  Gly Trp Met Gly Pro  Leu Cys Asp
    1355                 1360                 1365

Gln Arg  Thr Asn Asp Pro Cys  Leu Gly Asn Lys Cys  Val His Gly
    1370                 1375                 1380

Thr Cys  Leu Pro Ile Asn Ala  Phe Ser Tyr Ser Cys  Lys Cys Leu
    1385                 1390                 1395

Glu Gly  His Gly Gly Val Leu  Cys Asp Glu Glu Glu  Asp Leu Phe
    1400                 1405                 1410

Asn Pro  Cys Gln Ala Ile Lys  Cys Lys His Gly Lys  Cys Arg Leu
    1415                 1420                 1425

Ser Gly  Leu Gly Gln Pro Tyr  Cys Glu Cys Ser Ser  Gly Tyr Thr
    1430                 1435                 1440

Gly Asp  Ser Cys Asp Arg Glu  Ile Ser Cys Arg Gly  Glu Arg Ile
    1445                 1450                 1455

Arg Asp  Tyr Tyr Gln Lys Gln  Gln Gly Tyr Ala Ala  Cys Gln Thr
    1460                 1465                 1470

Thr Lys  Lys Val Ser Arg Leu  Glu Cys Arg Gly Gly  Cys Ala Gly
    1475                 1480                 1485

Gly Gln  Cys Cys Gly Pro Leu  Arg Ser Lys Arg Arg  Lys Tyr Ser
    1490                 1495                 1500

Phe Glu  Cys Thr Asp Gly Ser  Ser Phe Val Asp Glu  Val Glu Lys
    1505                 1510                 1515

Val Val  Lys Cys Gly Cys Thr  Arg Cys Val Ser
    1520                 1525
```

<210> SEQ ID NO 14
<211> LENGTH: 1521
<212> TYPE: PRT
<213> ORGANISM: Mus musculus

<400> SEQUENCE: 14

```
Met Ser Gly Ile Gly Trp Gln Thr Leu Ser Leu Ser Leu Gly Leu Val
1               5                   10                  15

Leu Ser Ile Leu Asn Lys Val Ala Pro Gln Ala Cys Pro Ala Gln Cys
            20                  25                  30

Ser Cys Ser Gly Ser Thr Val Asp Cys His Gly Leu Ala Leu Arg Ser
        35                  40                  45
```

```
Val Pro Arg Asn Ile Pro Arg Asn Thr Glu Arg Leu Asp Leu Asn Gly
    50                  55                  60

Asn Asn Ile Thr Arg Ile Thr Lys Ile Asp Phe Ala Gly Leu Arg His
65                  70                  75                  80

Leu Arg Val Leu Gln Leu Met Glu Asn Arg Ile Ser Thr Ile Glu Arg
                85                  90                  95

Gly Ala Phe Gln Asp Leu Lys Glu Leu Glu Arg Leu Arg Leu Asn Arg
            100                 105                 110

Asn Asn Leu Gln Leu Phe Pro Glu Leu Leu Phe Leu Gly Thr Ala Lys
        115                 120                 125

Leu Tyr Arg Leu Asp Leu Ser Glu Asn Gln Ile Gln Ala Ile Pro Arg
    130                 135                 140

Lys Ala Phe Arg Gly Ala Val Asp Ile Lys Asn Leu Gln Leu Asp Tyr
145                 150                 155                 160

Asn Gln Ile Ser Cys Ile Glu Asp Gly Ala Phe Arg Ala Leu Arg Asp
                165                 170                 175

Leu Glu Val Leu Thr Leu Asn Asn Asn Asn Ile Thr Arg Leu Ser Val
            180                 185                 190

Ala Ser Phe Asn His Met Pro Lys Leu Arg Thr Phe Arg Leu His Ser
        195                 200                 205

Asn Asn Leu Tyr Cys Asp Cys His Leu Ala Trp Leu Ser Asp Trp Leu
    210                 215                 220

Arg Gln Arg Pro Arg Val Gly Leu Tyr Thr Gln Cys Met Gly Pro Ser
225                 230                 235                 240

His Leu Arg Gly His Asn Val Ala Glu Val Gln Lys Arg Glu Phe Val
                245                 250                 255

Cys Ser Gly His Gln Ser Phe Met Ala Pro Ser Cys Ser Val Leu His
            260                 265                 270

Cys Pro Ala Ala Cys Thr Cys Ser Asn Asn Ile Val Asp Cys Arg Gly
        275                 280                 285

Lys Gly Leu Thr Glu Ile Pro Thr Asn Leu Pro Glu Thr Ile Thr Glu
    290                 295                 300

Ile Arg Leu Glu Gln Asn Ser Ile Arg Val Ile Pro Pro Gly Ala Phe
305                 310                 315                 320

Ser Pro Tyr Lys Lys Leu Arg Arg Leu Asp Leu Ser Asn Asn Gln Ile
                325                 330                 335

Ser Glu Leu Ala Pro Asp Ala Phe Gln Gly Leu Arg Ser Leu Asn Ser
            340                 345                 350

Leu Val Leu Tyr Gly Asn Lys Ile Thr Glu Leu Pro Lys Ser Leu Phe
        355                 360                 365

Glu Gly Leu Phe Ser Leu Gln Leu Leu Leu Leu Asn Ala Asn Lys Ile
    370                 375                 380

Asn Cys Leu Arg Val Asp Ala Phe Gln Asp Leu His Asn Leu Asn Leu
385                 390                 395                 400

Leu Ser Leu Tyr Asp Asn Lys Leu Gln Thr Val Ala Lys Gly Thr Phe
                405                 410                 415

Ser Ala Leu Arg Ala Ile Gln Thr Met His Leu Ala Gln Asn Pro Phe
            420                 425                 430

Ile Cys Asp Cys His Leu Lys Trp Leu Ala Asp Tyr Leu His Thr Asn
        435                 440                 445

Pro Ile Glu Thr Ser Gly Ala Arg Cys Thr Ser Pro Arg Arg Leu Ala
    450                 455                 460
```

-continued

```
Asn Lys Arg Ile Gly Gln Ile Lys Ser Lys Lys Phe Arg Cys Ser Gly
465                 470                 475                 480

Thr Glu Asp Tyr Arg Ser Lys Leu Ser Gly Asp Cys Phe Ala Asp Leu
                485                 490                 495

Ala Cys Pro Glu Lys Cys Arg Cys Glu Gly Thr Thr Val Asp Cys Ser
            500                 505                 510

Asn Gln Arg Leu Asn Lys Ile Pro Asp His Ile Pro Gln Tyr Thr Ala
        515                 520                 525

Glu Leu Arg Leu Asn Asn Asn Glu Phe Thr Val Leu Glu Ala Thr Gly
    530                 535                 540

Ile Phe Lys Lys Leu Pro Gln Leu Arg Lys Ile Asn Phe Ser Asn Asn
545                 550                 555                 560

Lys Ile Thr Asp Ile Glu Glu Gly Ala Phe Glu Gly Ala Ser Gly Val
                565                 570                 575

Asn Glu Ile Leu Leu Thr Ser Asn Arg Leu Glu Asn Val Gln His Lys
            580                 585                 590

Met Phe Lys Gly Leu Glu Ser Leu Lys Thr Leu Met Leu Arg Ser Asn
        595                 600                 605

Arg Ile Ser Cys Val Gly Asn Asp Ser Phe Ile Gly Leu Gly Ser Val
    610                 615                 620

Arg Leu Leu Ser Leu Tyr Asp Asn Gln Ile Thr Thr Val Ala Pro Gly
625                 630                 635                 640

Ala Phe Asp Ser Leu His Ser Leu Ser Thr Leu Asn Leu Leu Ala Asn
                645                 650                 655

Pro Phe Asn Cys Asn Cys His Leu Ala Trp Leu Gly Glu Trp Leu Arg
            660                 665                 670

Arg Lys Arg Ile Val Thr Gly Asn Pro Arg Cys Gln Lys Pro Tyr Phe
        675                 680                 685

Leu Lys Glu Ile Pro Ile Gln Asp Val Ala Ile Gln Asp Phe Thr Cys
    690                 695                 700

Asp Asp Gly Asn Asp Asp Asn Ser Cys Ser Pro Leu Ser Arg Cys Pro
705                 710                 715                 720

Ser Glu Cys Thr Cys Leu Asp Thr Val Val Arg Cys Ser Asn Lys Gly
                725                 730                 735

Leu Lys Val Leu Pro Lys Gly Ile Pro Lys Asp Val Thr Glu Leu Tyr
            740                 745                 750

Leu Asp Gly Asn Gln Phe Thr Leu Val Pro Lys Glu Leu Ser Asn Tyr
        755                 760                 765

Lys His Leu Thr Leu Ile Asp Leu Ser Asn Asn Arg Ile Ser Thr Leu
    770                 775                 780

Ser Asn Gln Ser Phe Ser Asn Met Thr Gln Leu Leu Thr Leu Ile Leu
785                 790                 795                 800

Ser Tyr Asn Arg Leu Arg Cys Ile Pro Pro Arg Thr Phe Asp Gly Leu
                805                 810                 815

Lys Ser Leu Arg Leu Leu Ser Leu His Gly Asn Asp Ile Ser Val Val
            820                 825                 830

Pro Glu Gly Ala Phe Asn Asp Leu Ser Ala Leu Ser His Leu Ala Ile
        835                 840                 845

Gly Ala Asn Pro Leu Tyr Cys Asp Cys Asn Met Gln Trp Leu Ser Asp
    850                 855                 860

Trp Val Lys Ser Glu Tyr Lys Glu Pro Gly Ile Ala Arg Cys Ala Gly
865                 870                 875                 880

Pro Gly Glu Met Ala Asp Lys Leu Leu Leu Thr Thr Pro Ser Lys Lys
```

```
                885                 890                 895

Phe Thr Cys Gln Gly Pro Val Asp Ile Thr Ile Gln Ala Lys Cys Asn
            900                 905                 910

Pro Cys Leu Ser Asn Pro Cys Lys Asn Asp Gly Thr Cys Asn Asn Asp
        915                 920                 925

Pro Val Asp Phe Tyr Arg Cys Thr Cys Pro Tyr Gly Phe Lys Gly Gln
    930                 935                 940

Asp Cys Asp Val Pro Ile His Ala Cys Ile Ser Asn Pro Cys Lys His
945                 950                 955                 960

Gly Gly Thr Cys His Leu Lys Glu Gly Glu Asn Ala Gly Phe Trp Cys
                965                 970                 975

Thr Cys Ala Asp Gly Phe Glu Gly Glu Asn Cys Glu Val Asn Ile Asp
            980                 985                 990

Asp Cys Glu Asp Asn Asp Cys Glu  Asn Asn Ser Thr Cys  Val Asp Gly
        995                 1000                1005

Ile Asn  Asn Tyr Thr Cys Leu  Cys Pro Pro Glu Tyr  Thr Gly Glu
    1010                1015                1020

Leu Cys  Glu Glu Lys Leu Asp  Phe Cys Ala Gln Asp  Leu Asn Pro
    1025                1030                1035

Cys Gln  His Asp Ser Lys Cys  Ile Leu Thr Pro Lys  Gly Phe Lys
    1040                1045                1050

Cys Asp  Cys Thr Pro Gly Tyr  Ile Gly Glu His Cys  Asp Ile Asp
    1055                1060                1065

Phe Asp  Asp Cys Gln Asp Asn  Lys Cys Lys Asn Gly  Ala His Cys
    1070                1075                1080

Thr Asp  Ala Val Asn Gly Tyr  Thr Cys Val Cys Pro  Glu Gly Tyr
    1085                1090                1095

Ser Gly  Leu Phe Cys Glu Phe  Ser Pro Pro Met Val  Leu Pro Arg
    1100                1105                1110

Thr Ser  Pro Cys Asp Asn Phe  Asp Cys Gln Asn Gly  Ala Gln Cys
    1115                1120                1125

Ile Ile  Arg Ile Asn Glu Pro  Ile Cys Gln Cys Leu  Pro Gly Tyr
    1130                1135                1140

Leu Gly  Glu Lys Cys Glu Lys  Leu Val Ser Val Asn  Phe Val Asn
    1145                1150                1155

Lys Glu  Ser Tyr Leu Gln Ile  Pro Ser Ala Lys Val  Arg Pro Gln
    1160                1165                1170

Thr Asn  Ile Thr Leu Gln Ile  Ala Thr Asp Glu Asp  Ser Gly Ile
    1175                1180                1185

Leu Leu  Tyr Lys Gly Asp Lys  Asp His Ile Ala Val  Glu Leu Tyr
    1190                1195                1200

Arg Gly  Arg Val Arg Ala Ser  Tyr Asp Thr Gly Ser  His Pro Ala
    1205                1210                1215

Ser Ala  Ile Tyr Ser Val Glu  Thr Ile Asn Asp Gly  Asn Phe His
    1220                1225                1230

Ile Val  Glu Leu Leu Thr Leu  Asp Ser Ser Leu Ser  Leu Ser Val
    1235                1240                1245

Asp Gly  Gly Ser Pro Lys Val  Ile Thr Asn Leu Ser  Lys Gln Ser
    1250                1255                1260

Thr Leu  Asn Phe Asp Ser Pro  Leu Tyr Val Gly Gly  Met Pro Gly
    1265                1270                1275

Lys Asn  Asn Val Ala Ser Leu  Arg Gln Ala Pro Gly  Gln Asn Gly
    1280                1285                1290
```

```
Thr Ser  Phe His Gly Cys Ile  Arg Asn Leu Tyr Ile  Asn Ser Glu
    1295                 1300                 1305

Leu Gln  Asp Phe Arg Lys Met  Pro Met Gln Thr Gly  Ile Leu Pro
    1310                 1315                 1320

Gly Cys  Glu Pro Cys His Lys  Lys Val Cys Ala His  Gly Met Cys
    1325                 1330                 1335

Gln Pro  Ser Ser Gln Ser Gly  Phe Thr Cys Glu Cys  Glu Glu Gly
    1340                 1345                 1350

Trp Met  Gly Pro Leu Cys Asp  Gln Arg Thr Asn Asp  Pro Cys Leu
    1355                 1360                 1365

Gly Asn  Lys Cys Val His Gly  Thr Cys Leu Pro Ile  Asn Ala Phe
    1370                 1375                 1380

Ser Tyr  Ser Cys Lys Cys Leu  Glu Gly His Gly Gly  Val Leu Cys
    1385                 1390                 1395

Asp Glu  Glu Glu Asp Leu Phe  Asn Pro Cys Gln Met  Ile Lys Cys
    1400                 1405                 1410

Lys His  Gly Lys Cys Arg Leu  Ser Gly Val Gly Gln  Pro Tyr Cys
    1415                 1420                 1425

Glu Cys  Asn Ser Gly Phe Thr  Gly Asp Ser Cys Asp  Arg Glu Ile
    1430                 1435                 1440

Ser Cys  Arg Gly Glu Arg Ile  Arg Asp Tyr Tyr Gln  Lys Gln Gln
    1445                 1450                 1455

Gly Tyr  Ala Ala Cys Gln Thr  Thr Lys Lys Val Ser  Arg Leu Glu
    1460                 1465                 1470

Cys Arg  Gly Gly Cys Ala Gly  Gly Gln Cys Cys Gly  Pro Leu Arg
    1475                 1480                 1485

Ser Lys  Arg Arg Lys Tyr Ser  Phe Glu Cys Thr Asp  Gly Ser Ser
    1490                 1495                 1500

Phe Val  Asp Glu Val Glu Lys  Val Val Lys Cys Gly  Cys Ala Arg
    1505                 1510                 1515

Cys Ala  Ser
    1520
```

<210> SEQ ID NO 15
<211> LENGTH: 9727
<212> TYPE: DNA
<213> ORGANISM: Homo sapiens

<400> SEQUENCE: 15

```
gagagcgagc gccggccagc tcacccggcc gccccgtgcc ccagccgcag ccgccgcgct      60

ccccagccca gccccaagcc ggacctcccc gggcgccacg ccccattgcg ctcgccccag     120

gtccccaacc cggcccgcgg gccagcgggg ccagggggcg ctccgcacct gggcactccc     180

agcgatgcgc agcggggcag cgccggcccc gccgatggag ctgctgttgc tgccgccgcc     240

gccgcccgga gcgccccgct ccgcccgcgc cccgtgcgcc tgagcaccga gctcgcccct     300

cctccgcgct aactccgccg cccgctcccc aggccgcccg cgctccccgc gcgcctcctc     360

gggctccacg cgtcttgccc cgcagaggca gcctcctcca ggagcggggc cctgcacacc     420

atggccccgg ggtgggcagg ggtcggcgcc gccgtgcgcg cccgcctggc gctggccttg     480

gcgctggcga gcgtcctgag tgggcctcca gccgtcgcct gccccaccaa gtgtacctgc     540

tccgctgcca gcgtggactg ccacgggctg ggcctccgcg cggttcctcg ggcatcccc     600

cgcaacgctg agcgccttga cctggacaga aataatatca ccaggatcac caagatggac     660
```

```
ttcgctgggc tcaagaacct ccgagtcttg catctggaag acaaccaggt cagcgtcatc    720
gagagaggcg ccttccagga cctgaagcag ctagagcgac tgcgcctgaa caagaataag    780
ctgcaagtcc ttccagaatt gcttttccag agcacgccga agctcaccag actagatttg    840
agtgaaaacc agatccaggg gatcccgagg aaggcgttcc gcggcatcac cgatgtgaag    900
aacctgcaac tggacaacaa ccacatcagc tgcattgaag atggagcctt ccgagcgctg    960
cgcgatttgg agatccttac cctcaacaac aacaacatca gtcgcatcct ggtcaccagc   1020
ttcaaccaca tgccgaagat ccgaactctg cgcctccact ccaaccacct gtactgcgac   1080
tgccacctgg cctggctctc ggattggctg cgacagcgac ggacagttgg ccagttcaca   1140
ctctgcatgg ctcctgtgca tttgaggggc ttcaacgtgg cggatgtgca gaagaaggag   1200
tacgtgtgcc cagcccccca ctcggagccc ccatcctgca atgccaactc catctcctgc   1260
ccttcgccct gcacgtgcag caataacatc gtggactgtc gaggaaaggg cttgatggag   1320
attcctgcca acttgccgga gggcatcgtc gaaatacgcc tagaacagaa ctccatcaaa   1380
gccatccctg caggagcctt cacccagtac aagaaactga agcgaataga catcagcaag   1440
aatcagatat cggatattgc tccagatgcc ttccagggcc tgaaatcact cacatcgctg   1500
gtcctgtatg ggaacaagat caccgagatt gccaagggac tgtttgatgg gctggtgtcc   1560
ctacagctgc tcctcctcaa tgccaacaag atcaactgcc tgcgggtgaa cacgtttcag   1620
gacctgcaga acctcaactt gctctccctg tatgacaaca agctgcagac catcagcaag   1680
gggctcttcg cccctctgca gtccatccag acactccact tagcccaaaa cccatttgtg   1740
tgcgactgcc acttgaagtg gctggccgac tacctccagg acaaccccat cgagacaagc   1800
ggggcccgct gcagcagccc gcgccgactc gccaacaagc gcatcagcca gatcaagagc   1860
aagaagttcc gctgctcagg ctccgaggat taccgcagca ggttcagcag cgagtgcttc   1920
atggacctcg tgtgccccga gaagtgtcgc tgtgagggca cgattgtgga ctgctccaac   1980
cagaagctgg tccgcatccc aagccacctc cctgaatatg tcaccgacct gcgactgaat   2040
gacaatgagg tatctgttct ggaggccact ggcatcttca agaagttgcc caacctgcgg   2100
aaaataaatc tgagtaacaa taagatcaag gaggtgcgag agggagcttt cgatggagca   2160
gccagcgtgc aggagctgat gctgacaggg aaccagctgg agaccgtgca cgggcgcgtg   2220
ttccgtggcc tcagtggcct caaaaccttg atgctgagga gtaacttgat cggctgtgtg   2280
agtaatgaca cctttgccgg cctgagttcg gtgagactgc tgtccctcta tgacaatcgg   2340
atcaccacca tcacccctgg ggccttcacc acgcttgtct ccctgtccac cataaacctc   2400
ctgtccaacc ccttcaactg caactgccac ctggcctggc tcggcaagtg gttgaggaag   2460
aggcggatcg tcagtgggaa ccctaggtgc cagaagccat tttcctcaa ggagattccc   2520
atccaggatg tggccatcca ggacttcacc tgtgatggca acgaggagag tagctgccag   2580
ctgagcccgc gctgcccgga gcagtgcacc tgtatggaga cagtggtgcg atgcagcaac   2640
aaggggctcc gcgccctccc cagaggcatg cccaaggatg tgaccgagct gtacctggaa   2700
ggaaaccacc taacagccgt gcccagagag ctgtccgccc tccgacacct gacgcttatt   2760
gacctgagca acaacagcat cagcatgctg accaattaca ccttcagtaa catgtctcac   2820
ctctccactc tgatcctgag ctacaaccgg ctgaggtgca tccccgtcca cgccttcaac   2880
gggctgcggt ccctgcgagt gctaaccctc catggcaatg acatttccag cgttcctgaa   2940
ggctccttca acgacctcac atctctttcc catctggcgc tgggaaccaa cccactccac   3000
tgtgactgca gtcttcggtg gctgtcggag tgggtgaagg cggggtacaa ggagcctggc   3060
```

```
atcgcccgct gcagtagccc tgagcccatg gctgacaggc tcctgctcac caccccaacc   3120
caccgcttcc agtgcaaagg gccagtggac atcaacattg tggccaaatg caatgcctgc   3180
ctctccagcc cgtgcaagaa taacgggaca tgcacccagg accctgtgga gctgtaccgc   3240
tgtgcctgcc cctacagcta caagggcaag gactgcactg tgcccatcaa cacctgcatc   3300
cagaacccct gtcagcatgg aggcacctgc cacctgagtg acagccacaa ggatgggttc   3360
agctgctcct gccctctggg ctttgagggg cagcggtgtg agatcaaccc agatgactgt   3420
gaggacaacg actgcgaaaa caatgccacc tgcgtggacg ggatcaacaa ctacgtgtgt   3480
atctgtccgc ctaactacac aggtgagcta tgcgacgagg tgattgacca ctgtgtgcct   3540
gagctgaacc tctgtcagca tgaggccaag tgcatccccc tggacaaagg attcagctgc   3600
gagtgtgtcc ctggctacag cgggaagctc tgtgagacag acaatgatga ctgtgtggcc   3660
cacaagtgcc gccacggggc ccagtgcgtg gacacaatca atggctacac atgcacctgc   3720
ccccagggct tcagtggacc cttctgtgaa cacccccac ccatggtcct actgcagacc   3780
agcccatgcg accagtacga gtgccagaac ggggcccagt gcatcgtggt gcagcaggag   3840
cccacctgcc gctgcccacc aggcttcgcc ggccccagat gcgagaagct catcactgtc   3900
aacttcgtgg gcaaagactc ctacgtggaa ctggcctccg ccaaggtccg accccaggcc   3960
aacatctccc tgcaggtggc cactgacaag gacaacggca tccttctcta caaaggagac   4020
aatgaccccc tggcactgga gctgtaccag ggccacgtgc ggctggtcta tgacagcctg   4080
agttcccctc caaccacagt gtacagtgtg gagacagtga atgatgggca gtttcacagt   4140
gtggagctgg tgacgctaaa ccagaccctg aacctagtag tggacaaagg aactccaaag   4200
agcctgggga agctccagaa gcagccagca gtgggcatca acagcccct ctaccttgga   4260
ggcatcccca cctccaccgg cctctctgcc ttgcgccagg gcacggaccg gcctctaggc   4320
ggcttccacg gatgcatcca tgaggtgcgc atcaacaacg agctgcagga cttcaaggcc   4380
ctcccaccac agtccctggg ggtgtcacca ggctgcaagt cctgcaccgt gtgcaagcac   4440
ggcctgtgcc gctccgtgga gaaggacagc gtggtgtgcg agtgccgccc aggctggacc   4500
ggcccactct gcgatcagga ggcccgggac ccctgcctcg gccacagatg ccaccatgga   4560
aaatgtgtgg caactgggac ctcatacatg tgcaagtgtg ccgagggcta tggaggggac   4620
ttgtgtgaca acaagaatga ctctgccaat gcctgctcag ccttcaagtg tcaccatggg   4680
cagtgccaca tctcagacca aggggagccc tactgcctgt gccagcccgg ctttagcggc   4740
gagcactgcc aacaagagaa tccgtgcctg ggacaagtag tccgagaggt gatccgccgc   4800
cagaaaggtt atgcatcatg tgccacagcc tccaaggtgc ccatcatgga atgtcgtggg   4860
ggctgtgggc cccagtgctg ccagcccacc cgcagcaagc ggcggaaata cgtcttccag   4920
tgcacggacg gctcctcgtt tgtagaagag gtggagagac acttagagtg cggctgcctc   4980
gcgtgttcct aagcccctgc ccgcctgcct gccacctctc ggactccagc ttgatggagt   5040
tgggacagcc atgtgggacc ccctggtgat tcagcatgaa ggaaatgaag ctggagagga   5100
aggtaaagaa gaagagaata ttaagtatat tgtaaaataa acaaaaaata gaacttattt   5160
ttattatgga aagtgactat tttcatcttt tattatataa atatattaca ccatctgcgt   5220
atatgtacca tatagtgagt tatttttacc aagttttgtg ttgtgtattt gttgtgtttt   5280
taaaaatagc tgtttaaaaa tttaagaaaa aaatagacta ataaaaatgc tttaaaacaa   5340
aaggataaga ataaagaatg atagcctgtc tgaggaagga ggaagatgtt ttcatgttta   5400
```

```
tgaaacggta ttatgtcggc agtagaccaa gagctgctca ttgagatcag aaaaaggaat   5460
aagaggaaga gagagaagga aaagaccttt gtttcttgtt ttttaactcc cttttatttt   5520
tcctccccta aaattaccca gcttttcgga gtcctggatg tcagtgccca aaatgcccag   5580
ttcttccagg aaaagctgct gagccctggc cttctcagtc tcactgccac tcaaaaatat   5640
tgctgtccct gtctgtccca gaccccccctt cagggtatct gaacccactg ggggacccct   5700
cttctccttc ctgggtggcc ctggcttccg tatctgaacc cactggggga cccctcttct   5760
ccttcctggc tggccctggc ttccaatcga ggactgacta ttgaagtctg ctacaggtgt   5820
catttggaac tgtcttacca aattttaaaa cagctgctat ttttcctgct cctccccagg   5880
agaggggtct tcctagagga ggcgagggaa gagaatatca tggtgtctcc tcaggaccca   5940
tgcactggcc ctctctcctc cttccaggta atttttcatt ggaatgtatc ccagtagaga   6000
aggtagtcag cccttcttgg aagcggaagg ctgggagcca agtcaagtct gcccacagcg   6060
ctagatgtcc aactctggaa ggttcttgga ggctcttgtt gtaagacagg cctctgccac   6120
ctgatcctcc aggtcaccag catgacgata gagactcctt gcccatctgt gacactttcc   6180
aatgcatatc caaactttac cttattttat ctatgcaacc cctgcctccc tgggaaggat   6240
aagggagtag agctgggttc actaagaagg aagtttaggc cctcacaggc tctggaactt   6300
gccttaagcc acacaccaga taagtggagg agccagacca gaagtccaga cccaaagctt   6360
gagattcttc ctctagaatg ggtgagcaca ggtgattcag gcggcttaaa tccatcagag   6420
cagccctgcc ggaaaaggaa ataatatgat gttttttcct gctcttgttc tgccttgctc   6480
actccttctc cctccgcagt atctggaaag attctggaga ccagggctta tgcatctagg   6540
gaaagtgacc aagggcagcc tatccagcct ctgcctccat tcctgaaggg gacttccctg   6600
cccctgtttc tttccatgtc tctccctccc tcactcccat ttgcccccctt ccaccccatc   6660
aggttagcca catatcttcc agggctcagc tgttcacacc aactccctgg ctcttatcat   6720
ccatccctcc ttcccccagg agcttccact gtaggagttt cagggagaag agtttggaat   6780
tcattggacc tttcagccct caggttccct agaggagcct agttgatctg tgagtaccaa   6840
tggtgggcca aagacgcagg gaataatgaa gggagaaaga aaagaaagga agatggagga   6900
aaacgaggca actggaagaa ggaaggaagg aaagaaggaa gggatggagg ggatgaagag   6960
aagggagaga gggatatagc tgaggaattt atctaaaaat gtgcatgtaa atctccatta   7020
tgttccaggt actgtgcctt atgatggctt tgtttttgt tgtcattaga gacaaggtct   7080
tgctttgtca cccaggctgg agtagagtgg ttcgatcata gctcaccgca gcctcaacct   7140
cctaggctca agccatcttc ctgcctcagt ctcccaaaat gctgggatta caggtgtgag   7200
ccactatgct cagcctgttt caaacattat tataatagca gatttattta gtactttatt   7260
atacatcaga taccactcta attgtgaaat agatatatat tcatttaatt attgaaacaa   7320
ccatgtagtt aaaacactat taactcattt tacagttgag tagactgaga cacagagaag   7380
ttaaagaact tgcccaagag taaatgtcta ataaaccgta gagccaggat ctgggcccag   7440
gctgtctgac tccagaactt gctcactcaa ccactaaacc atcctgcttc tcatgggaaa   7500
gaaacacatc ctgcctttga ggatcctaca gcctgtgaca aaaacagtca taaaaatgga   7560
caattgcctt attacacaag gagctcttaa gtggcaatac aagcaatgga agtggctgtc   7620
cagaggaggg aacttctagt cctaggtctt taaggatgaa taggagtttg ccagagtgag   7680
aaagggaatt gaactttcct gggagtggcc ttttaaaaag caatgagata tggccaggcc   7740
tggcttgttt ggggaagagt caaaatctag ggtggcaaga gtatgggaag cacactgagg   7800
```

```
agcagagaga aatggggtag gtaggaaggt agggttttga ccacaaagag ctgtgcatgc   7860
taaactgggc cacaggtgcc agcagggttg tttgaggaag ggaagagcaa gacaagctct   7920
ggtttaggaa gagagctgtg gcagcataaa ggcctgaaag aggagacaga gctgtcaccc   7980
aaaatggact tgagagctcc ctgtggttta ctctgtggct agaaaacact gccggccaga   8040
tggatcacaa atgtctatgg tagcttagaa gctctgctct tgaagaggat cctgggatct   8100
gcccaacacc cttcccaacc tccatttccc catccccacc tccattgccc catccccccct   8160
ctcccccctag gcaggtggat ctgagcctta tcccaccacc aatgcccctg ctagcctctc   8220
cccacccagc ccagagccta ctcagcctgc catctcaaga gccccaccga gggtcactgg   8280
cttcctggga ggagtcacca ggctgccagc tttccctctg cctccccaag gaacctgaga   8340
cctccctctg ctcatcaccc tgggcccaat cctgaatcca gcccccatca accaagacag   8400
caaaagggcc aggtctgtcc cttataattt tgagccttct ccctcaagtt tggaagccct   8460
gactttaaga aatgccaaat gcaaggacca ttaagaaaat tctccccgaa atgaggctcc   8520
tctaacaaat gatgattaaa acgctctctc cttgagcagt cacattctag aaacaggaca   8580
ttccatgagg caggaagagt tcagttaatt tgctcctgaa aaagtgtggt tcagtgtttg   8640
tgtggcaatg tacgtgggca gaagaggccg ctcaagctgt gtccccccctg agcaggattc   8700
aggaaaggga aaagaagttc tcttcaactc agccaagggg ccgtacgatg gccgatgaga   8760
ttatgtattt aaaagttctt tgtaaagtgt aaactaaaaa ccttaaatgt aagatgctgt   8820
tgttattatt actgttgttg ttgctgttat ggacatgcca aaaggccctt gttagaagac   8880
agttttgcct tttcaatctc atagcaagga actcaagtct gatgcttcaa aaagatgaga   8940
agaagggcaa gaagagggat aactcccaag ctcagaggga aaaaaaaggt gggggaaaag   9000
agccccaggg tgaccttcag gaaaggccag gaccaggatg atctaacctt tcccttcacc   9060
agaaacaaag ctattgccag actgaaccct aaagtcaagc agtcacccac tgcctttgct   9120
gggagcagaa gcccatagca acaagtgacc tgcccctcag actcaagatc ccagatacca   9180
gagctggagg agtcataggg cattactggt aggcaggaaa actgagggtc gaacaaatgg   9240
aagaatgcgg tgatcataga ccaaagacac acagataatt aaccccatgt gtccacccag   9300
gccaaagttc ttcctgctac cccacagtgg atgtccaggc agatggtccc cacatgatgg   9360
ggaagcagag ggcatagtgt ggttttgtgg gacttgttca tgttttgtag tgtgggctca   9420
acagtgccaa aggaaacact agggaaaagt tggtgaaaca tgccagctag caggaccagt   9480
aaaggcataa tcaggcattt ggcaaagctt gcttttctaa ttcaatgata ggttctaata   9540
ggaaattttt gaagattttt taaaacaatg ttatagtggc acttccccag tatggaataa   9600
ataacatgca ttcttttttc aatatactgt catattcaga tgtcattaaa ataaatggat   9660
gagtcacaga ggagctatca gatgctctca tgactaccat aactcagccc tgcaaaaaaa   9720
aaaaaaa                                                            9727
```

<210> SEQ ID NO 16
<211> LENGTH: 1523
<212> TYPE: PRT
<213> ORGANISM: Homo sapiens

<400> SEQUENCE: 16

```
Met Ala Pro Gly Trp Ala Gly Val Gly Ala Ala Val Arg Ala Arg Leu
1               5                   10                  15

Ala Leu Ala Leu Ala Leu Ala Ser Val Leu Ser Gly Pro Pro Ala Val
```

```
                20                  25                  30

Ala Cys Pro Thr Lys Cys Thr Cys Ser Ala Ala Ser Val Asp Cys His
            35                  40                  45

Gly Leu Gly Leu Arg Ala Val Pro Arg Gly Ile Pro Arg Asn Ala Glu
    50                  55                  60

Arg Leu Asp Leu Asp Arg Asn Asn Ile Thr Arg Ile Thr Lys Met Asp
65                  70                  75                  80

Phe Ala Gly Leu Lys Asn Leu Arg Val Leu His Leu Glu Asp Asn Gln
                85                  90                  95

Val Ser Val Ile Glu Arg Gly Ala Phe Gln Asp Leu Lys Gln Leu Glu
            100                 105                 110

Arg Leu Arg Leu Asn Lys Asn Lys Leu Gln Val Leu Pro Glu Leu Leu
        115                 120                 125

Phe Gln Ser Thr Pro Lys Leu Thr Arg Leu Asp Leu Ser Glu Asn Gln
    130                 135                 140

Ile Gln Gly Ile Pro Arg Lys Ala Phe Arg Gly Ile Thr Asp Val Lys
145                 150                 155                 160

Asn Leu Gln Leu Asp Asn Asn His Ile Ser Cys Ile Glu Asp Gly Ala
                165                 170                 175

Phe Arg Ala Leu Arg Asp Leu Glu Ile Leu Thr Leu Asn Asn Asn Asn
            180                 185                 190

Ile Ser Arg Ile Leu Val Thr Ser Phe Asn His Met Pro Lys Ile Arg
        195                 200                 205

Thr Leu Arg Leu His Ser Asn His Leu Tyr Cys Asp Cys His Leu Ala
    210                 215                 220

Trp Leu Ser Asp Trp Leu Arg Gln Arg Arg Thr Val Gly Gln Phe Thr
225                 230                 235                 240

Leu Cys Met Ala Pro Val His Leu Arg Gly Phe Asn Val Ala Asp Val
                245                 250                 255

Gln Lys Lys Glu Tyr Val Cys Pro Ala Pro His Ser Glu Pro Pro Ser
            260                 265                 270

Cys Asn Ala Asn Ser Ile Ser Cys Pro Ser Pro Cys Thr Cys Ser Asn
        275                 280                 285

Asn Ile Val Asp Cys Arg Gly Lys Gly Leu Met Glu Ile Pro Ala Asn
    290                 295                 300

Leu Pro Glu Gly Ile Val Glu Ile Arg Leu Glu Gln Asn Ser Ile Lys
305                 310                 315                 320

Ala Ile Pro Ala Gly Ala Phe Thr Gln Tyr Lys Lys Leu Lys Arg Ile
                325                 330                 335

Asp Ile Ser Lys Asn Gln Ile Ser Asp Ile Ala Pro Asp Ala Phe Gln
            340                 345                 350

Gly Leu Lys Ser Leu Thr Ser Leu Val Leu Tyr Gly Asn Lys Ile Thr
        355                 360                 365

Glu Ile Ala Lys Gly Leu Phe Asp Gly Leu Val Ser Leu Gln Leu Leu
    370                 375                 380

Leu Leu Asn Ala Asn Lys Ile Asn Cys Leu Arg Val Asn Thr Phe Gln
385                 390                 395                 400

Asp Leu Gln Asn Leu Asn Leu Leu Ser Leu Tyr Asp Asn Lys Leu Gln
                405                 410                 415

Thr Ile Ser Lys Gly Leu Phe Ala Pro Leu Gln Ser Ile Gln Thr Leu
            420                 425                 430

His Leu Ala Gln Asn Pro Phe Val Cys Asp Cys His Leu Lys Trp Leu
        435                 440                 445
```

Ala Asp Tyr Leu Gln Asp Asn Pro Ile Glu Thr Ser Gly Ala Arg Cys
450 455 460

Ser Ser Pro Arg Arg Leu Ala Asn Lys Arg Ile Ser Gln Ile Lys Ser
465 470 475 480

Lys Lys Phe Arg Cys Ser Gly Ser Glu Asp Tyr Arg Ser Arg Phe Ser
485 490 495

Ser Glu Cys Phe Met Asp Leu Val Cys Pro Glu Lys Cys Arg Cys Glu
500 505 510

Gly Thr Ile Val Asp Cys Ser Asn Gln Lys Leu Val Arg Ile Pro Ser
515 520 525

His Leu Pro Glu Tyr Val Thr Asp Leu Arg Leu Asn Asp Asn Glu Val
530 535 540

Ser Val Leu Glu Ala Thr Gly Ile Phe Lys Lys Leu Pro Asn Leu Arg
545 550 555 560

Lys Ile Asn Leu Ser Asn Asn Lys Ile Lys Glu Val Arg Glu Gly Ala
565 570 575

Phe Asp Gly Ala Ala Ser Val Gln Glu Leu Met Leu Thr Gly Asn Gln
580 585 590

Leu Glu Thr Val His Gly Arg Val Phe Arg Gly Leu Ser Gly Leu Lys
595 600 605

Thr Leu Met Leu Arg Ser Asn Leu Ile Gly Cys Val Ser Asn Asp Thr
610 615 620

Phe Ala Gly Leu Ser Ser Val Arg Leu Leu Ser Leu Tyr Asp Asn Arg
625 630 635 640

Ile Thr Thr Ile Thr Pro Gly Ala Phe Thr Thr Leu Val Ser Leu Ser
645 650 655

Thr Ile Asn Leu Leu Ser Asn Pro Phe Asn Cys Asn Cys His Leu Ala
660 665 670

Trp Leu Gly Lys Trp Leu Arg Lys Arg Arg Ile Val Ser Gly Asn Pro
675 680 685

Arg Cys Gln Lys Pro Phe Phe Leu Lys Glu Ile Pro Ile Gln Asp Val
690 695 700

Ala Ile Gln Asp Phe Thr Cys Asp Gly Asn Glu Glu Ser Ser Cys Gln
705 710 715 720

Leu Ser Pro Arg Cys Pro Glu Gln Cys Thr Cys Met Glu Thr Val Val
725 730 735

Arg Cys Ser Asn Lys Gly Leu Arg Ala Leu Pro Arg Gly Met Pro Lys
740 745 750

Asp Val Thr Glu Leu Tyr Leu Glu Gly Asn His Leu Thr Ala Val Pro
755 760 765

Arg Glu Leu Ser Ala Leu Arg His Leu Thr Leu Ile Asp Leu Ser Asn
770 775 780

Asn Ser Ile Ser Met Leu Thr Asn Tyr Thr Phe Ser Asn Met Ser His
785 790 795 800

Leu Ser Thr Leu Ile Leu Ser Tyr Asn Arg Leu Arg Cys Ile Pro Val
805 810 815

His Ala Phe Asn Gly Leu Arg Ser Leu Arg Val Leu Thr Leu His Gly
820 825 830

Asn Asp Ile Ser Ser Val Pro Glu Gly Ser Phe Asn Asp Leu Thr Ser
835 840 845

Leu Ser His Leu Ala Leu Gly Thr Asn Pro Leu His Cys Asp Cys Ser
850 855 860

```
Leu Arg Trp Leu Ser Glu Trp Val Lys Ala Gly Tyr Lys Glu Pro Gly
865                 870                 875                 880

Ile Ala Arg Cys Ser Ser Pro Glu Pro Met Ala Asp Arg Leu Leu Leu
                885                 890                 895

Thr Thr Pro Thr His Arg Phe Gln Cys Lys Gly Pro Val Asp Ile Asn
            900                 905                 910

Ile Val Ala Lys Cys Asn Ala Cys Leu Ser Ser Pro Cys Lys Asn Asn
        915                 920                 925

Gly Thr Cys Thr Gln Asp Pro Val Glu Leu Tyr Arg Cys Ala Cys Pro
    930                 935                 940

Tyr Ser Tyr Lys Gly Lys Asp Cys Thr Val Pro Ile Asn Thr Cys Ile
945                 950                 955                 960

Gln Asn Pro Cys Gln His Gly Gly Thr Cys His Leu Ser Asp Ser His
                965                 970                 975

Lys Asp Gly Phe Ser Cys Ser Cys Pro Leu Gly Phe Glu Gly Gln Arg
            980                 985                 990

Cys Glu Ile Asn Pro Asp Asp Cys  Glu Asp Asn Asp Cys  Glu Asn Asn
        995                 1000                 1005

Ala Thr  Cys Val Asp Gly Ile  Asn Asn Tyr Val Cys  Ile Cys Pro
    1010                 1015                 1020

Pro Asn  Tyr Thr Gly Glu Leu  Cys Asp Glu Val Ile  Asp His Cys
    1025                 1030                 1035

Val Pro  Glu Leu Asn Leu Cys  Gln His Glu Ala Lys  Cys Ile Pro
    1040                 1045                 1050

Leu Asp  Lys Gly Phe Ser Cys  Glu Cys Val Pro Gly  Tyr Ser Gly
    1055                 1060                 1065

Lys Leu  Cys Glu Thr Asp Asn  Asp Asp Cys Val Ala  His Lys Cys
    1070                 1075                 1080

Arg His  Gly Ala Gln Cys Val  Asp Thr Ile Asn Gly  Tyr Thr Cys
    1085                 1090                 1095

Thr Cys  Pro Gln Gly Phe Ser  Gly Pro Phe Cys Glu  His Pro Pro
    1100                 1105                 1110

Pro Met  Val Leu Leu Gln Thr  Ser Pro Cys Asp Gln  Tyr Glu Cys
    1115                 1120                 1125

Gln Asn  Gly Ala Gln Cys Ile  Val Val Gln Gln Glu  Pro Thr Cys
    1130                 1135                 1140

Arg Cys  Pro Pro Gly Phe Ala  Gly Pro Arg Cys Glu  Lys Leu Ile
    1145                 1150                 1155

Thr Val  Asn Phe Val Gly Lys  Asp Ser Tyr Val Glu  Leu Ala Ser
    1160                 1165                 1170

Ala Lys  Val Arg Pro Gln Ala  Asn Ile Ser Leu Gln  Val Ala Thr
    1175                 1180                 1185

Asp Lys  Asp Asn Gly Ile Leu  Leu Tyr Lys Gly Asp  Asn Asp Pro
    1190                 1195                 1200

Leu Ala  Leu Glu Leu Tyr Gln  Gly His Val Arg Leu  Val Tyr Asp
    1205                 1210                 1215

Ser Leu  Ser Ser Pro Pro Thr  Thr Val Tyr Ser Val  Glu Thr Val
    1220                 1225                 1230

Asn Asp  Gly Gln Phe His Ser  Val Glu Leu Val Thr  Leu Asn Gln
    1235                 1240                 1245

Thr Leu  Asn Leu Val Val Asp  Lys Gly Thr Pro Lys  Ser Leu Gly
    1250                 1255                 1260

Lys Leu  Gln Lys Gln Pro Ala  Val Gly Ile Asn Ser  Pro Leu Tyr
```

```
    1265                1270                1275

Leu Gly  Gly Ile Pro Thr Ser  Thr Gly Leu Ser Ala  Leu Arg Gln
    1280                1285                1290

Gly Thr  Asp Arg Pro Leu Gly  Gly Phe His Gly Cys  Ile His Glu
    1295                1300                1305

Val Arg  Ile Asn Asn Glu Leu  Gln Asp Phe Lys Ala  Leu Pro Pro
    1310                1315                1320

Gln Ser  Leu Gly Val Ser Pro  Gly Cys Lys Ser Cys  Thr Val Cys
    1325                1330                1335

Lys His  Gly Leu Cys Arg Ser  Val Glu Lys Asp Ser  Val Val Cys
    1340                1345                1350

Glu Cys  Arg Pro Gly Trp Thr  Gly Pro Leu Cys Asp  Gln Glu Ala
    1355                1360                1365

Arg Asp  Pro Cys Leu Gly His  Arg Cys His His Gly  Lys Cys Val
    1370                1375                1380

Ala Thr  Gly Thr Ser Tyr Met  Cys Lys Cys Ala Glu  Gly Tyr Gly
    1385                1390                1395

Gly Asp  Leu Cys Asp Asn Lys  Asn Asp Ser Ala Asn  Ala Cys Ser
    1400                1405                1410

Ala Phe  Lys Cys His His Gly  Gln Cys His Ile Ser  Asp Gln Gly
    1415                1420                1425

Glu Pro  Tyr Cys Leu Cys Gln  Pro Gly Phe Ser Gly  Glu His Cys
    1430                1435                1440

Gln Gln  Glu Asn Pro Cys Leu  Gly Gln Val Val Arg  Glu Val Ile
    1445                1450                1455

Arg Arg  Gln Lys Gly Tyr Ala  Ser Cys Ala Thr Ala  Ser Lys Val
    1460                1465                1470

Pro Ile  Met Glu Cys Arg Gly  Gly Cys Gly Pro Gln  Cys Cys Gln
    1475                1480                1485

Pro Thr  Arg Ser Lys Arg Arg  Lys Tyr Val Phe Gln  Cys Thr Asp
    1490                1495                1500

Gly Ser  Ser Phe Val Glu Glu  Val Glu Arg His Leu  Glu Cys Gly
    1505                1510                1515

Cys Leu  Ala Cys Ser
    1520


<210> SEQ ID NO 17
<211> LENGTH: 1523
<212> TYPE: PRT
<213> ORGANISM: Mus musculus

<400> SEQUENCE: 17

Met Ala Leu Gly Arg Thr Gly Ala Gly Ala Ala Val Arg Ala Arg Leu
1               5                   10                  15

Ala Leu Gly Leu Ala Leu Ala Ser Ile Leu Ser Gly Pro Pro Ala Ala
            20                  25                  30

Ala Cys Pro Thr Lys Cys Thr Cys Ser Ala Ala Ser Val Asp Cys His
        35                  40                  45

Gly Leu Gly Leu Arg Ala Val Pro Arg Gly Ile Pro Arg Asn Ala Glu
    50                  55                  60

Arg Leu Asp Leu Asp Arg Asn Asn Ile Thr Arg Ile Thr Lys Met Asp
65                  70                  75                  80

Phe Ala Gly Leu Lys Asn Leu Arg Val Leu His Leu Glu Asp Asn Gln
                85                  90                  95
```

-continued

```
Val Ser Ile Ile Glu Arg Gly Ala Phe Gln Asp Leu Lys Gln Leu Glu
            100                 105                 110

Arg Leu Arg Leu Asn Lys Asn Lys Leu Gln Val Leu Pro Glu Leu Leu
        115                 120                 125

Phe Gln Ser Thr Pro Lys Leu Thr Arg Leu Asp Leu Ser Glu Asn Gln
    130                 135                 140

Ile Gln Gly Ile Pro Arg Lys Ala Phe Arg Gly Val Thr Gly Val Lys
145                 150                 155                 160

Asn Leu Gln Leu Asp Asn Asn His Ile Ser Cys Ile Glu Asp Gly Ala
                165                 170                 175

Phe Arg Ala Leu Arg Asp Leu Glu Ile Leu Thr Leu Asn Asn Asn Asn
            180                 185                 190

Ile Ser Arg Ile Leu Val Thr Ser Phe Asn His Met Pro Lys Ile Arg
        195                 200                 205

Thr Leu Arg Leu His Ser Asn His Leu Tyr Cys Asp Cys His Leu Ala
    210                 215                 220

Trp Leu Ser Asp Trp Leu Arg Gln Arg Arg Thr Ile Gly Gln Phe Thr
225                 230                 235                 240

Leu Cys Met Ala Pro Val His Leu Arg Gly Phe Ser Val Ala Asp Val
                245                 250                 255

Gln Lys Lys Glu Tyr Val Cys Pro Gly Pro His Ser Glu Ala Pro Ala
            260                 265                 270

Cys Asn Ala Asn Ser Leu Ser Cys Pro Ser Ala Cys Ser Cys Ser Asn
        275                 280                 285

Asn Ile Val Asp Cys Arg Gly Lys Gly Leu Thr Glu Ile Pro Ala Asn
    290                 295                 300

Leu Pro Glu Gly Ile Val Glu Ile Arg Leu Glu Gln Asn Ser Ile Lys
305                 310                 315                 320

Ser Ile Pro Ala Gly Ala Phe Thr Gln Tyr Lys Lys Leu Lys Arg Ile
                325                 330                 335

Asp Ile Ser Lys Asn Gln Ile Ser Asp Ile Ala Pro Asp Ala Phe Gln
            340                 345                 350

Gly Leu Lys Ser Leu Thr Ser Leu Val Leu Tyr Gly Asn Lys Ile Thr
        355                 360                 365

Glu Ile Pro Lys Gly Leu Phe Asp Gly Leu Val Ser Leu Gln Leu Leu
    370                 375                 380

Leu Leu Asn Ala Asn Lys Ile Asn Cys Leu Arg Val Asn Thr Phe Gln
385                 390                 395                 400

Asp Leu Gln Asn Leu Asn Leu Leu Ser Leu Tyr Asp Asn Lys Leu Gln
                405                 410                 415

Thr Ile Ser Lys Gly Leu Phe Val Pro Leu Gln Ser Ile Gln Thr Leu
            420                 425                 430

His Leu Ala Gln Asn Pro Phe Val Cys Asp Cys His Leu Lys Trp Leu
        435                 440                 445

Ala Asp Tyr Leu Gln Asp Asn Pro Ile Glu Thr Ser Gly Ala Arg Cys
    450                 455                 460

Ser Ser Pro Arg Arg Leu Ala Asn Lys Arg Ile Ser Gln Ile Lys Ser
465                 470                 475                 480

Lys Lys Phe Arg Cys Ser Gly Ser Glu Asp Tyr Arg Asn Arg Phe Ser
                485                 490                 495

Ser Glu Cys Phe Met Asp Leu Val Cys Pro Glu Lys Cys Arg Cys Glu
            500                 505                 510

Gly Thr Ile Val Asp Cys Ser Asn Gln Lys Leu Ala Arg Ile Pro Ser
```

```
        515                 520                 525

His Leu Pro Glu Tyr Thr Thr Asp Leu Arg Leu Asn Asp Asn Asp Ile
    530                 535                 540

Ser Val Leu Glu Ala Thr Gly Ile Phe Lys Lys Leu Pro Asn Leu Arg
545                 550                 555                 560

Lys Ile Asn Leu Ser Asn Asn Arg Ile Lys Glu Val Arg Glu Gly Ala
                565                 570                 575

Phe Asp Gly Ala Ala Gly Val Gln Glu Leu Met Leu Thr Gly Asn Gln
            580                 585                 590

Leu Glu Thr Met His Gly Arg Met Phe Arg Gly Leu Ser Ser Leu Lys
        595                 600                 605

Thr Leu Met Leu Arg Ser Asn Leu Ile Ser Cys Val Ser Asn Asp Thr
    610                 615                 620

Phe Ala Gly Leu Ser Ser Val Arg Leu Leu Ser Leu Tyr Asp Asn Arg
625                 630                 635                 640

Ile Thr Thr Ile Thr Pro Gly Ala Phe Thr Thr Leu Val Ser Leu Ser
                645                 650                 655

Thr Ile Asn Leu Leu Ser Asn Pro Phe Asn Cys Asn Cys His Met Ala
            660                 665                 670

Trp Leu Gly Arg Trp Leu Arg Lys Arg Arg Ile Val Ser Gly Asn Pro
        675                 680                 685

Arg Cys Gln Lys Pro Phe Phe Leu Lys Glu Ile Pro Ile Gln Asp Val
    690                 695                 700

Ala Ile Gln Asp Phe Thr Cys Asp Gly Asn Glu Glu Ser Ser Cys Gln
705                 710                 715                 720

Leu Ser Pro Arg Cys Pro Glu Gln Cys Thr Cys Val Glu Thr Val Val
                725                 730                 735

Arg Cys Ser Asn Arg Gly Leu His Ala Leu Pro Lys Gly Met Pro Lys
            740                 745                 750

Asp Val Thr Glu Leu Tyr Leu Glu Gly Asn His Leu Thr Ala Val Pro
        755                 760                 765

Lys Glu Leu Ser Ala Phe Arg Gln Leu Thr Leu Ile Asp Leu Ser Asn
    770                 775                 780

Asn Ser Ile Ser Met Leu Thr Asn His Thr Phe Ser Asn Met Ser His
785                 790                 795                 800

Leu Ser Thr Leu Ile Leu Ser Tyr Asn Arg Leu Arg Cys Ile Pro Val
                805                 810                 815

His Ala Phe Asn Gly Leu Arg Ser Leu Arg Val Leu Thr Leu His Gly
            820                 825                 830

Asn Asp Ile Ser Ser Val Pro Glu Gly Ser Phe Asn Asp Leu Thr Ser
        835                 840                 845

Leu Ser His Leu Ala Leu Gly Thr Asn Pro Leu His Cys Asp Cys Ser
    850                 855                 860

Leu Arg Trp Leu Ser Glu Trp Val Lys Ala Gly Tyr Lys Glu Pro Gly
865                 870                 875                 880

Ile Ala Arg Cys Ser Ser Pro Glu Ser Met Ala Asp Arg Leu Leu Leu
                885                 890                 895

Thr Thr Pro Thr His Arg Phe Gln Cys Lys Gly Pro Val Asp Ile Asn
            900                 905                 910

Ile Val Ala Lys Cys Asn Ala Cys Leu Ser Ser Pro Cys Lys Asn Asn
        915                 920                 925

Gly Thr Cys Ser Gln Asp Pro Val Glu Gln Tyr Arg Cys Thr Cys Pro
    930                 935                 940
```

```
Tyr Ser Tyr Lys Gly Lys Asp Cys Thr Val Pro Ile Asn Thr Cys Val
945                 950                 955                 960

Gln Asn Pro Cys Glu His Gly Gly Thr Cys His Leu Ser Glu Asn Leu
                965                 970                 975

Arg Asp Gly Phe Ser Cys Ser Cys Pro Leu Gly Phe Glu Gly Gln Arg
            980                 985                 990

Cys Glu Ile Asn Pro Asp Asp Cys  Glu Asp Asn Asp Cys  Glu Asn Ser
        995                 1000                 1005

Ala Thr  Cys Val Asp Gly Ile  Asn Asn Tyr Ala Cys  Leu Cys Pro
    1010                 1015                 1020

Pro Asn  Tyr Thr Gly Glu Leu  Cys Asp Glu Val Ile  Asp Tyr Cys
    1025                 1030                 1035

Val Pro  Glu Met Asn Leu Cys  Gln His Glu Ala Lys  Cys Ile Ser
    1040                 1045                 1050

Leu Asp  Lys Gly Phe Arg Cys  Glu Cys Val Pro Gly  Tyr Ser Gly
    1055                 1060                 1065

Lys Leu  Cys Glu Thr Asn Asn  Asp Asp Cys Val Ala  His Lys Cys
    1070                 1075                 1080

Arg His  Gly Ala Gln Cys Val  Asp Glu Val Asn Gly  Tyr Thr Cys
    1085                 1090                 1095

Ile Cys  Pro Gln Gly Phe Ser  Gly Leu Phe Cys Glu  His Pro Pro
    1100                 1105                 1110

Pro Met  Val Leu Leu Gln Thr  Ser Pro Cys Asp Gln  Tyr Glu Cys
    1115                 1120                 1125

Gln Asn  Gly Ala Gln Cys Ile  Val Val Gln Gln Glu  Pro Thr Cys
    1130                 1135                 1140

Arg Cys  Pro Pro Gly Phe Ala  Gly Pro Arg Cys Glu  Lys Leu Ile
    1145                 1150                 1155

Thr Val  Asn Phe Val Gly Lys  Asp Ser Tyr Val Glu  Leu Ala Ser
    1160                 1165                 1170

Ala Lys  Val Arg Pro Gln Ala  Asn Ile Ser Leu Gln  Val Ala Thr
    1175                 1180                 1185

Asp Lys  Asp Asn Gly Ile Leu  Leu Tyr Lys Gly Asp  Asn Asp Pro
    1190                 1195                 1200

Leu Ala  Leu Glu Leu Tyr Gln  Gly His Val Arg Leu  Val Tyr Asp
    1205                 1210                 1215

Ser Leu  Ser Ser Pro Pro Thr  Thr Val Tyr Ser Val  Glu Thr Val
    1220                 1225                 1230

Asn Asp  Gly Gln Phe His Ser  Val Glu Leu Val Met  Leu Asn Gln
    1235                 1240                 1245

Thr Leu  Asn Leu Val Val Asp  Lys Gly Ala Pro Lys  Ser Leu Gly
    1250                 1255                 1260

Lys Leu  Gln Lys Gln Pro Ala  Val Gly Ser Asn Ser  Pro Leu Tyr
    1265                 1270                 1275

Leu Gly  Gly Ile Pro Thr Ser  Thr Gly Leu Ser Ala  Leu Arg Gln
    1280                 1285                 1290

Gly Ala  Asp Arg Pro Leu Gly  Gly Phe His Gly Cys  Ile His Glu
    1295                 1300                 1305

Val Arg  Ile Asn Asn Glu Leu  Gln Asp Phe Lys Ala  Leu Pro Pro
    1310                 1315                 1320

Gln Ser  Leu Gly Val Ser Pro  Gly Cys Lys Ser Cys  Thr Val Cys
    1325                 1330                 1335
```

```
Arg His  Gly Leu Cys Arg Ser  Val Glu Lys Asp Ser  Val Val Cys
    1340                 1345                 1350

Glu Cys  His Pro Gly Trp Thr  Gly Pro Leu Cys Asp  Gln Glu Ala
    1355                 1360                 1365

Arg Asp  Pro Cys Leu Gly His  Ser Cys Arg His Gly  Thr Cys Met
    1370                 1375                 1380

Ala Thr  Gly Asp Ser Tyr Val  Cys Lys Cys Ala Glu  Gly Tyr Gly
    1385                 1390                 1395

Gly Ala  Leu Cys Asp Gln Lys  Asn Asp Ser Ala Ser  Ala Cys Ser
    1400                 1405                 1410

Ala Phe  Lys Cys His His Gly  Gln Cys His Ile Ser  Asp Arg Gly
    1415                 1420                 1425

Glu Pro  Tyr Cys Leu Cys Gln  Pro Gly Phe Ser Gly  His His Cys
    1430                 1435                 1440

Glu Gln  Glu Asn Pro Cys Met  Gly Glu Ile Val Arg  Glu Ala Ile
    1445                 1450                 1455

Arg Arg  Gln Lys Asp Tyr Ala  Ser Cys Ala Thr Ala  Ser Lys Val
    1460                 1465                 1470

Pro Ile  Met Glu Cys Arg Gly  Gly Cys Gly Ser Gln  Cys Cys Gln
    1475                 1480                 1485

Pro Ile  Arg Ser Lys Arg Arg  Lys Tyr Val Phe Gln  Cys Thr Asp
    1490                 1495                 1500

Gly Ser  Ser Phe Val Glu Glu  Val Glu Arg His Leu  Glu Cys Gly
    1505                 1510                 1515

Cys Arg  Ala Cys Ser
    1520
```

<210> SEQ ID NO 18
<211> LENGTH: 3078
<212> TYPE: DNA
<213> ORGANISM: Homo sapiens

<400> SEQUENCE: 18

```
gtagctgaga tgcagagagc catcctgccc agacctagac aactcggaag tgggtttttc     60

agcctcctgc accggtgtcg cgtctgagtg cgactgatga gccagggggc gtcggtggaa    120

gcttggggtc ggcagtctgg ttggaaagga gaggctagtg gtaacaggcc gagctggatg    180

gatgggtatg gggagagggg caggacgttc agccctggga ttctggccga ccctcgcctt    240

ccttctctgc agcttccccg cagccacctc cccgtgcaag atcctcaagt gcaactctga    300

gttctggagc gccacgtcgg gcagccacgc cccagcctca gacgacaccc ccgagttctg    360

tgcagccttg cgcagctacg ccctgtgcac gcggcggacg gcccgcacct gccggggtga    420

cctggcctac cactcggccg tccatggcat agaggacctc atgagccagc acaactgctc    480

caaggatggc cccacctcgc agccacgcct gcgcacgctc ccaccggccg gagacagcca    540

ggagcgctcg gacagccccg agatctgcca ttacgagaag agctttcaca agcactcggc    600

cacccccaac tacacgcact gtggcctctt cggggaccca cacctcagga ctttcaccga    660

ccgcttccag acctgcaagg tgcagggcgc ctggccgctc atcgacaata attacctgaa    720

cgtgcaggtc accaacacgc ctgtgctgcc cggctcagcg gccactgcca ccagcaagct    780

caccatcatc ttcaagaact tccaggagtg tgtggaccag aaggtgtacc aggctgagat    840

ggacgagctc ccggccgcct tcgtggatgg ctctaagaac ggtggggaca agcacggggc    900

caacagcctg aagatcactg agaaggtgtc aggccagcac gtggagatcc aggccaagta    960
```

```
catcggcacc accatcgtgg tgcgccaggt gggccgctac ctgacctttg ccgtccgcat   1020
gccagaggaa gtggtcaatg ctgtggagga ctgggacagc cagggtctct acctctgcct   1080
gcggggctgc cccctcaacc agcagatcga cttccaggcc ttccacacca atgctgaggg   1140
caccggtgcc cgcaggctgg cagccgccag ccctgcaccc acagcccccg agaccttccc   1200
atacgagaca gccgtggcca agtgcaagga gaagctgccg gtggaggacc tgtactacca   1260
ggcctgcgtc ttcgacctcc tcaccacggg cgacgtgaac ttcacactgg ccgcctacta   1320
cgcgttggag gatgtcaaga tgctccactc caacaaagac aaactgcacc tgtatgagag   1380
gactcgggac ctgccaggca gggcggctgc ggggctgccc ctggcccccc ggcccctcct   1440
gggcgccctc gtcccgctcc tggccctgct ccctgtgttc tgctagacgc gtagatgtgg   1500
agggaggcgc gggctccgtc ctctcggctt ccccatgtgt gggctgggac cgcccacggg   1560
gtgcagatct cctggcgtgt ccaccatggc cccgcagaac gccagggacc gcctgctgcc   1620
aagggctcag gcacggaccc ctccccttct agtgcacgtg acaaggttgt ggtgactggt   1680
gccatgatgt ttgacagtag agctgtgtga gagggagagc agctcccctc gccccgcccc   1740
tgcagtgtga atgtgtgaaa catcccctca ggctgaagcc ccccaccccc accagagaca   1800
cactgggaac cgtcagagtc agctccttcc ccctcgcaat gcactgaaag gcccggccga   1860
ctgctgctcg ccgatccgtg gggcccccctg tgcccgccac acgcacgcac acactcttac   1920
acgagagcac actcgatccc cctaggccag cggggacacc ccagccacac agggaggcat   1980
ccttggggct tggccccagg cagggcaacc ccggggcgct gcttggcacc ttagcagact   2040
gctggaacct tttggccagt aggtcgtgcc cgcctggtgc cttctggcct gtggcctccc   2100
tgcccatgtt cacctggctg ctgtgggtac cagtgcaggt cccggttttc aggcacctgc   2160
tcagctgccc gtctctggcc tgggcccctg ccccttccac cctgtgctta gaaagtcgaa   2220
gtgcttggtt ctaaatgtct aaacagagaa gagatccttg acttctgttc ctctctctcc   2280
tgcagatgca agagctcctg ggcaggggtg cctgggcccc agggtgtggc aggagaccca   2340
gtggatgggg ccagctggcc tgccctgatc ctctgcttcc tcctcacaac cccaagagcc   2400
cccagcccgg tccatccacg tctggagtct ggggagagga gcagggtctt aggactctca   2460
gctctgagca tccctggcag ggtcttcaac ctctaatctc ttcccttaag ccctgtggcc   2520
acacagccag gagagacttg ccgctggctc ccgcctcatt tcagcccagg gtgctcatcc   2580
aggggcccag aacagtccca cctgtgctgc tgtgcccaca gcacaaagcc aggcttcact   2640
cccaaaagtg cagccaggcc ctggagggtg atcctgccag cagccctaca gctccacacc   2700
ctacccaccc atcggcagcc cctctgctgt tccccaggga cctctcatac actggccagg   2760
aggctgcaga acgtgtgtct ccccctccct ccaagaggtc ctgctccctc tgccagaacc   2820
gtgtgtgggc gggtgggagg gcgctcgggg cccggcccct ccctctccct gctggtttta   2880
gttggtccct atgttggaag taaaaagtga agcactttat tttggttgtg tttgctcacg   2940
ttctgcttgg aagtggggac ccctcactgc gtccacgtgt ctgcgacctg tgtggagtgt   3000
caccgcgtgt acatactgta aattatttat taatggctaa atgcaagtaa agtttggttt   3060
ttttgttatt ttctttta                                                   3078
```

<210> SEQ ID NO 19
<211> LENGTH: 434
<212> TYPE: PRT
<213> ORGANISM: Homo sapiens

<400> SEQUENCE: 19

```
Met Gly Met Gly Arg Gly Ala Gly Arg Ser Ala Leu Gly Phe Trp Pro
1               5                   10                  15

Thr Leu Ala Phe Leu Leu Cys Ser Phe Pro Ala Ala Thr Ser Pro Cys
            20                  25                  30

Lys Ile Leu Lys Cys Asn Ser Glu Phe Trp Ser Ala Thr Ser Gly Ser
        35                  40                  45

His Ala Pro Ala Ser Asp Asp Thr Pro Glu Phe Cys Ala Ala Leu Arg
    50                  55                  60

Ser Tyr Ala Leu Cys Thr Arg Arg Thr Ala Arg Thr Cys Arg Gly Asp
65                  70                  75                  80

Leu Ala Tyr His Ser Ala Val His Gly Ile Glu Asp Leu Met Ser Gln
                85                  90                  95

His Asn Cys Ser Lys Asp Gly Pro Thr Ser Gln Pro Arg Leu Arg Thr
            100                 105                 110

Leu Pro Pro Ala Gly Asp Ser Gln Glu Arg Ser Asp Ser Pro Glu Ile
        115                 120                 125

Cys His Tyr Glu Lys Ser Phe His Lys His Ser Ala Thr Pro Asn Tyr
    130                 135                 140

Thr His Cys Gly Leu Phe Gly Asp Pro His Leu Arg Thr Phe Thr Asp
145                 150                 155                 160

Arg Phe Gln Thr Cys Lys Val Gln Gly Ala Trp Pro Leu Ile Asp Asn
                165                 170                 175

Asn Tyr Leu Asn Val Gln Val Thr Asn Thr Pro Val Leu Pro Gly Ser
            180                 185                 190

Ala Ala Thr Ala Thr Ser Lys Leu Thr Ile Ile Phe Lys Asn Phe Gln
        195                 200                 205

Glu Cys Val Asp Gln Lys Val Tyr Gln Ala Glu Met Asp Glu Leu Pro
    210                 215                 220

Ala Ala Phe Val Asp Gly Ser Lys Asn Gly Gly Asp Lys His Gly Ala
225                 230                 235                 240

Asn Ser Leu Lys Ile Thr Glu Lys Val Ser Gly Gln His Val Glu Ile
                245                 250                 255

Gln Ala Lys Tyr Ile Gly Thr Thr Ile Val Val Arg Gln Val Gly Arg
            260                 265                 270

Tyr Leu Thr Phe Ala Val Arg Met Pro Glu Glu Val Val Asn Ala Val
        275                 280                 285

Glu Asp Trp Asp Ser Gln Gly Leu Tyr Leu Cys Leu Arg Gly Cys Pro
    290                 295                 300

Leu Asn Gln Gln Ile Asp Phe Gln Ala Phe His Thr Asn Ala Glu Gly
305                 310                 315                 320

Thr Gly Ala Arg Arg Leu Ala Ala Ala Ser Pro Ala Pro Thr Ala Pro
                325                 330                 335

Glu Thr Phe Pro Tyr Glu Thr Ala Val Ala Lys Cys Lys Glu Lys Leu
            340                 345                 350

Pro Val Glu Asp Leu Tyr Tyr Gln Ala Cys Val Phe Asp Leu Leu Thr
        355                 360                 365

Thr Gly Asp Val Asn Phe Thr Leu Ala Ala Tyr Tyr Ala Leu Glu Asp
    370                 375                 380

Val Lys Met Leu His Ser Asn Lys Asp Lys Leu His Leu Tyr Glu Arg
385                 390                 395                 400

Thr Arg Asp Leu Pro Gly Arg Ala Ala Ala Gly Leu Pro Leu Ala Pro
                405                 410                 415
```

```
Arg Pro Leu Leu Gly Ala Leu Val Pro Leu Leu Ala Leu Leu Pro Val
            420                 425                 430

Phe Cys


<210> SEQ ID NO 20
<211> LENGTH: 454
<212> TYPE: PRT
<213> ORGANISM: Mus musculus

<400> SEQUENCE: 20

Met Gln Pro Pro Arg Glu Arg Leu Val Val Thr Gly Arg Ala Gly Trp
1               5                   10                  15

Met Gly Met Gly Arg Gly Ala Gly Arg Ser Ala Leu Gly Leu Trp Pro
            20                  25                  30

Thr Leu Ala Phe Leu Leu Cys Ser Phe Pro Ala Ala Ile Ser Pro Cys
        35                  40                  45

Lys Ile Leu Lys Cys Asn Ser Glu Phe Trp Ser Ala Thr Ser Ser Gly
    50                  55                  60

Ser His Ala Pro Ala Ser Asp Asp Val Pro Glu Phe Cys Ala Ala Leu
65                  70                  75                  80

Arg Thr Tyr Ala Leu Cys Thr Arg Arg Thr Ala Arg Thr Cys Arg Gly
                85                  90                  95

Asp Leu Ala Tyr His Ser Ala Val His Gly Ile Glu Asp Leu Met Ser
            100                 105                 110

Gln His Asn Cys Ser Lys Asp Gly Pro Thr Ser Gln Pro Arg Val Arg
        115                 120                 125

Thr Leu Pro Pro Ala Gly Asp Ser Gln Glu Arg Ser Asp Ser Pro Glu
    130                 135                 140

Ile Cys His Tyr Glu Lys Ser Phe His Lys His Ser Ala Ala Pro Asn
145                 150                 155                 160

Tyr Thr His Cys Gly Leu Phe Gly Asp Pro His Leu Arg Thr Phe Thr
                165                 170                 175

Asp His Phe Gln Thr Cys Lys Val Gln Gly Ala Trp Pro Leu Ile Asp
            180                 185                 190

Asn Asn Tyr Leu Asn Val Gln Val Thr Asn Thr Pro Val Leu Pro Gly
        195                 200                 205

Ser Ala Ala Thr Ala Thr Ser Lys Leu Thr Ile Ile Phe Lys Asn Phe
    210                 215                 220

Gln Glu Cys Val Asp Gln Lys Val Tyr Gln Ala Glu Met Asp Glu Leu
225                 230                 235                 240

Pro Ser Ala Phe Ala Asp Gly Ser Lys Asn Gly Gly Asp Lys His Gly
                245                 250                 255

Ala Asn Ser Leu Lys Ile Thr Glu Lys Val Ser Gly Gln His Val Glu
            260                 265                 270

Ile Gln Ala Lys Tyr Ile Gly Thr Thr Ile Val Val Arg Gln Val Gly
        275                 280                 285

Arg Tyr Leu Thr Phe Ala Val Arg Met Pro Glu Glu Val Val Asn Ala
    290                 295                 300

Val Glu Asp Arg Asp Ser Gln Gly Leu Tyr Leu Cys Leu Arg Gly Cys
305                 310                 315                 320

Pro Leu Asn Gln Gln Ile Asp Phe Gln Ala Phe Arg Ala Asn Ala Glu
                325                 330                 335

Ser Pro Arg Arg Pro Ala Ala Ala Ser Pro Ser Pro Val Val Pro Glu
            340                 345                 350
```

```
Thr Phe Pro Tyr Glu Thr Ala Val Ala Lys Cys Lys Glu Lys Leu Pro
        355                 360                 365

Val Glu Asp Leu Tyr Tyr Gln Ala Cys Val Phe Asp Leu Leu Thr Thr
    370                 375                 380

Gly Asp Val Asn Phe Thr Leu Ala Ala Tyr Tyr Ala Leu Glu Asp Gly
385                 390                 395                 400

Lys Met Leu His Ser Asn Lys Asp Lys Leu His Leu Phe Glu Arg Thr
                405                 410                 415

Arg Glu Leu Pro Gly Ala Val Ala Ala Ala Ala Ala Ala Ala Thr Thr
            420                 425                 430

Phe Pro Leu Ala Pro Gln Ile Leu Leu Gly Thr Ile Pro Leu Leu Val
        435                 440                 445

Leu Leu Pro Val Leu Trp
    450
```

<210> SEQ ID NO 21
<211> LENGTH: 4601
<212> TYPE: DNA
<213> ORGANISM: Homo sapiens

<400> SEQUENCE: 21

```
atttgaggct gactggggag aaagctgcct ggaggaagct gctggggtgc ggggggctga      60

gggatttggc tccccgccct ctcccctaga tggcggagaa atcgggctag ctggaagggc     120

gcagctcctc tcccagagct cattctggag tcggagaact gggagagcgg cccccgaggc     180

ggagcctccc tcccgccccg agtcgcgctg ccccccacct gggggagagg ggcgggcgcc     240

gcgctgcctt ccctccgcgc ctcggccgcg tggcttgcgg cttattttcc cagctggcaa     300

gcgtcgcgct gcagacaagg gaatgcctgt ggtcctgcgt gttccgaagt tcaggggccc     360

cctgatcccg ctgagccccc tccaggagcg aaagggttaa gaatgataag gaagaagagg     420

aagcgaagcg cgcccccggg cccatgccgc agccacgggc ccagacccgc cacggcgccc     480

gcgccgccgc cctcgccgga gcccacgaga cctgcatgga cgggcatggg cttgagagca     540

gcaccttcca gcgccgccgc tgccgccgcc gaggttgagc agcgccgcag ccccgggctc     600

tgccccccgc cgctggagct gctgctgctg ctgctgttca gcctcgggct gctccacgca     660

ggtgactgcc aacagccagc ccaatgtcga atccagaaat gcaccacgga cttcgtgtcc     720

ctgacttctc acctgaactc tgccgttgac ggctttgact ctgagttttg caaggccttg     780

cgtgcctatg ctggctgcac ccagcgaact tcaaaagcct gccgtggcaa cctggtatac     840

cattctgccg tgttgggtat cagtgacctc atgagccaga ggaattgttc caaggatgga     900

cccacatcct ctaccaaccc cgaagtgacc catgatcctt gcaactatca cagccacgct     960

ggagccaggg aacacaggag aggggaccag aaccctccca gttacctttt ttgtggcttg    1020

tttggagatc ctcacctcag aactttcaag gataacttcc aaacatgcaa agtagaaggg    1080

gcctggccac tcatagataa taattatctt tcagttcaag tgacaaacgt acctgtggtc    1140

cctggatcca gtgctactgc tacaaataag atcactatta tcttcaaagc ccaccatgag    1200

tgtacagatc agaaagtcta ccaagctgtg acagatgacc tgccggccgc ctttgtggat    1260

ggcaccacca gtggtgggga cagcgatgcc aagagcctgc gtatcgtgga aagggagagt    1320

ggccactatg tggagatgca cgcccgctat atagggacca cagtgtttgt gcggcaggtg    1380

ggtcgctacc tgacccttgc catccgtatg cctgaagacc tggccatgtc ctacgaggag    1440

agccaggacc tgcagctgtg cgtgaacggc tgcccccctga gtgaacgcat cgatgacggg    1500
```

-continued

```
cagggccagg tgtctgccat cctgggacac agcctgcctc gcacctcctt ggtgcaggcc   1560
tggcctggct acacactgga gactgccaac actcaatgcc atgagaagat gccagtgaag   1620
gacatctatt tccagtcctg tgtcttcgac ctgctcacca ctggtgatgc caactttact   1680
gccgcagccc acagtgcctt ggaggatgtg gaggccctgc acccaaggaa ggaacgctgg   1740
cacattttcc ccagcagtgg caatgggact ccccgtggag gcagtgattt gtctgtcagt   1800
ctaggactca cctgcttgat ccttatcgtg tttttgtagg ggttgtcttt tgttttggtt   1860
ttttattttt tgtctataac aaaattttaa aatatatatt gtcataatat attgagtaaa   1920
agagtatata tgtatatacc atgtatatga caggatgttt gtcctgggac acccaccaga   1980
ttgtacatac tgtgtttggc tgttttcaca tatgttggat gtagtgttct ttgattgtat   2040
caattttgtt ttgcagttct gtgaaatgtt ttataatgtc cctgcccagg gacctgttag   2100
aaagcacttt atttttata tattaaatat ttatgtgtgt gcttggttga tatgtatagt   2160
acatatacac agacatccat atgcagcgtt tcctttgaag gtgaccagtt gtttgtagct   2220
attcttggct gtaccttcct gccctttccc attgctactg atttgccacg gtgtgcagct   2280
tttactcgcc accttccggt ggagctgcct cgttcctttg aactatgccc tcacccttct   2340
gccctcactt gatttgaaag ggtcgttaac tctcccttac aggtgctttg actcttaaac   2400
gctgatctta agaagctctc ttcatctaag agctgttact ttttcagaag ggggggtatt   2460
attggtattc tgattactct caattctaat tgttatatat ttgagcccat acagtgtatt   2520
aggttgaacc atagaaactg ctattctcgt aggtcaaaag ggtctagtga tggaagtttt   2580
gtagataagt accaggcatc tcagtaactc ctagactttt tctcatccca tgccccgttt   2640
taaattgtca gttttccctc tgactcttct gtgttaaaac atgaaactat aaatttagta   2700
attatcatgc cttgctcttt ttaatctata tgactgatgc aagcccctct tcttaaccgt   2760
ttcttggctt tgagcccaga aacacagctc tccctgtctc caactccagt aagccctcct   2820
cagcctcacc ttacgaatcc aaagaactgg ggtttgttag gttctttctc taatgtagag   2880
gcccagatcc catcacaaag tttttcattc ttccttgtcc accatgatct tcatcacagt   2940
ctttgatatg tctgcatgca aagtggaaca gagttgggcg gcaatgacag aagagcttcc   3000
ttggcctgac tcggtgtgcg gccacttcgg cactgcttaa tccagatatt cttgttaact   3060
aagcattgtg cttcccaggt ggtctgaagt caggtactct ctctctcaac acctgtagtt   3120
gaatatgatt tggtcagttg ctcgttgtaa cttggagaaa ttcctataaa gtaagatctc   3180
cttgcctctt ccatccattg ttggcacccc cttgcaaaag gaaaagaaca gcaaaagtca   3240
ggagcagtaa tctgagaaag ttaactccag gataggtagg tttctattgt tatagctaga   3300
tgtaaatctt tagttccaag aagtgataga gtttctgctt taataatttg ttgataagtt   3360
tacataaaca gaaataaaag atactatctt taccgtagta gttcaggcca agattatgct   3420
tagttttagt tctccaggta gttacttttg ccatgtccta ttgatcagtg acactgccag   3480
aggcccatac cggcaagagg aagaggacgt catttgtaa agtttaactt cttagcgaac   3540
tgatgtgcca cccagtcaca gagtggagtt gtgaattcat gtagaggtgg caaacctcta   3600
ccttgtgttg atgagagaat aatcttgggc agtctgggaa aataaggaag gcatctcctt   3660
cttactcatg gagattcaac tatagagagt tgaaacctaa acccgccttc cttttataga   3720
agctggacta gagacggact gaccatcagc tctgaactgt ggcttttttt gttcacctat   3780
gatgccatgt accaaattca gaagctatcg ttaataattt gttttataat tgagtagtac   3840
aagcgaggaa aaaatacgga ggataaccac tatttttgtg caaataatat gaaagtgaag   3900
```

```
taaaagcaat agaagaaatt tctataggat ctgggtttag agtgtgtatc attaataaat   3960

ataccttttgc tcttttcagg gaaaataaca accaccctta ctgatagttg ggaaaagaag   4020

attgggttat tttgccatat catttagctg gaagtgacat ttaaaagcac cctgcatcac   4080

tagtaatagt gtattttgct attctgccct tgtaatcggt gtccctgtaa aacaatcccc   4140

acagattact ttcagaaata gatgtatttc tctacgtaag ggccaggttt attttctcct   4200

tttttgagat ttctagaaaa aatgctgctt gcacatgttg gttcttgaaa ccttagctag   4260

aagaatttca ggtcatacca acatgtggat aggctatagc tgttcagagg tctcctgggg   4320

gagcttaaaa cgggggaaac actggttttc acagatgctc cacatggctg tctttaaaag   4380

actcaaaact ttttttgtc ctctttgtta tgcttggaag ctcccccccc cccaacagtg   4440

tgtcgagtct ttgcaaagaa acctttagat gtggttcata gatatatgaa tacgtatctg   4500

tgtaaaacag tgagtgtgca gtgtgtaaat actttaaatt attatgctag aaaaataaag   4560

ttacatacct tgctgtggaa aaaaaaaaaa aaaaaaaaaa a                        4601
```

<210> SEQ ID NO 22
<211> LENGTH: 478
<212> TYPE: PRT
<213> ORGANISM: Homo sapiens

<400> SEQUENCE: 22

```
Met Ile Arg Lys Lys Arg Lys Arg Ser Ala Pro Pro Gly Pro Cys Arg
1               5                   10                  15

Ser His Gly Pro Arg Pro Ala Thr Ala Pro Ala Pro Pro Pro Ser Pro
            20                  25                  30

Glu Pro Thr Arg Pro Ala Trp Thr Gly Met Gly Leu Arg Ala Ala Pro
        35                  40                  45

Ser Ser Ala Ala Ala Ala Ala Ala Glu Val Glu Gln Arg Arg Ser Pro
    50                  55                  60

Gly Leu Cys Pro Pro Pro Leu Glu Leu Leu Leu Leu Leu Leu Phe Ser
65                  70                  75                  80

Leu Gly Leu Leu His Ala Gly Asp Cys Gln Gln Pro Ala Gln Cys Arg
                85                  90                  95

Ile Gln Lys Cys Thr Thr Asp Phe Val Ser Leu Thr Ser His Leu Asn
            100                 105                 110

Ser Ala Val Asp Gly Phe Asp Ser Glu Phe Cys Lys Ala Leu Arg Ala
        115                 120                 125

Tyr Ala Gly Cys Thr Gln Arg Thr Ser Lys Ala Cys Arg Gly Asn Leu
    130                 135                 140

Val Tyr His Ser Ala Val Leu Gly Ile Ser Asp Leu Met Ser Gln Arg
145                 150                 155                 160

Asn Cys Ser Lys Asp Gly Pro Thr Ser Ser Thr Asn Pro Glu Val Thr
                165                 170                 175

His Asp Pro Cys Asn Tyr His Ser His Ala Gly Ala Arg Glu His Arg
            180                 185                 190

Arg Gly Asp Gln Asn Pro Pro Ser Tyr Leu Phe Cys Gly Leu Phe Gly
        195                 200                 205

Asp Pro His Leu Arg Thr Phe Lys Asp Asn Phe Gln Thr Cys Lys Val
    210                 215                 220

Glu Gly Ala Trp Pro Leu Ile Asp Asn Asn Tyr Leu Ser Val Gln Val
225                 230                 235                 240

Thr Asn Val Pro Val Val Pro Gly Ser Ser Ala Thr Ala Thr Asn Lys
```

```
                245                 250                 255

Ile Thr Ile Ile Phe Lys Ala His His Glu Cys Thr Asp Gln Lys Val
            260                 265                 270

Tyr Gln Ala Val Thr Asp Asp Leu Pro Ala Ala Phe Val Asp Gly Thr
        275                 280                 285

Thr Ser Gly Gly Asp Ser Asp Ala Lys Ser Leu Arg Ile Val Glu Arg
    290                 295                 300

Glu Ser Gly His Tyr Val Glu Met His Ala Arg Tyr Ile Gly Thr Thr
305                 310                 315                 320

Val Phe Val Arg Gln Val Gly Arg Tyr Leu Thr Leu Ala Ile Arg Met
                325                 330                 335

Pro Glu Asp Leu Ala Met Ser Tyr Glu Glu Ser Gln Asp Leu Gln Leu
            340                 345                 350

Cys Val Asn Gly Cys Pro Leu Ser Glu Arg Ile Asp Asp Gly Gln Gly
        355                 360                 365

Gln Val Ser Ala Ile Leu Gly His Ser Leu Pro Arg Thr Ser Leu Val
    370                 375                 380

Gln Ala Trp Pro Gly Tyr Thr Leu Glu Thr Ala Asn Thr Gln Cys His
385                 390                 395                 400

Glu Lys Met Pro Val Lys Asp Ile Tyr Phe Gln Ser Cys Val Phe Asp
                405                 410                 415

Leu Leu Thr Thr Gly Asp Ala Asn Phe Thr Ala Ala Ala His Ser Ala
            420                 425                 430

Leu Glu Asp Val Glu Ala Leu His Pro Arg Lys Glu Arg Trp His Ile
        435                 440                 445

Phe Pro Ser Ser Gly Asn Gly Thr Pro Arg Gly Gly Ser Asp Leu Ser
    450                 455                 460

Val Ser Leu Gly Leu Thr Cys Leu Ile Leu Ile Val Phe Leu
465                 470                 475


<210> SEQ ID NO 23
<211> LENGTH: 436
<212> TYPE: PRT
<213> ORGANISM: Mus musculus

<400> SEQUENCE: 23

Met Gly Val Arg Ala Ala Pro Ser Cys Ala Ala Ala Pro Ala Ala Ala
1               5                   10                  15

Gly Ala Glu Gln Ser Arg Arg Pro Gly Leu Trp Pro Pro Ser Pro Pro
            20                  25                  30

Pro Pro Leu Leu Leu Leu Leu Leu Leu Ser Leu Gly Leu Leu His Ala
        35                  40                  45

Gly Asp Cys Gln Gln Pro Thr Gln Cys Arg Ile Gln Lys Cys Thr Thr
    50                  55                  60

Asp Phe Val Ala Leu Thr Ala His Leu Asn Ser Ala Ala Asp Gly Phe
65                  70                  75                  80

Asp Ser Glu Phe Cys Lys Ala Leu Arg Ala Tyr Ala Gly Cys Thr Gln
                85                  90                  95

Arg Thr Ser Lys Ala Cys Arg Gly Asn Leu Val Tyr His Ser Ala Val
            100                 105                 110

Leu Gly Ile Ser Asp Leu Met Ser Gln Arg Asn Cys Ser Lys Asp Gly
        115                 120                 125

Pro Thr Ser Ser Thr Asn Pro Glu Val Thr His Asp Pro Cys Asn Tyr
    130                 135                 140
```

-continued

```
His Ser His Gly Gly Val Arg Glu His Gly Gly Gly Asp Gln Arg Pro
145                 150                 155                 160

Pro Asn Tyr Leu Phe Cys Gly Leu Phe Gly Asp Pro His Leu Arg Thr
                165                 170                 175

Phe Lys Asp His Phe Gln Thr Cys Lys Val Glu Gly Ala Trp Pro Leu
            180                 185                 190

Ile Asp Asn Asn Tyr Leu Ser Val Gln Val Thr Asn Val Pro Val Val
        195                 200                 205

Pro Gly Ser Ser Ala Thr Ala Thr Asn Lys Val Thr Ile Ile Phe Lys
    210                 215                 220

Ala Gln His Glu Cys Thr Asp Gln Lys Val Tyr Gln Ala Val Thr Asp
225                 230                 235                 240

Asp Leu Pro Ala Ala Phe Val Asp Gly Thr Thr Ser Gly Gly Asp Gly
                245                 250                 255

Asp Val Lys Ser Leu His Ile Val Glu Lys Glu Ser Gly Arg Tyr Val
            260                 265                 270

Glu Met His Ala Arg Tyr Ile Gly Thr Thr Val Phe Val Arg Gln Leu
        275                 280                 285

Gly Arg Tyr Leu Thr Leu Ala Ile Arg Met Pro Glu Asp Leu Ala Met
    290                 295                 300

Ser Tyr Glu Glu Ser Gln Asp Leu Gln Leu Cys Val Asn Gly Cys Pro
305                 310                 315                 320

Met Ser Glu Cys Ile Asp Asp Gly Gln Gly Gln Val Ser Ala Ile Leu
                325                 330                 335

Gly His Ser Leu Pro His Thr Thr Ser Val Gln Ala Trp Pro Gly Tyr
            340                 345                 350

Thr Leu Glu Thr Ala Ser Thr Gln Cys His Glu Lys Met Pro Val Lys
        355                 360                 365

Asp Ile Tyr Phe Gln Ser Cys Val Phe Asp Leu Leu Thr Thr Gly Asp
    370                 375                 380

Ala Asn Phe Thr Ala Ala Ala His Ser Ala Leu Glu Asp Val Glu Ala
385                 390                 395                 400

Leu His Pro Arg Lys Glu Arg Trp His Ile Phe Pro Ser Ser Cys Gly
                405                 410                 415

Gly Cys Arg Asp Leu Pro Val Gly Leu Gly Leu Thr Cys Leu Ile Leu
            420                 425                 430

Ile Met Phe Leu
        435
```